US009523698B2

(12) United States Patent
Rouleau et al.

(10) Patent No.: US 9,523,698 B2
(45) Date of Patent: Dec. 20, 2016

(54) METHOD OF PROGNOSING AND DIAGNOSING HEREDITARY SPASTIC PARAPLEGIA, MUTANT NUCLEIC ACID MOLECULES AND POLYPEPTIDES

(71) Applicants: Universite Montreal, Montreal (CA); The Royal Institution for the Advancement of Learning/McGill University, Montreal (CA); Val-Chum L.P., Montreal (CA)

(72) Inventors: Guy A. Rouleau, Montreal (CA); Paul Valdmanis, Montreal (CA); Inge Meijer, Montreal (CA); Pierre Drapeau, Montreal (CA); Patrick Dion, St-Hyacinthe (CA)

(73) Assignees: Val-Chum L.P., Montreal, Quebec (CA); The Royal Institution for the Advancement of Learning/McGill University, Montreal, Quebec (CA); Universite de Montreal, Montreal, Quebec (CA)

( * ) Notice: Subject to any disclaimer, the term of this patent is extended or adjusted under 35 U.S.C. 154(b) by 110 days.

(21) Appl. No.: 13/958,428

(22) Filed: Aug. 2, 2013

(65) Prior Publication Data
US 2014/0065724 A1 Mar. 6, 2014

Related U.S. Application Data

(62) Division of application No. 13/110,640, filed on May 18, 2011, now Pat. No. 8,518,657, which is a division of application No. 11/983,957, filed on Nov. 13, 2007, now Pat. No. 7,989,167.

(60) Provisional application No. 60/858,354, filed on Nov. 13, 2006.

(51) Int. Cl.
*G01N 33/68* (2006.01)
*C07K 16/18* (2006.01)
*C07K 14/47* (2006.01)
*C12Q 1/68* (2006.01)

(52) U.S. Cl.
CPC ........... *G01N 33/6896* (2013.01); *C07K 14/47* (2013.01); *C07K 16/18* (2013.01); *C12Q 1/6883* (2013.01); *C12Q 2600/136* (2013.01); *C12Q 2600/156* (2013.01); *C12Q 2600/172* (2013.01); *G01N 2500/00* (2013.01)

(58) Field of Classification Search
None
See application file for complete search history.

(56) References Cited

U.S. PATENT DOCUMENTS 7,989,167 B2  8/2011 Rouleau et al.

FOREIGN PATENT DOCUMENTS

WO  WO 9738085  10/1997

OTHER PUBLICATIONS

Porkka et al., Genes, Chromosomes & Cancer, 39:1-10, 2004.*
Behan, W.M. and M. Maia, "Strumpell's Familial Spastic Paraplegia: Genetics and Neuropathology," Journal of Neurology, 37:8-20 (1974).
Bourgeois, S. and D. Labuda, "Dynamic Allele-Specific Oligonucleotide Hybridization on Solid Support," Anal. Biochem., 324:309-311 (2004).
Brand, M., et al., "Mutations Affecting Development of the Midline and General Body Shape During Zebrafish Embrygenesis," Development, 123:129-142 (1996).
Casari, G., et al., "Spastic Paraplegia and OXPHOS Impairment Caused by Mutations in Paraplegin, a Nuclear-Encoded Mitochondrial Metalloprotease," Cell, 93:973-983 (Jun. 1998).
Cottingham, R.W., et al., "Faster Sequential Genetic Linkage Computations," Am. J. Hum. Genet., 53:252-263 (Feb. 1993).
Deluca, G.C., et al. "The Extent of Axonal Loss in the Long Tracts in Hereditary Spastic Paraplegia," Neuropathy Appl. Neurobiol., 30:576-584 (2004).
Djinovic-Carugo, K., et al., "The Spectrin Repeat: A Structural Platform for Cytoskeletal Protein Assemblies," FEBS Lett. 513:119-123 (Jan. 2002).
Do, C.B., et al., "ProbCons: Probalistic Consistency-Based Multiple Sequence Alignment," Genome Res., 15:330-340 (2005).
Fink, J.K., "Advances in Hereditary Spastic Paraplegia," Current Opinion in Neurology, 10:313-318 (1997).
Finn, R.D., et al., "Pfam: Clains, Web Tools and Services," Nucleic Acids Research, 34:D247-D251 (2006).
Guex, N., et al., "Swiss-Model and the Swiss PdbViewer" An Environment for Comparative Protein Modeling, Electrophoresis, 18:2714-2723 (1997).
Harding, A.E., "Classification of the Hereditary Ataxias and Paraplegias," Lancet, 1:1151-1155 (May 1983).
Harding, A.E., "Hereditary Spastic Paraplegia," Seminars in Neurology, 13:333-336 (Dec. 1993).
Hazan, J., et al., "Spastin, a New AAA Protein, is Altered in the Most Frequent Form of Autosomal Dominant Spastic Paraplegia," Nature Genetics, 23:296-303 (1999).
Hebsgaard, S.M., et al., "Splice Site Prediction in Arabidopsis Thaliana pre-mRNA by Combining Local and Global Sequence Information," Nucleic Acids Research, 24:3439-3452 (Jul. 1996).
Hedera, P., et al., "Novel Locus for Autosomal Dominant Hereditary Spastic Paraoplegia, on Chromosome 8q," Am. J. Hum. Genet., 64:563-569 (Jan. 1999).

(Continued)

*Primary Examiner* — Gregory S Emch
*Assistant Examiner* — Stacey N MacFarlane
(74) *Attorney, Agent, or Firm* — Foley & Lardner LLP

(57) ABSTRACT

A method for diagnosing the presence of hereditary spastic paraplegia (HSP) or predicting the risk of developing HSP in a human subject, comprising detecting the presence or absence of a defect in a gene encoding a polypeptide comprising the sequence of FIG. 9 (SEQ ID NO: 19), in a nucleic acid sample of the subject, whereby the detection of the defect is indicative that the subject has or is at risk of developing HSP.

14 Claims, 33 Drawing Sheets

(56) References Cited

OTHER PUBLICATIONS

Hirose, F., et al., "Novel 8-Base Pair Sequence (*Drosphila* DNA Replication-Related Element) and Specific Binding Factor Involved in the Expression of *Drosophila* Genes for DNA Polymerase α and Proliferating Cell Nuclear Antigen," Jour. Biol. Chem., 268:2092-2099 (1993).
Hochheimer, A., et al., "TRF2 Associates with DREF and Directs Promoter-Selective Gene Expression in *Drosophila*," Nature, 420:439-445 (Nov. 2002).
Ikeda, Y., et al., "Spectrin Mutations Cause Spinocerebellar Ataxia Type 5," Nat. Genet., 38:184-190 (2005).
Ishikawa, K., et al., "An Autosomal Dominant Cerebellar Ataxia Linked to Chromosome 16q22.1 is Associated with a Single-Nucleotide Substitution in the 5' Untranslated Region of the Gene Encoding a Protein with Spectrin Repeat and Rho Guanine-Nucleotide Exchange-Factor Domains," Am. J. Hum. Genet., 77:280-296 (Jul. 2005).
Jones, D.T., "Protein Secondary Structure Prediction Based on Position-Specific Scoring Matrices," J. Mol. Biol., 292:195-202 (1999).
Jouet, M., et al., "X-Linked Spastic Paraplegia (SPG1), MASA Syndrome and X-Linked Hydrocephalus Result from Mutations in the L1 Gene," Nat. Genet., 7:402-407 (Jul. 1994).
Kelley, L.A., et al. "Enhanced Genome Annotation Using Structural Profiles in the Program 3D-PSSM," J. Mol. Biol., 299:499-520 (2000).
Kent, W.J., et al., "The Human Genome Browser at UCSC," Genome Res. 12:996-1006 (2002).
Klebe, S., et al., "Autosomal Recessive Spastic Paraplegia (SPG30) With Mild Ataxia and Sensory Neuropathy Maps to Chromosome 2q37.3," Brain, 129:1456-1462 (Jan. 2006).
Koenig, M., "The Complete Sequence of Dystrophin Predicts a Rod-Shaped Cytoskeletal Protein," Cell, 53:219-228 (1988).
Labuda, D., et al., "Rapid Detection of CYP1A1, CYP2D6, and NAT Variants by Multiplex Polymerase Chain Reaction and Allele-Specific Oligonuculeotide Assay," Analytical Biochemistry, 275:84-92 (May 1999).
Mannan, A.U., et al., "ZFYVE27 (SPG33), a Novel Spastin-Binding Protein, is Mutated in Hereditary Spastic Paraplegia," Am. J. Hum. Genet., 79:351-357 (Aug. 2006).
McMonagle, P., et al. "The Prevalence of "Pure" Autosomal Dominant Hereditary Spastic Paraparesis in the Island of Ireland," J. Neurol. Neurosurg. Psychiatry, 72:43-46 (2002).
Meijer, I.A., "Spectrum of SPG4 Mutations in a Large Collection of North American Families With Hereditary Spastic Paraplegia," Arch. Neurol., 59:281-286 (2002).
Nagase, T., et al., "Prediction of the Coding Sequence of Unidentified Human Genes. V. the Coding Sequence of 40 New Genes (KIAA0161-KIAA0200) Deduced by Analysis of cDNA Clones from Human Cell Line KG-1," DNA Research, 3:17-24 (Feb. 1996).
Nasevicius, A. and S.C. Ekker, "Effective Targeted Gene 'Knockdown' in Zebrafish," Nat. Genet., 26:216-220 (Oct. 2000).
Polo, J.M., et al., "Hereditary Ataxias and Paraplegias in Cantabria, Spain," Brain, 114:855-866 (1991).
Porkka, K.P., et al., "RAD21 and KIAA0196 and 8q24 are Amplified and Overexpressed in Prostate Cancer," Genes Chromosomes SpecialAnd Cancer, 39:1-10 (Aug. 2003).
Quevillon, E., et al., "InterProScan: Protein Domains Identifier," Nucleic Acids Research, 33:W116-W120 (Mar. 2005).
Reid, E., et al., "Autosomal Dominant Spastic Paraplegia," Neurology, 53:1844-1849 (1999).
Rocco, P., et al., "Brazilian Family With Pure Autosomal Dominant Spastic Paraplegia Maps to 8q: Analysis of Muscle Beta 1 Syntrophin," Am. J. Med. Genet., 92:122-127 (2000).
Shimada, M., et al., "TATA-Binding Protein-Like Protein (TLP/TRF2/TLF) Negatively Regulates Cell Cycle Progression and is Required for the Stress-Mediated G2 Checkpoint," Mol. Cell Biol., 23:4107-4120 (Jun. 2003).
Silva, M.C., et al., "Hereditary Ataxias and Spastic Paraplegias: Methodological Aspects of a Prevalence Study in Portugal," J. Clin. Epidemiol., 50:1377-1384 (Aug. 1997).
Soderblom, C. and C. Blackstone, "Traffic Accidents: Molecular Genetic Insights into the Pathogenesis of the Hereditary Spastic Paraplegias," Pharmacol. Ther., 109:42-56 (2006).
Westerfield M., The Zebrafish Book. A Guide for Laboratory Use of Zebrafish (*Danio rerio*), Chapters 2-5, 7-8 C. Walker and G. Streisinger.
Wood, J.D., et al., "The Microtubule-Severing Protein Spastin is Essential for Axon Outgrowth in the Zebrafish Embryo," Hum. Mol. Genet., 15:2763-2771 (Aug. 2006).
Ylanne, J., et al., "Crystal Structure of the SpecialA-Actinin Rod: Four Spectrin Repeats Forming a Tight Dimer," Cell. Biol. Mol. Lett. 6:234 (2001).
Zuchner, S., et al., "A New Locus for Dominant Hereditary Spastic Paraplegia Maps to Chromosome 2p12," Neurogenetics, 7:127-129 (Mar. 2006).

* cited by examiner

```
HUMAN        VSQYYSGELVSYVRKVLQIIPESMF
ORANGUTAN    vsqyysgelvsyvrkvlqiipesmf
RAT          vsqyysgelvsyvrkvlqiipesmf
MOUSE        vsqyysgelvsyvrkvlqiipesmf
DOG          vsqyysgelvsyvrkvlqiipesmf
CHICKEN      vsqyysgelvsyvrkvlqiipesmf
ZEBRAFISH    vsqfysgelvsyvrkvlqiipesmf
FRUIT FLY    vsnyystelanflrrvlqivpetmf
C. ELEGANS   iantysyaleknlktvlqsvpqhlf
FRON         vsqyysgelvfyvrkvlqiipesmf
AMOEBA       vseyysgelvgyvrkvleivpkqmf
                       ↑         ↑
                   P.L619F    P.V626F
```

FIG. 3D

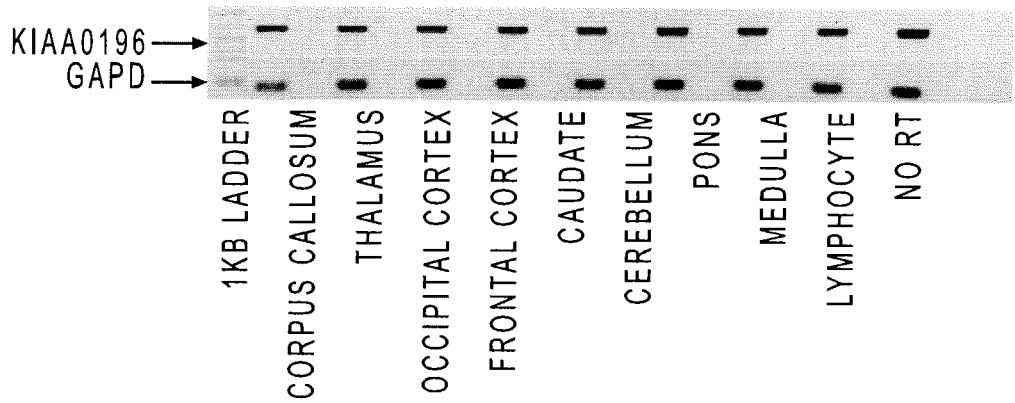

FIG. 3E

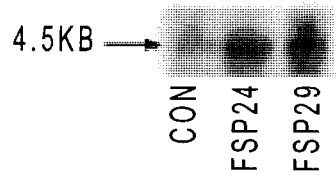

FIG. 3F

NM_014846.3
acatgatgcccctccctgctcccagccgcttcggtcatgtgaccgcctggggagtcaggggcggaagtcggggtctgacc
cgctccaggtccgggactgcggatagaagaggaccgccgccttgagggaggggtggaaactgggtgccggctccgcg
cgcgacctccggccctgcgcgtgcgccgtggcgcggcccggctgacaggttctttaatggaggagccaatctctctgcac
acctggtttcatctaataatatacagacaccagctctgaggccagttaatcatcccagtgtccaggcacagagtagtcggtc
cgcctcacaatgttggactttctagccgagaacaacctctgtggccaagcaatcctaaggattgtttcctgtggtaatgccatc
attgctgaacttttgagactctctgagtttattcctgctgtgttcaggttaaaagacagagctgatcaacagaaatatggagatat
catatttgatttcagctattttaagggtccagaattatgggaaagcaaactggatgctaagccagagctacaggatttagatga
agaatttcgtgaaaacaacatagaaattgtgaccagattttatttagcatttcaaagtgtacataaatatattgtagacttaaaca
gatatctagatgatctcaatgaagggtttatattcagcaaaccttagaaactgtgcttctcaatgaagatggaaaacaacttct
atgtgaagcactgtacttatatggagttatgctactggtcattgaccaaaagattgaaggagaagtcagagagaggatgctg
gtttcttactaccgatacagtgctgctcgatcttctgctgattcaaatatggacgatatttgtaagctgcttcgaagtacaggttat
tctagccaaccaggtgccaaaagaccatccaactatcccgagagctatttccagagagtgcctatcaacgaatccttcatca
gtatggtcattggtcgactgagatctgatgatatttacaaccaggtctcagcgtatcctttgccggagcatcgcagcacagcc
ctggcaaaccaagctgccatgctgtacgtgattctctactttgagccttccatccttcacacccatcaagcaaaaatgagaga
gatagtggataaatactttccagataattgggtaattagtatttacatggggatcacagttaatctagtagatgcttgggaacctt
acaaagctgcaaaaactgctttaaataatacectggaccttcaaatgtcagagaacaggcaagcagatatgctactgtcagt
gaaagagtgcatgctcaagtgcagcaatttctaaaagaaggttatttaagggaggagatggttctggacaatatcccaaagc
ttctgaactgcctgagagactgcaatgttgccatccgatggctgatgcttcatacagcagactcagcctgtgacccaaacaa
caaacgccttcgtcaaatcaaggaccagattctaacagactctcggtacaatcccaggatcctcttccagctgctgttagata
ctgcacaatttgagtttatactcaaagagatgttcaagcaaatgctttcagaaaagcaaaccaaatgggagcattacaagaa
gagggttcggagcggatgactgagcttgctgatgtcttttcaggagtgaaacccctaaccagagtggagaaaaatgaaaac
cttcaagcttggttcagagagatctcaaaacaaatattgtctttaaattatgatgattctactgctgcgggcagaaaaactgtac
aactgatacaagctttggaagaggttcaagaattccaccagttggaatccaatctgcaagtatgtcagtttcttgccgatactc
gaaagtttcttcatcaaatgatcagaaccattaacattaaagaggaggttctgatcacaatgcagatcgttggggacctttcttt
cgcttggcagttgattgacagtttcacatccatcatgcaagaaagcataagggtaaatccatccatggttactaaactcagag
ctaccttcctaaagcttgcctctgccctcgatctgccccttcttcgtattaatcaggcaaatagccccgacctgctcagcgtgtc
acagtactattctggagagttggtatcctatgtgagaaaagttttgcagatcatcccagaaagcatgtttacatctcttctaaag
atcataaagcttcagacccacgacattattgaagtgcctacccgcctggacaaagacaagctgagggactatgctcagcta
ggcccacgatacgaggttgccaagcttactcatgctatttccattttactgaaggcatcttaatgatgaaaacgactttggttg
gcatcatcaaggtggatccaaagcagttgctggaagatggaataaggaaagagcttgtgaagcgcgttgcctttgccctgc
ataggggactgatattcaaccctcgagccaagccaagtgaattgatgcccaagctgaaagagttgggagcgaccatggat
ggattccatcgttcttttgaatacatacaggactatgtcaacatttatggtctgaagatttggcaggaagaagtatctcgtatcat
aaattacaacgtggagcaagagtgtaataactttctaagaacgaagattcaagattggcaaagcatgtaccagtccactcata
ttccaatacccaagtttacccctgtggatgagtctgtaacgtttattggtcgactctgcagagaaatcctgcggatcacagacc
caaaaatgacatgtcacatagaccagctgaacacttggtatgatatgaaaactcatcaggaagtgaccagcagccgcctctt
ctcagaaatccagaccaccttgggaacctttggtctaaatggcttagacaggcttctgtgctttatgattgtaaaagagttaca
gaatttcctcagtatgtttcagaaaattatcctgagagacagaactgttcaggacactttaaaaaccctcatgaatgctgtcagt
cccctaaaaagtattgtcgcaaattcaaataaaaatttatttttccgccattgccaaaacacagaagatttggactgcgtatctcg
aggctataatgaaggttgggcagatgcagattctgagacaacagattgccaatgaattaaattattcttgtcggtttgattctaa
acatctggcagctgctctggagaatctcaataaggctctcctagcagacattgaagcccactatcaggaccettcacttcctt
accccaaagaagataacacacttttatatgaaatcacagcctatctggaggcagctggcattcacaacccactgaataagat
atacataacaacaaagcgcttaccctatttccaattgtaaactttctatttttgatcgctcagttgccaaaacttcaatacaacaa aaatctgggaatggtctgccgaaaaccgaccgacccggttgattggccaccacttgtcctgggactgctcactctgctgaa
gcagttccattcccggtacaccgagcagttcctggcgctgattggccagtttatctgctccacggtggagcagtgtacaagc
cagaagatacctgaaattcctgcagatgttgtgggtgcccttctgttcctggaggattatgttcggtacacaaagctacccag
gagggttgctgaagcacatgtgcctaatttcattttgatgagttcagaacagtgctgtaactgttttcctacttcttcaatggaa
ggattgtccttagatcttcccaccatcacaaatgaatttgaagatgaaaagaaactcagttgctcatacaactgcatttttctgt
ctattatgggaaacatcagacgttctgagtaagatatatctcatggcattagttaatataactgatattgtttaaatcatggtattac
atgcaatttatatcagataaaagcagaacacattttgtactgcctctcttaaatgctgaatgtaactgttatgtataaatccattta
gttttatgttctaaagaactatttgtgcaactccagattttcagtaaaatagtattactagtacccaaaaaaaaaa (SEQ ID NO: 18)

Figure 8 (continued)

NP_055661 mldflaennlcgqailrivscgnaiiaellrlsefipavfrlkdradqqkygdiifdfsyfkgpelweskldakpelqdldeefrennieivtrf
ylafqsvhkyivdlnrylddlnegvyiqqtletvllnedgkqllcealylygvmllvidqkiegevrermlvsyyrysaarssadsnmdd
ickllrstgyssqpgakrpsnypesyfqrvpinesfismvigrlrsddiynqvsayplpehrstalanqaamlyvilyfepsilhthqak
mreivdkyfpdnwvisiymgitvnlvdawepykaaktalnntldlsnvreqasryatvservhaqvqqflkegylreemvldnipkll
nclrdcnvairwlmlhtadsacdpnnkrlrqikdqiltdsrynprilfqllldtaqfefilkernfkqmlsekqtkwehykkegsermtela
dvfsgvkpltrveknenlqawfreiskqilslnyddstaagrktvqliqaleevqefhqlesnlqvcqfladtrkflhqmirtinikeevlit
mqivgdlsfawqlidsftsimqesirvnpsmvtklratflklasaldlpllrinqanspdllsvsqyysgelvsyvrkvlqiipesmftsllkii
klqthdiievptrldkdklrdyaqlgpryevaklthaisiftegilmmkttlvgiikvdpkqlledgirkelvkrvafalhrglifnprakpsel
mpklkelgatmdgfhrsfeyiqdyvniyglkiwqeevsriinynveqecnnflrtkiqdwqsmyqsthipipkftpvdesvtfigrlcre
ilritdpkmtchidqlntwydmkthqevtssrlfseiqttlgtfglngldrllcfmivkelqnflsmfqkiilrdrtvqdtlktlmnavsplksiva
nsnkiyfsaiaktqkiwtayleaimkvgqmqilrqqianelnyscrfdskhlaaalenlnkalladieahyqdpslpypkedntllyeit
ayleaagihnplnkiyittkrlpyfpivnflfliaqlpklqynknlgmvcrkptdpvdwpplvlglltllkqfhsryteqflaligqficstveqct
sqkipeipadvvgallfledyvrytklprrvaeahvpnfifdefrtvl    (SEQ ID NO: 19)

Figure 9

KIAA0196 N471D (c.1740a>g) nucleotide sequence acatgatgcccctccctgctcccagccgcttcggtcatgtgaccgcctggggagtcaggggcggaagtcggggtctgacc
cgctccaggtccgggactgcggatagaagaggaccgccgccttgagggaggggtggaaactgggtgccggctccgcg
cgcgacctccggccctgcgcgtgcgccgtggcgcggcccggctgacaggttctttaatggaggagccaatctctctgcac
acctggtttcatctaataatatacagacaccagctctgaggccagttaatcatcccagtgtccaggcacagagtagtcggtc
cgcctcacaatgttggactttctagccgagaacaacctctgtggccaagcaatcctaaggattgtttcctgtggtaatgccatc
attgctgaacttttgagactctctgagtttattcctgctgtgttcaggttaaaagacagagctgatcaacagaaatatggagatat
catatttgatttcagctattttaagggtccagaattatgggaaagcaaactggatgctaagccagagctacaggattagatga
agaatttcgtgaaaacaacatagaaattgtgaccagatttatttagcatttcaaagtgtacataaatatattgtagacttaaaca
gatatctagatgatctcaatgaagggggtttatattcagcaaaccttagaaactgtgcttctcaatgaagatggaaaacaacttct
atgtgaagcactgtacttatatggagttatgctactggtcattgaccaaaagattgaaggagaagtcagagagaggatgctg
gtttcttactaccgatacagtgctgctcgatcttctgctgattcaaatatggacgatatttgtaagctgcttcgaagtacaggttat
tctagccaaccaggtgccaaaagaccatccaactatcccgagagctatttccagagagtgcctatcaacgaatccttcatca
gtatggtcattggtcgactgagatctgatgatatttacaaccaggtctcagcgtatcctttgccggagcatcgcagcacagcc
ctggcaaaccaagctgccatgctgtacgtgattctctactttgagccttccatccttcacacccatcaagcaaaaatgagaga
gatagtggataaatactttccagataattgggtaattagtatttacatgggggatcacagttaatctagtagatgcttgggaacctt
acaaagctgcaaaaactgctttaaataataccctggaccttcaaatgtcagagaacaggcaagcagatatgctactgtcagt
gaaagagtgcatgctcaagtgcagcaatttctaaaagaaggttatttaagggaggagatggttctggacaatatcccaaagc
ttctgaactgcctgagagactgcaatgttgccatccgatggctgatgcttcatacagcagactcagcctgtgacccaaacaa
caaacgccttcgtcaaatcaaggaccagattctaacagactctcggtacaatcccaggatcctcttccagctgctgttagata
ctgcacaatttgagtttatactcaaagagatgttcaagcaaatgctttcagaaaagcaaaccaaatgggagcattacaagaaa
gagggttcggagcggatgactgagcttgctgatgtcttttcaggagtgaaaccccctaaccagagtggagaaaaatgaagac
cttcaagcttggttcagagagatctcaaaacaaatattgtctttaaattatgatgattctactgctgcgggcagaaaaactgtac
aactgatacaagctttggaagaggttcaagaattccaccagttggaatccaatctgcaagtatgtcagtttcttgccgatactc
gaaagtttcttcatcaaatgatcagaaccattaacattaaagaggaggttctgatcacaatgcagatcgttggggacctttcttt
cgcttggcagttgattgacagtttcacatccatcatgcaagaaagcataagggtaaatccatccatggttactaaactcagag
ctaccttcctaaagcttgcctctgccctcgatctgccccttcttcgtattaatcaggcaaatagccccgacctgctcagcgtgtc
acagtactattctggagagttggtatcctatgtgagaaaagttttgcagatcatcccagaaagcatgtttacatctcttctaaag
atcataaagcttcagacccacgacattattgaagtgcctacccgcctggacaaagacaagctgagggactatgctcagcta
ggcccacgatacgaggttgccaagcttactcatgctatttccattttttactgaaggcatcttaatgatgaaaacgacttttggttg
gcatcatcaaggtggatccaaagcagttgctggaagatggaataaggaaagagcttgtgaagcgcgttgcctttgccctgc
ataggggactgatattcaaccctcgagccaagccaagtgaattgatgcccaagctgaaagagttgggagcgaccatggat
ggattccatcgttcttttgaatacatacaggactatgtcaacatttatggtctgaagatttggcaggaagaagtatctcgtatcat
aaattacaacgtggagcaagagtgtaataactttctaagaacgaagattcaagattggcaaagcatgtaccagtccactcata
ttccaatacccaagtttaccccctgtggatgagtctgtaacgtttattggtcgactctgcagagaaatcctgcggatcacagacc
caaaaatgacatgtcacatagaccagctgaacacttggtatgatatgaaaactcatcaggaagtgaccagcagccgcctctt
ctcagaaatccagaccaccttgggaacctttggtctaaatggcttagacaggcttctgtgcttatgattgtaaaagagttaca
gaatttcctcagtatgtttcagaaaattatcctgagagacagaactgttcaggacactttaaaaaccctcatgaatgctgtcagt
cccctaaaaagtattgtcgcaaattcaaataaaatttattttccgccattgccaaaacacagaagatttggactgcgtatctcg
aggctataatgaaggttgggcagatgcagattctgagaca

Figure 10 acagattgccaatgaattaaattattcttgtcggtttgattctaaacatctggcagctgctctggagaatctcaataaggctctcc
tagcagacattgaagcccactatcaggacccttcacttccttaccccaaagaagataacacactttatatgaaatcacagcct
atctggaggcagctggcattcacaacccactgaataagatatacataacaacaaagcgcttaccctatttccaattgtaaact
ttctattttgatcgctcagttgccaaaacttcaatacaacaaaaatctgggaatggtctgccgaaaaccgaccgacccggttg
attggccaccacttgtcctgggactgctcactctgctgaagcagttccattcccggtacaccgagcagttcctggcgctgatt
ggccagtttatctgctccacggtggagcagtgtacaagccagaagatacctgaaattcctgcagatgttgtgggtgcccttct
gttcctggaggattatgttcggtacacaaagctacccaggagggttgctgaagcacatgtgcctaatttcatttttgatgagttc
agaacagtgctgtaactgttttcctacttcttcaatggaaggattgtccttagatcttcccaccatcacaaatgaatttgaagat
gaaaagaaactcagttgctcatacaactgcattttttctgtctattatgggaaacatcagacgttctgagtaagatatatctcatg
gcattagttaatataactgatattgtttaaatcatggtattacatgcaatttatatcagataaaagcagaacacattttttgtactgcc
tctcttaaatgctgaatgtaactgttatgtataaatccatttagttttatgttctaaagaactatttgtgcaactccagattttcagtaa
aatagtattactagtacccaaaaaaaaaa (SEQ ID NO: 20)

Figure 10 (continued)

KIAA0196 N471D mutant protein sequence

```
mldflaennlcgqailrivscgnaiiaellrlsefipavfrlkdradqqkygdiifdfsyfkgpelweskldakpe
lgdldeefrennieivtrfylafqsvhkyivdlnrylddlnegvyiqqtletvllnedgkqllcealylygvmllv
idqkiegevrermlvsyyrysaarssadsnmddickllrstgyssqpgakrpsnypesyfqrvpinesfismvigr
lrsddiynqvsayplpehrstalanqaamlyvilyfepsilhthqakmreivdkyfpdnwvisiymgitvnlvdaw
epykaaktalnntldlsnvreqasryatvservhaqvqqflkegylreemvldnipkllnclrdcnvairwlmlht
adsacdpnnkrlrqikdqiltdsrynprilfqllldtaqfefilkemfkqmlsekqtkwehykkegsermteladv
fsgvkpltrveknedlqawfreiskqilslnyddstaagrktvqliqaleevqefhqlesnlqvcqfladtrkflh
qmirtinikeevlitmqivgdlsfawqlidsftsimqesirvnpsmvtklratflklasaldlpllrinqanspdl
lsvsqyysgelvsyvrkvlqiipesmftsllkiiklqthdiievptrldkdklrdyaqlgpryevaklthaisift
egilmmkttlvgiikvdpkqlledgirkelvkrvafalhrglifnprakpselmpklkelgatmdgfhrsfeyiqd
yvniyglkiwqeevsriinynveqecnnflrtkiqdwqsmyqsthipipkftpvdesvtfigrlcreilritdpkm
tchidqlntwydmkthqevtssrlfseiqttlgtfglngldrllcfmivkelqnflsmfqkiilrdrtvqdtlktl
mnavsplksivansnkiyfsaiaktqkiwtayleaimkvgqmqilrqqianelnyscrfdskhlaaalenlnkall
adieahyqdpslpypkedntllyeitayleaagihnplnkiyittkrlpyfpivnflfliaqlpklqynknlgmvc
rkptdpvdwpplvlglltllkqfhsryteqflaligqficstveqctsqkipeipadvvgallfledyvrytklpr
rvaeahvpnfifdefrtvl (SEQ ID NO: 21)
```

Figure 11

KIAA0196 L619F (c.2186g>c) nucleotide sequence acatgatgcccctccctgctcccagccgcttcggtcatgtgaccgcctggggagtcaggggcggaagtcggggtctgacc
cgctccaggtccgggactgcggatagaagaggaccgccgccttgagggagggtggaaactgggtgccggctccgcg
cgcgacctccggccctgcgcgtgcgccgtggcgcggcccggctgacaggttctttaatggaggagccaatctctctgcac
acctggtttcatctaataatatacagacaccagctctgaggccagttaatcatccccagtgtccaggcacagagtagtcggtc
cgcctcacaatgttggactttctagccgagaacaacctctgtggccaagcaatcctaaggattgttcctgtggtaatgccatc
attgctgaacttttgagactctctgagtttattcctgctgtgttcaggttaaaagacagagctgatcaacagaaatatggagatat
catatttgatttcagctatttttaagggtccagaattatgggaaagcaaactggatgctaagccagagctacaggatttagatga
agaatttcgtgaaaacaacatagaaattgtgaccagattttatttagcatttcaaagtgtacataaatatattgtagacttaaaca
gatatctagatgatctcaatgaaggggtttatattcagcaaaccttagaaactgtgcttctcaatgaagatggaaaacaacttct
atgtgaagcactgtacttatatggagttatgctactggtcattgaccaaaagattgaaggagaagtcagagagaggatgctg
gtttcttactaccgatacagtgctgctcgatcttctgctgattcaaatatggacgatatttgtaagctgcttcgaagtacaggttat
tctagccaaccaggtgccaaaagaccatccaactatcccgagagctatttccagagagtgcctatcaacgaatccttcatca
gtatggtcattggtcgactgagatctgatgatatttacaaccaggtctcagcgtatcctttgccggagcatcgcagcacagcc
ctggcaaaccaagctgccatgctgtacgtgattctctactttgagccttccatccttcacacccatcaagcaaaaatgagaga
gatagtggataaatactttccagataattgggtaattagtatttacatggggatcacagttaatctagtagatgcttgggaaccttc
acaaagctgcaaaaactgctttaaataataccctggaccttcaaatgtcagagaacaggcaagcagatatgctactgtcagt
gaaagagtgcatgctcaagtgcagcaatttctaaaagaaggttatttaagggaggagatggttctggacaatatcccaaagc
ttctgaactgcctgagagactgcaatgttgccatccgatggctgatgcttcatacagcagactcagcctgtgacccaaacaa
caaacgccttcgtcaaatcaaggaccagattctaacagactctcggtacaatcccaggatcctcttccagctgctgttagata
ctgcacaatttgagtttatactcaaagagatgttcaagcaaatgcttcagaaaagcaaaccaaatgggagcattacaagaaa
gagggttcggagcggatgactgagcttgctgatgtcttttcaggagtgaaaccccctaaccagagtggagaaaaatgaaaac
cttcaagcttggttcagagagatctcaaaacaaatattgtctttaaattatgatgattctactgctgcgggcagaaaaactgtac
aactgatacaagctttggaagaggttcaagaattccaccagttggaatccaatctgcaagtatgtcagtttcttgccgatactc
gaaagtttcttcatcaaatgatcagaaccattaacattaaagaggaggttctgatcacaatgcagatcgttggggacctttcttt
cgcttggcagttgattgacagtttcacatccatcatgcaagaaagcataagggtaaatccatccatggttactaaactcagag
ctaccttcctaaagcttgcctctgccctcgatctgccccttcttcgtattaatcaggcaaatagccccgacctgctcagcgtgtc
acagtactattctggagagttcgtatcctatgtgagaaaagttttgcagatcatcccagaaagcatgtttacatctcttctaaaga
tcataaagcttcagacccacgacattattgaagtgcctacccgcctggacaaagacaagctgagggactatgctcagctag
gcccacgatacgaggttgccaagcttactcatgctatttccatttttactgaaggcatcttaatgatgaaaacgactttggttgg
catcatcaaggtggatccaaagcagttgctggaagatggaataaggaaagagcttgtgaagcgcgttgcctttgccctgcat
aggggactgatattcaaccctcgagccaagccaagtgaattgatgcccaagctgaaagagttgggagcgaccatggatgg
attccatcgttcttttgaatacatacaggactatgtcaacatttatggtctgaagatttggcaggaagaagtatctcgtatcataa
attacaacgtggagcaagagtgtaataactttctaagaacgaagattcaagattggcaaagcatgtaccagtccactcatatt
ccaatacccaagtttacccctgtggatgagtctgtaacgtttattggtcgactctgcagagaaatcctgcggatcacagaccc
aaaaatgacatgtcacatagaccagctgaacacttggtatgatatgaaaactcatcaggaagtgaccagcagccgcctcttc
tcagaaatccagaccaccttgggaaccttggtctaaatggcttagacaggcttctgtgctttatgattgtaaaagagttacag
aatttcctcagtatgtttcagaaaattatcctgagagacagaactgttcaggacacttaaaaaccctcatgaatgctgtcagtc
ccctaaaaagtattgtcgcaaattcaaataaaaatttattttccgccattgccaaaacacagaagatttggactgcgtatctcga
ggctataatgaaggttgggcagatgcagattctgagacaacagattgccaatgaattaaattattcttgtcggtttgattctaaa
catctggcagctgctctggagaatctcaataaggctctcctagcagacattgaagcccactatcaggacccttcacttcctta
ccccaaagaagataacacacttttatatgaaatcacagcctatctgg

Figure 12 aggcagctggcattcacaacccactgaataagatatacataacaacaaagcgcttaccctattttccaattgtaaactttctattt
ttgatcgctcagttgccaaaacttcaatacaacaaaaatctgggaatggtctgccgaaaaccgaccgacccggttgattggc
caccacttgtcctgggactgctcactctgctgaagcagttccattcccggtacaccgagcagttcctggcgctgattggcca
gtttatctgctccacggtggagcagtgtacaagccagaagatacctgaaattcctgcagatgttgtgggtgcccttctgttcct
ggaggattatgttcggtacacaaagctacccaggagggttgctgaagcacatgtgcctaatttcattttgatgagttcagaac
agtgctgtaactgttttcctacttcttcaatggaaggattgtccttagatcttcccaccatcacaaatgaatttgaagatgaaaa
gaaactcagttgctcatacaactgcattttttctgtctattatgggaaacatcagacgttctgagtaagatatatctcatggcatta
gttaatataactgatattgtttaaatcatggtattacatgcaatttatatcagataaaagcagaacacattttttgtactgcctctctta
aatgctgaatgtaactgttatgtataaatccatttagttttatgttctaaagaactatttgtgcaactccagattttcagtaaaatagt
attactagtacccaaaaaaaaaa (SEQ ID NO: 22)

Figure 12 (Continued)

KIAA0196 L619F mutant protein sequence mldflaennlcgqailrivscgnaiiaellrlsefipavfrlkdradqqkygdiifdfsyfkgpclweskldakpelqdlde
efrennieivtrfylafqsvhkyivdlnrylddlnegvyiqqtletvllnedgkqllcealylygvmllvidqkiegevrer
mlvsyyrysaarssadsnmddickllrstgyssqpgakrpsnypesyfqrvpinesfismvigrlrsddiynqvsaypl
pehrstalanqaamlyvilyfepsilhthqakmreivdkyfpdnwvisiymgitvnlvdawepykaaktalnntldls
nvreqasryatvservhaqvqqflkegylreemvldnipkllnclrdcnvairwlmlhtadsacdpnnkrlrqikdqilt
dsrynprilfqllldtaqfefilkemfkqmlsekqtkwehykkegsermteladvfsgvkpltrveknenlqawfreisk
qilslnyddstaagrktvqliqaleevqefhqlesnlqvcqfladtrkflhqmirtinikeevlitmqivgdlsfawqlidsf
tsimqesirvnpsmvtklratflklasaldlpllrinqanspdllsvsqyysgefvsyvrkvlqiipesmftsllkiiklqthd
iievptrldkdklrdyaqlgpryevaklthaisiftegilmmkttlvgiikvdpkqlledgirkelvkrvafalhrglifnpra
kpselmpklkelgatmdgfhrsfeyiqdyvniyglkiwqeevsriinynveqecnnflrtkiqdwqsmyqsthipip
kftpvdesvtfigrlcreilritdpkmtchidqlntwydmkthqevtssrlfseiqttlgtfglngldrllcfmivkelqnfls
mfqkiilrdrtvqdtlktlmnavsplksivansnkiyfsaiaktqkiwtayleaimkvgqmqilrqqianelnyscrfds
khlaaalenlnkalladieahyqdpslpypkedntllyeitayleaagihnplnkiyittkrlpyfpivnflfliaqlpklqyn
knlgmvcrkptdpvdwpplvlglltllkqfhsryteqflaligqficstveqctsqkipeipadvvgallfledyvrytklp
rrvaeahvpnfifdefrtvl (SEQ ID NO: 23)

Figure 13

KIAA0196 V626F (c.2205g>t) nucleotide sequence acatgatgcccctccctgctcccagccgcttcggtcatgtgaccgcctggggagtcaggggcggaagtcggggtctgacc
cgctccaggtccgggactgcggatagaagaggaccgccgccttgagggaggggtggaaactgggtgccggctccgcg
cgcgacctccggccctgcgcgtgcgccgtggcgcggcccggctgacaggttctttaatggaggagccaatctctctgcac
acctggtttcatctaataatatacagacaccagctctgaggccagttaatcatccccagtgtccaggcacagagtagtcggtc
cgcctcacaatgttggactttctagccgagaacaacctctgtggccaagcaatcctaaggattgtttcctgtggtaatgccatc
attgctgaacttttgagactctctgagtttattcctgctgtgttcaggttaaaagacagagctgatcaacagaaatatggagatat
catatttgatttcagctattttaagggtccagaattatgggaaagcaaactggatgctaagccagagctacaggatttagatga
agaatttcgtgaaaacaacatagaaattgtgaccagatttatttagcatttcaaagtgtacataaatatattgtagacttaaaca
gatatctagatgatctcaatgaaggggtttatattcagcaaaccttagaaactgtgcttctcaatgaagatggaaaacaacttct
atgtgaagcactgtacttatatggagttatgctactggtcattgaccaaaagattgaaggagaagtcagagagaggatgctg
gtttcttactaccgatacagtgctgctcgatcttctgctgattcaaatatggacgatatttgtaagctgcttcgaagtacaggttat
tctagccaaccaggtgccaaaagaccatccaactatcccgagagctatttccagagagtgcctatcaacgaatccttcatca
gtatggtcattggtcgactgagatctgatgatatttacaaccaggtctcagcgtatcctttgccggagcatcgcagcacagcc
ctggcaaaccaagctgccatgctgtacgtgattctctactttgagccttccatccttcacacccatcaagcaaaaatgagaga
gatagtggataaatactttccagataattgggtaattagtatttacatggggatcacagttaatctagtagatgcttgggaacctt
acaaagctgcaaaaactgctttaaataatacccctggaccttcaaatgtcagagaacaggcaagcagatatgctactgtcagt
gaaagagtgcatgctcaagtgcagcaatttctaaaagaaggttatttaaggggaggagatggttctggacaatatcccaaagc
ttctgaactgcctgagagactgcaatgttgccatccgatggctgatgcttcatacagcagactcagcctgtgacccaaacaa
caaacgccttcgtcaaatcaaggaccagattctaacagactctcggtacaatcccaggatcctcttccagctgctgttagata
ctgcacaatttgagtttatactcaaagagatgttcaagcaaatgctttcagaaaagcaaaccaaatgggagcattacaagaaa
gagggttcggagcggatgactgagcttgctgatgtcttttcaggagtgaaaccccctaaccagagtggagaaaaatgaaaac
cttcaagcttggttcagagagatctcaaaacaaatattgtctttaaattatgatgattctactgctgcgggcagaaaaactgtac
aactgatacaagctttggaagaggttcaagaattccaccagttggaatccaatctgcaagtatgtcagtttcttgccgatactc
gaaagtttcttcatcaaatgatcagaaccattaacattaaagaggaggttctgatcacaatgcagatcgttggggacctttcttt
cgcttggcagttgattgacagtttcacatccatcatgcaagaaagcataagggtaaatccatccatggttactaaactcagag
ctaccttcctaaagcttgcctctgccctcgatctgccccttcttcgtattaatcaggcaaatagccccgacctgctcagcgtgtc
acagtactattctggagagttggtatcctatgtgagaaaattttttgcagatcatcccagaaagcatgtttacatctcttctaaaga
tcataaagcttcagacccacgacattattgaagtgcctacccgcctggacaaagacaagctgagggactatgctcagctag
gcccacgatacgaggttgccaagcttactcatgctatttccattttactgaaggcatcttaatgatgaaaacgactttggttgg
catcatcaaggtggatccaaagcagttgctggaagatggaataaggaaagagcttgtgaagcgcgttgcctttgccctgcat
aggggactgatattcaaccctcgagccaagccaagtgaattgatgcccaagctgaaagagttgggagcgaccatggatgg
attccatcgttcttttgaatacatacaggactatgtcaacatttatggtctgaagatttggcaggaagaagtatctcgtatcataa
attacaacgtggagcaagagtgtaataactttctaagaacgaagattcaagattggcaaagcatgtaccagtccactcatatt
ccaatacccaagtttacccctgtggatgagtctgtaacgtttattggtcgactctgcagagaaatcctgcggatcacagaccc
aaaaatgacatgtcacatagaccagctgaacacttggtatgatatgaaaactcatcaggaagtgaccagcagccgcctcttc
tcagaaatccagaccaccttgggaacctttggtctaaatggcttagacaggcttctgtgctttatgattgtaaaagagttacag
aatttcctcagtatgtttcagaaaattatcctgagagacagaactgttcaggacactttaaaaaccctcatgaatgctgtcagtc
ccctaaaaagtattgtcgcaaattcaaataaaatttattttttccgccattgccaaaacacagaagatttggactgcgtatctcga
ggctataatgaaggttgggcagatgcagattctgagacaacagattgccaatgaattaaattattcttgtcggtttgattctaaa
catctggcagctgctctggagaatctcaataaggctctcctagcagacattgaagcccactatcaggacccttcacttcctta
ccccaaagaagataacacacttttatatgaaatcacagcctatctgg

Figure 14 aggcagctggcattcacaacccactgaataagatatacataacaacaaagcgcttaccctatttccaattgtaaactttctattt
ttgatcgctcagttgccaaaacttcaatacaacaaaaatctgggaatggtctgccgaaaaccgaccgacccggttgattggc
caccacttgtcctgggactgctcactctgctgaagcagttccattcccggtacaccgagcagttcctggcgctgattggcca
gtttatctgctccacggtggagcagtgtacaagccagaagatacctgaaattcctgcagatgttgtgggtgcccttctgttcct
ggaggattatgttcggtacacaaagctacccaggagggttgctgaagcacatgtgcctaatttcattttgatgagttcagaac
agtgctgtaactgttttcctacttcttcaatggaaggattgtccttagatcttcccaccatcacaaatgaatttgaagatgaaaa
gaaactcagttgctcatacaactgcatttttctgtctattatgggaaacatcagacgttctgagtaagatatatctcatggcatta
gttaatataactgatattgtttaaatcatggtattacatgcaatttatatcagataaaagcagaacacattttgtactgcctctctta
aatgctgaatgtaactgttatgtataaatccatttagttttatgttctaaagaactatttgtgcaactccagatttcagtaaaatagt
attactagtacccaaaaaaaaaaa (SEQ ID NO: 24)

Figure 14 (Continued)

KIAA0196 V626F mutant protein sequence mldflaennlcgqailrivscgnaiiaellrlsefipavfrlkdradqqkygdiifdfsyfkgpelweskldakpelqdlde
efrennieivtrfylafqsvhkyivdlnrylddlnegvyiqqtletvllnedgkqllccalylygvmllvidqkiegevrer
mlvsyyrysaarssadsnmddickllrstgyssqpgakrpsnypesyfqrvpinesfismvigrlrsddiynqvsaypl
pchrstalanqaamlyvilyfcpsilhthqakmreivdkyfpdnwvisiymgitvnlvdawepykaaktalnntldls
nvreqasryatvservhaqvqqflkegylreemvldnipkllnclrdcnvairwlmlhtadsacdpnnkrlrqikdqilt
dsrynprilfqllldtaqfefilkemfkqmlsekqtkwehykkegsermteladvfsgvkpltrveknenlqawfreisk
qilslnyddstaagrktvqliqaleevqefhqlesnlqvcqfladtrkflhqmirtinikeevlitmqivgdlsfawqlidsf
tsimqesirvnpsmvtklratflklasaldlpllrinqanspdllsvsqyysgelvsyvrkflqiipesmftsllkiiklqthdi
ievptrldkdklrdyaqlgpryevaklthaisiftegilmmkttlvgiikvdpkqlledgirkelvkrvafalhrglifnpra
kpselmpklkelgatmdgfhrsfeyiqdyvniyglkiwqeevsriinynveqecnnflrtkiqdwqsmyqsthipip
kftpvdesvtfigrlcreilritdpkmtchidqlntwydmkthqevtssrlfseiqttlgtfglngldrllcfmivkelqnfls
mfqkiilrdrtvqdtlktlmnavsplksivansnkiyfsaiaktqkiwtayleaimkvgqmqilrqqianelnyscrfds
khlaaalenlnkalladieahyqdpslpypkedntllyeitayleaagihnplnkiyittkrlpyfpivnflfliaqlpklqyn
knlgmvcrkptdpvdwpplvlglltlllkqfhsryteqflaligqficstveqctsqkipeipadvvgallfledyvrytklp
rrvaeahvpnfifdefrtvl (SEQ ID NO: 25)

Figure 15

```
  1  - - - - - - - - - - - - - - - - - - - - - - - - - - - - - -   human KIAA0196
  1  - - - - - - - - - - - - - - - - - - - - - - - - - - - - - -   orangutan KIAA0196
  1  - - - - - - - - - - - - - - - - - - - - - - - - - - - - - -   mouse KIAA0196
  1  - - - - - - - - - - - - - - - - - - - - - - - - - - - - - -   rat KIAA0196
  1  M E R R R L G E G A A C P S L R A R R A E P G P Q P G R T D   dog KIAA0196
  1  - - - - - - - - - - - - - - - - - - - - - - - - - - - - - -   fowl KIAA0196
  1  - - - - - - - - - - - - - - - - - - - - - - - - - - - - - -   frog KIAA0196
  1  - - - - - - - - - - - - - - - - - - - - - - - - - - - - - -   fruit fly KIAA0196
  1  - - - - - - - - - - - - - - - - - - - - - - - - - - - - - -   zebrafish KIAA0196
  1  - - - - - - - - - - - - - - - - - - - - - - - - - - - - - -   C elegans KIAA0196
  1  - - - - - - - - - - - - - - - - - - - - - - - - - - - - - -   amoeba KIAA0196

1  - - - - - - - - - - - - - - - - - - - - - - - - - - - - - -   human KIAA0196
  1  - - - - - - - - - - - - - - - - - - - - - - - - - - - - - -   orangutan KIAA0196
  1  - - - - - - - - - - - - - - - - - - - - - - - - - - - - - -   mouse KIAA0196
  1  - - - - - - - - - - - - - - - - - - - - - - - - - - - - - -   rat KIAA0196
 31  P S S G H P R G A P R G G D T C R H P R P R H P P L P P Y L   dog KIAA0196
  1  - - - - - - - - - - - - - - - - - - - - - - - - - - - - - -   fowl KIAA0196
  1  - - - - - - - - - - - - - - - - - - - - - - - - - - - - - -   frog KIAA0196
  1  - - - - - - - - - - - - - - - - - - - - - - - - - - - - - -   fruit fly KIAA0196
  1  - - - - - - - - - - - - - - - - - - - - - - - - - - - - - -   zebrafish KIAA0196
  1  - - - - - - - - - - - - - - - - - - - - - - - - - - - - - -   C elegans KIAA0196
  1  - - - - - - - - - - - - - - - - - - - - - - - - - - - - - -   amoeba KIAA0196

1

1  - - - - - - - - - - - - - - - - - - - M L D F L - - - - -   human KIAA0196
  1  - - - - - - - - - - - - - - - - - - - M L D F L - - - - -   orangutan KIAA0196
  1  - - - - - - - - - - - - - - - - - - - M L D F L - - - - -   mouse KIAA0196
  1  - - - - - - - - - - - - - - - - - - - - - - - - - - - - -   rat KIAA0196
 61  E A R P G S V W Q H P D R P R P D P N S F L N S L P Q S L K   dog KIAA0196
  1  - - - - - - - - - - - - - - - - - - - M V D F L - - - - -   fowl KIAA0196
  1  - - - - - - - - - - - - - - - - - - - M V D F L - - - - -   frog KIAA0196
  1  - - - - - - - - - - - - - - - - - - - - M S F L D - - - -   fruit fly KIAA0196
  1  - - - - - - - - - - - - - - - - - - - M V D F L - - - - -   zebrafish KIAA0196
  1  - - - - - - - - - - - - - - - - - - - - - - - - - - - - -   C elegans KIAA0196
  1  - - - - - - - - - - - - - - - - - - - M V K E F L G - - -   amoeba KIAA0196

6  - - - - - - - - - - - - - - - - - - - - - - - - - - - - - -   human KIAA0196
  6  - - - - - - - - - - - - - - - - - - - - - - - - - - - - - -   orangutan KIAA0196
  6  - - - - - - - - - - - - - - - - - - - - - - - - - - - - - -   mouse KIAA0196
  1  - - - - - - - - - - - - - - - - - - - - - - - - - - - - - -   rat KIAA0196
 91  P R A R A R A S S A V A G Q R S H D A P P C S R P L W S C D   dog KIAA0196
  6  - - - - - - - - - - - - - - - - - - - - - - - - - - - - - -   fowl KIAA0196
  6  - - - - - - - - - - - - - - - - - - - - - - - - - - - - - -   frog KIAA0196
  6  - - - - - - - - - - - - - - - - - - - - - - - - - - - - - -   fruit fly KIAA0196
  6  - - - - - - - - - - - - - - - - - - - - - - - - - - - - - -   zebrafish KIAA0196
  1  - - - - - - - - - - - - - - - - - - - - - - - - - - - - - -   C elegans KIAA0196
  8  - - - - - - - - - - - - - - - - - - - - - - - - - - - - - -   amoeba KIAA0196
```

Figure 16

```
                                                    ---------+---
                                                            10
                                                    ---------+---
  6  - - - - - - - - - - - - - - - - - - - - - - - - A E N N L C   human KIAA0196
  6  - - - - - - - - - - - - - - - - - - - - - - - - A E N N L C   orangutan KIAA0196
  6  - - - - - - - - - - - - - - - - - - - - - - - - A E N N L C   mouse KIAA0196
  1  - - - - - - - - - - - - - - - - - - - - - - - - - - - - -     rat KIAA0196
121  C H G R H R R K P G S R R L A I G G C G R R G R P E N N L C   dog KIAA0196
  6  - - - - - - - - - - - - - - - - - - - - - - - - A E N N L C   fowl KIAA0196
  6  - - - - - - - - - - - - - - - - - - - - - - - - A E N N L C   frog KIAA0196
  6  - - - - - - - - - - - - - - - - - - - - - - - - D N N A C     fruit fly KIAA0196
  6  - - - - - - - - - - - - - - - - - - - - - - - - A E N N L C   zebrafish KIAA0196
  1  - - - - - - - - - - - - - - - - - - - - - - - - - M T E E I   C elegans KIAA0196
  8  - - - - - - - - - - - - - - - - - - - - - - - - - E G S Q A   amoeba KIAA0196

-------------------+-------------------+-------------------+---
                                20                  30                  40
              -------------------+-------------------+-------------------+---
 12  G Q A I L R I V S C G N A I I A E L L R L S E F I P A V F R   human KIAA0196
 12  G Q A I L R I V S C G N A I I A E L L R L S E F I P A V F R   orangutan KIAA0196
 12  G Q A I L R I V S C G N A I I A E V L R L S E F I P A V F L   mouse KIAA0196
  1  - - - - - - - - - - - - - - - - - - - - - - - - - - - -     rat KIAA0196
151  G Q A I L R I V S C G N A I I A E L L R L S E F I P A V F R   dog KIAA0196
 12  G Q A I L R I V S C G N A I I A E L L R L S E F I P G V F R   fowl KIAA0196
 12  G Q A I L R I V S R G N A I I A E L L R L S E F V P S V F R   frog KIAA0196
 11  G Q N L L N I V S V G N S I I A E I L R L K D Y V P S I Y R   fruit fly KIAA0196
 12  G Q A I L R I V S R G N A I I A E L L R L S D F I P A V F R   zebrafish KIAA0196
  6  N I F L S K L I L H G E S I L A E I F R L S S F I P K D F R   C elegans KIAA0196
 13  G Q N L L R L V S R G N A I I A E L L R L S A H I P S V F K   amoeba KIAA0196

-------------------+-------------------+-------------------+---
                                50                  60                  70
              -------------------+-------------------+-------------------+---
 42  L K D R A D Q Q K Y G D I I F D F S Y F K G P E L W E S K L   human KIAA0196
 42  L K D R A D Q Q K Y G D I I F D F S Y F K G P E L W E S K L   orangutan KIAA0196
 42  L K D R A D Q Q R Y G D I I F D F S Y F K G P E F W E S K L   mouse KIAA0196
  1  - - - - - - - - - - - - - - - - - - - - - - - - - - - -     rat KIAA0196
181  L K D R A D Q Q K Y G D I I F D F S Y F K G P E L W E S K L   dog KIAA0196
 42  L K D K A D Q Q K Y G D I I F D F S Y F K G P E A C E G R L   fowl KIAA0196
 42  L K D K A D Q Q K Y G D I I F D F S Y F K G P E V C E G R L   frog KIAA0196
 41  L D N K A D K A K Y G E L I L D F S Y F K I A E D H E R R I   fruit fly KIAA0196
 42  L R D K T D Q Q K Y G D I I C D F S Y F K G P E Y Y E G K L   zebrafish KIAA0196
 36  D P T K S S K F K N - I V Q L D F K Y L S K V D Q I E K E L   C elegans KIAA0196
 43  L E D R N E A R K Y Q D I L L D F K Y L S N P D F Y E S K I   amoeba KIAA0196

-------------------+-------------------+-------------------+---
                                80                  90                 100
              -------------------+-------------------+-------------------+---
 72  D A K P E L Q D L D E E F R E N N I E I V T R F Y L A F Q S   human KIAA0196
 72  D A K P E L Q D L D E E F R E N N I E I V T R F Y L A F Q S   orangutan KIAA0196
 72  E A K P E L Q D L D E E F R E N N I E I V T R F Y L A F Q S   mouse KIAA0196
  1  - - - - - - - - - - - - - - - - - - - - - - M S F K G         rat KIAA0196
211  E A K P E L Q D L D E E F R E N N I E I V T R F Y L A F Q S   dog KIAA0196
 72  E A K P E L L D L D E E F R E N N I E I L T R F Y L A F Q S   fowl KIAA0196
 72  E A K P E L Q D L D E E F R E N N I E I L T R F Y L A F E S   frog KIAA0196
 71  E Q S P E L T E L D D E A R - A Q L P L I T R F Y L A F Q S   fruit fly KIAA0196
 72  E A K P E L Q D L D E E F R E N N I E I L T R F Y L A F E S   zebrafish KIAA0196
 65  E S - - - H L R L Q T Q F Y S T F E P V L I A F E Q L F S S   C elegans KIAA0196
 73  E E N A D L V D L E T E F R D N H I D I L I R F Y H L F E S   amoeba KIAA0196
```

Figure 16 (Continued)

```
                    ----------------+--------------------+------------------+---
                                110                  120                130
                    ----------------+--------------------+------------------+---
    102  V H K Y I V D L N R Y L D D L N E G V Y I Q Q T L E T V L L   human KIAA0196
    102  V H K Y I V D L N R Y L D D L N E G V Y I Q Q T L E T V L L   orangutan KIAA0196
    102  V H K Y I V D L N R Y L D D L N E G V Y I Q Q T L E T V L L   mouse KIAA0196
      6  V R K I R V - - - - - - - - - - - - - - - - - - - - - - - -   rat KIAA0196
    241  V H K Y I V D L N R Y L D D L N E G V Y I Q Q T L E T V L L   dog KIAA0196
    102  V H K Y I I D L N - - - - - - - - - - - - - - - - - - - - -   fowl KIAA0196
    102  V H K Y I V D L N R Y L E D L N E G I Y I Q Q T L E T V L L   frog KIAA0196
    100  I H H Y A S D L Q Q Y I E E L N T G Y Y I Q Q T L E T V L Q   fruit fly KIAA0196
    102  V H K Y V V D L I R C L D D L N E G V Y I Q Q T L E T V L L   zebrafish KIAA0196
     92  I S E F V Q S F I S Y T - - - K E A E I I N G - - E T R M D   C elegans KIAA0196
    103  I Y K Y I M D L E H Y I V D V E K G F Y I H L T I E A I L I   amoeba KIAA0196

----------------+--------------------+------------------+---
                                140                  150                160
                    ----------------+--------------------+------------------+---
    132  N E D G K Q L L C E A L Y L Y G V M L L V I D Q K I E G E V   human KIAA0196
    132  N E D G K Q L L C E A L Y L Y G V M L L V I D Q K I E G E V   orangutan KIAA0196
    132  S E D G K Q L L C E A L Y L Y G V M L L V I D Q K I E G E V   mouse KIAA0196
     12  - - - G H F V F Y A D A - - - - - - - - - - - - - - - - - -   rat KIAA0196
    271  N E D G K Q L L C E A L Y L Y G V M L L V I D Q K I E G E V   dog KIAA0196
    111  - - - - - - - - - - - - - - - - - - - - - - - - - - - - -   fowl KIAA0196
    132  N E D G K Q L L C E A L Y L Y G V M L L V I D Q K I E G E V   frog KIAA0196
    130  E E E G R Q L L C E S L Y L F G V I L L M V D F H I P G D V   fruit fly KIAA0196
    132  N E D G K Q L L C E A L Y L Y G V M L L V I D Q K M E G E V   zebrafish KIAA0196
    117  V N R T S E L E A Y C L Y I S G I L I I Y M D T Y I P A P I   C elegans KIAA0196
    133  N G D G K Q L L S E A V Y L Y G V M L I L M D N L I E G P V   amoeba KIAA0196

----------------+----------      -----------+---    ---------------
                                170                          180
                    ----------------+----------      -----------+---    ---------------
    162  R E R M L V S Y Y R Y S A - - A R S S A D S - N M D D I C K   human KIAA0196
    162  R E R M L V S Y Y R Y S A - - A R S S A D S - N M D D I C K   orangutan KIAA0196
    162  R E R M L V S Y Y R Y S A - - A R S S A D S - N M D D I C K   mouse KIAA0196
     21  - - - - - - - - - - - - - - - - - - - - - - - - - - - - -   rat KIAA0196
    301  R E R M L V S Y Y R Y S A - - A R S S A D S - N M D D I C K   dog KIAA0196
    111  - - - - - - - - - - S A - - A R S S A D S - N L D D I C K   fowl KIAA0196
    162  R E R M L V A Y Y R Y S A - - A R S S V D S - N M D D I C K   frog KIAA0196
    160  R E R L L I A Y Y R Y S G G D A T P S G D E S N I H D V C L   fruit fly KIAA0196
    162  R E R M L V S Y Y R Y S A - - A R S S A D S - N L D D I C K   zebrafish KIAA0196
    147  R E R I Y I A I Y R - - - - - K S D V R E - N A E F L V D   C elegans KIAA0196
    163  R E R M L I S Y L R - - - - - N K G P V D L P L I D E V C K   amoeba KIAA0196

--+-----------------                      ----+----------
                                190                                200
                    --+-----------------                      ----+----------
    189  L L R S T G Y S S - - - - - - - - - - - - - Q P G A K R P -   human KIAA0196
    189  L L R S T G Y S S - - - - - - - - - - - - - Q P G A R R P -   orangutan KIAA0196
    189  L L R S T G Y S S - - - - - - - - - - - - - Q P G A K R P -   mouse KIAA0196
     21  - - - - - - - - - - - - - - - - - - - - - - - - - - - - -   rat KIAA0196
    328  L L R S T G Y S S - - - - - - - - - - - - - Q P G A K R P -   dog KIAA0196
    127  L L R S T G Y S S - - - - - - - - - - - - - Q P G A K R P -   fowl KIAA0196
    189  L L R S T G Y S S - - - - - - - - - - - - - Q P G A K R P -   frog KIAA0196
    190  L L R S T G Y V H P S I A A K V L G L G G K Q A G A R A A S   fruit fly KIAA0196
    189  L L R S T G Y S S - - - - - - - - - - - - - H P G A K R P -   zebrafish KIAA0196
    170  F L K A T - - - - - - - - - - - - - - - - - V P G - - - - -   C elegans KIAA0196
    188  L C K S T G Y I P - - - - - - - - - - - - - G S - P K K P -   amoeba KIAA0196
```

Figure 16 (Continued)

```
                    ----------+--------------------+--------------------+---
                         210                  220                  230
                    ----------+--------------------+--------------------+---
205  - - - S N Y P E S Y F Q R V P I N E S F I S M V I G R L R S    human KIAA0196
205  - - - P N Y P E S Y F Q R V P I N E S F I S M V I G R L R S    orangutan KIAA0196
205  - - - P N Y P E S Y F Q R V P I N E T F I S M V I G R L R S    mouse KIAA0196
 21  - - - - - - - - - - - - - - - G - - - - - - - - Q I L S       rat KIAA0196
344  - - - P N Y P E S Y F Q R V P I N E A F I S M V I G R L R S    dog KIAA0196
143  - - - P N Y P E S Y F S R V P I S E T F I S M V V G R L R S    fowl KIAA0196
205  - - - P N Y P E S Y F S R V P I S E T F I S M V I G R L R S    frog KIAA0196
220  L V V P R Y P E A Y F S R F R F D E N F V D L V V A R L R C    fruit fly KIAA0196
205  - - - T N Y P E S Y F Q R V P I S S T F I S M V I G R L R S    zebrafish KIAA0196
178  - - - - N - - D S M I R R I P L P E S F I T - - - S T I N A    C elegans KIAA0196
203  - - - P N Y P E E Y F R R V E L P E N V I S M I V G R L R S    amoeba KIAA0196

----------+--------------------+--------------------+---
                         240                  250                  260
                    ----------+--------------------+--------------------+---
232  D D I Y N Q V S A Y P L P E H R S T A L A N Q A A M L Y V I    human KIAA0196
232  D D I Y N Q V S A Y P L P E H R S T A L A N Q A A M L Y V I    orangutan KIAA0196
232  D D I Y N Q V S A Y P L P E H R S T A L A N Q A A M L Y V I    mouse KIAA0196
 26  D S L L S Q V - - - - - - - - - - - - - - - - - - - - -       rat KIAA0196
371  D D I Y N Q V S A Y P L P E H R S T A L A T Q A A M L Y V I    dog KIAA0196
170  D D I Y N Q V S A Y P L P E H R S T A L A T Q A A M L Y V I    fowl KIAA0196
232  D D I Y N Q V S A Y P L P E H R S T A L A T Q A A I L Y V I    frog KIAA0196
250  D D I Y N Q L N L Y P H P A H R S T A L S T Q A A M L Y V C    fruit fly KIAA0196
232  D D I Y N Q V S A Y P L P E H R S T A L A T Q A A M L Y V C    zebrafish KIAA0196
199  I E I I E G T S - L Q I P - - - - - - - - K A Q L M Y V A      C elegans KIAA0196
230  D D L Y N G T E S F P Q P E H R S V A L S T Q A C M I Y V I    amoeba KIAA0196

----------+--------------------+--------------------+---
                         270                  280                  290
                    ----------+--------------------+--------------------+---
262  L Y F E P S I L H T H Q A K M R E I V D K Y F P D N W V I S    human KIAA0196
262  L Y F E P S I L H T H Q A K M R E I V D K Y F P D N W V I S    orangutan KIAA0196
262  L Y F E P S I L H T H Q A K M R E I V D K Y F P D N W V I S    mouse KIAA0196
 33  - - - - - - - - - - - - - - - - - - - - - - - - I S           rat KIAA0196
401  L Y F E P S I L H T H Q A K M R E I V D K Y F P D N W V I S    dog KIAA0196
200  L Y F D A S I L H T Q Q A K M R E I V D K Y F P D N W V I S    fowl KIAA0196
262  L Y F H P P T L H T H Q A K M R E I V D K Y F P D N W V I S    frog KIAA0196
280  L Y F C P Q V L H S Q G S Q M R E I V D K F F C D N W T I S    fruit fly KIAA0196
262  L Y F T P S I L H T Q Q A K M R E I V D K Y F P D N W V I S    zebrafish KIAA0196
219  L Q F D R Q T L T N D S A I M T K I A N S I Y R E T W V I N    C elegans KIAA0196
260  L Y F I P D I L N N K N S I M R E I V D K F F P D N W V I S    amoeba KIAA0196

----------+--------------------+--------------------+---
                         300                  310                  320
                    ----------+--------------------+--------------------+---
292  I Y M G I T V N L V D A W E P Y K A A K T A L N N T L D L S    human KIAA0196
292  I Y M G I T V N L V D A W E P Y K A A K T A L N N T L D L S    orangutan KIAA0196
292  I Y M G I T V N L A D A W E P Y K A A K T A L N N T L D L A    mouse KIAA0196
 35  I Y M G I T V N L A D A W E P Y K A A K T A L N N T L D L P    rat KIAA0196
431  I Y M G I T V N L A D A W E P Y K A A K T A L N N T L D L S    dog KIAA0196
230  I Y M G I T V N L A E A W E P Y K A A K T A L N Y T L D I A    fowl KIAA0196
292  I Y M G I T V N L M E V W E P Y K A A K T A L N Y T L D L P    frog KIAA0196
310  V Y M G M T V N L V D A W L D F K A A R S A I E N V I S P P    fruit fly KIAA0196
292  I Y M G I T V N L V E A W E P Y K A A K I A L N Y T L D T A    zebrafish KIAA0196
249  L G F G V I A N V F D G W Y N F K S A W N A I N S T I T Q Q    C elegans KIAA0196
290  F F L G F T I D L S V A W E P Y K A A K T A M G N T I I Q S    amoeba KIAA0196
```

Figure 16 (Continued)

```
               ----------------+--------------------+-----------------+---
                              330                  340               350
               ----------------+--------------------+-----------------+---
322   N V R E Q A S R Y A T V S E R V H A Q V Q Q F L K E G Y L R    human KIAA0196
322   N V R E Q A S R Y A T V S E R V H A Q V Q Q F L K E G Y L R    orangutan KIAA0196
322   N V K E Q A S R Y A S V S D R V R A Q V Q Q F L K E G Y L R    mouse KIAA0196
 65   N V K E Q A S R Y A S V S E R V R A Q V Q Q F L K E G Y L R    rat KIAA0196
461   N V R E Q S S R Y A T V S E R V H A Q V Q Q F L K E G Y L R    dog KIAA0196
260   N V K E Q A N R Y A A V T E R V H T Q V Q Q F L K E G C L R    fowl KIAA0196
322   N I K E Q A S R Y A K I I E S L H P Q V Q Q F L K E G F L R    frog KIAA0196
340   A I K A L C Q Q Q K E Q L G K I T Q K T Q E I V R E G V L N    fruit fly KIAA0196
322   N I R E Q A G R Y A A S V E T L R P Q V Q Q L L K E G F L R    zebrafish KIAA0196
279   D A Q R I M E K H L K M M N - - E T S F P Q V I N E - - - -    C elegans KIAA0196
320   N I Q Y Q T Q R F W K E V S E L N K L V D D L L V D G L L V    amoeba KIAA0196

----------------+--------------------+-----------------+---
                              360                  370               380
               ----------------+--------------------+-----------------+---
352   E E M V L D N I P K L L N C L R D C N V A I R W L M L H T A    human KIAA0196
352   E E M V L D N I P K L L N C L R D C N V A I R W L M L H T A    orangutan KIAA0196
352   E E V L L D N I P K L L N C L R D C N V A I R W L M L H T A    mouse KIAA0196
 95   E E V L L D N I P R L L N C L R D C N V A I R W L M L H T A    rat KIAA0196
491   E E M V L D N I P R L L N C L R D C N V A I R W L M L H T A    dog KIAA0196
290   E E L V L D N I P K L L N Y L R D C N V A I R W L M L H T A    fowl KIAA0196
352   E E F V L D N I P K L L N C L R D C N V A I R W L M L H T A    frog KIAA0196
370   D N F V L E H A N K I I H L M R Q S N V L L R W F C L H T S    fruit fly KIAA0196
352   E E I I L D N I P K L L N C L R D C N V A I R W L M L H T A    zebrafish KIAA0196
303   - - - - M I D F E Q N L K K I S M C N R S L K W L F L H S K    C elegans KIAA0196
350   E E Y I V D N V H K I I T T L R R C N V T I R W V M L H S N    amoeba KIAA0196

----------------+--------------------+     ------
                              390                  400
               ----------------+--------------------+     ------
382   D S A C D P N N K R - - L R Q I K D Q I L T D S R Y - N P R    human KIAA0196
382   D S A C D P N N K R - - L R Q I K D Q I L T D S R Y - N P R    orangutan KIAA0196
382   D S A C D P N N K R - - L R Q I K D Q I L A D S R Y - N P K    mouse KIAA0196
125   D S A C D P N N K R - - L R Q I K D Q I L A D S R Y - N P K    rat KIAA0196
521   D S A C D P N N K R - - L R Q I K D Q I L T D S R Y - N P K    dog KIAA0196
320   D T A C D P N N K R - - L R Q I K D Q I L T D S R Y - N P K    fowl KIAA0196
382   D S A Y D P N N K R - - L R Q V K D Q V L A D S K Y - N P K    frog KIAA0196
400   R E V F I F A H T A T L T G Q V Q K C V L H E L Q F - N R N    fruit fly KIAA0196
382   E S A Y D P N N K R - - L R Q I K D Q V I N D S K Y - N P K    zebrafish KIAA0196
329   I S - - - - - - - - - - - Q K T S R P L N K Y R L P S D D    C elegans KIAA0196
380   A S - - - - - - Q - - - - K K F K D L V L M G G - - - S Q E    amoeba KIAA0196

--+--------------------+--------------------+------------------
                 410                  420                  430
               --+--------------------+--------------------+------------------
409   I L F Q L L L D T A Q F E F I L K E M F K Q M L S E K Q T K    human KIAA0196
409   I L F Q L L L D T A Q F E F I L K E M F K Q M L S E K Q T K    orangutan KIAA0196
409   I L F Q L L L D T A Q F E F I L K E M F K Q M L S E K Q S K    mouse KIAA0196
152   I L F Q L L L D T A Q F E F I L K E M F K Q M L S E K Q S K    rat KIAA0196
548   I L F Q L L L D T A Q F E F I L K E M F K Q M L S E K Q A K    dog KIAA0196
347   V L F Q L L L D T A Q F E F I L K E M F K Q M L S E K Q A K    fowl KIAA0196
409   I L F Q L L L D T A Q F E F L L K E M F K Q M L S E K Q N K    frog KIAA0196
429   T L Y N L L L N C S Q M E L S V R E F L A E I Q Q T K E E R    fruit fly KIAA0196
409   I L F Q L L L D T A Q F E F I L K E M F K Q M L A E K Q L K    zebrafish KIAA0196
347   Q L F Q W L L H V S R C E I L L L N L Y T T T L E N R D V E    C elegans KIAA0196
397   D V L Y L L L N T A Q L E F V F K N I F Q Q L L A T K E E K    amoeba KIAA0196
```

Figure 16 (Continued)

```
            --+--------------+--------------------+-------------------
              440              450                  460
            --+--------------+--------------------+-------------------
        439   W E H Y K K E G S E R M T E L A D V F S G V K P L T R V E K   human KIAA0196
        439   W E H Y K K E G S E R M T E L A D V F S G V K P L T R V E K   orangutan KIAA0196
        439   W E H Y K K E G S E R M T E L A D V F S G V K P L T R V E K   mouse KIAA0196
        182   W E H Y K K E G S E R M T E L A D V F S G V K P L T R V E K   rat KIAA0196
        578   W E H Y K K E S S E R M T E L A D V F S G V K P L T R V E K   dog KIAA0196
        377   W E N Y K K E G S E R M T E L A D V F S G V K P L T R V E K   fowl KIAA0196
        439   W E S Y K K E G S E R M T E L A D V F S G V K P L T R V E K   frog KIAA0196
        459   W T K S R E E A M Q R L N E L S E A F A G S R P L S K I E Q   fruit fly KIAA0196
        439   W E S Y K K E G S E R M M E L A E V F S G V K P L T R V E K   zebrafish KIAA0196
        377   G T E R K Q N I R T L L H Q L A E F F E H G F V K M G E S Q   C elegans KIAA0196
        427   W E E N K K L A S D S M V E L S E Y F S G E K A L T R V K K   amoeba KIAA0196

--                                    +---------------
                                                      470
              --                                    +---------------
        469   N - - - - - - - - - - - - - - - - - - - E N L Q A W F   human KIAA0196
        469   N - - - - - - - - - - - - - - - - - - - E N L Q A W F   orangutan KIAA0196
        469   N - - - - - - - - - - - - - - - - - - - E N L Q A W F   mouse KIAA0196
        212   N - - - - - - - - - - - - - - - - - - - E N L Q A W F   rat KIAA0196
        608   N G N C R R R N I G V L E M Y T Q I T G K Q Q K N L Q A W F   dog KIAA0196
        407   N - - - - - - - - - - - - - - - - - - - E N L Q A W F   fowl KIAA0196
        469   N - - - - - - - - - - - - - - - - - - - E H L Q A W F   frog KIAA0196
        489   N - - - - - - - - - - - - - - - - - - - P Q L Q Q W F   fruit fly KIAA0196
        469   N - - - - - - - - - - - - - - - - - - - E N L Q A W F   zebrafish KIAA0196
        407   K - - - - - - - - - - - - - - - - - - - T N F V K W V   C elegans KIAA0196
        457   N - - - - - - - - - - - - - - - - - - - E N L Q K W F   amoeba KIAA0196

------+--------------+--------------------+---------------
                  480              490                  500
            ------+--------------+--------------------+---------------
        477   R E I S K Q I L S L N Y D D S T A A G R K T V Q L I Q A L E   human KIAA0196
        477   R E I S K Q I L S L N Y D D S T A A G R K T V Q L I Q A L E   orangutan KIAA0196
        477   R E I S K Q I L S L N Y D D S T A A G R K T V Q L I Q A L E   mouse KIAA0196
        220   R E I S K Q I L S L N Y D D S T A A G R K T V Q L I Q A L E   rat KIAA0196
        638   R E I S K Q I L S L N H D D S T A A G R K T V Q L I Q A L E   dog KIAA0196
        415   R E I S K Q I M S L N Y D D S T A A G R K T V Q L I Q A L E   fowl KIAA0196
        477   R E I A K Q I H S L N Y D D S T A A G R K T V Q L I Q A L E   frog KIAA0196
        497   G E V A G R L Q K L E L S R P Q K S G R L I I Q V M Q A L D   fruit fly KIAA0196
        477   R E I S K Q I E S L N Y E D S T A A G R K T V Q L I Q A L V   zebrafish KIAA0196
        415   R N L S E T V E K I D L N D T T E S V E T I Q Q I I R R V K   C elegans KIAA0196
        465   G E I S Q K I S Q L D S T D S T S G R K I Q Q L S L A L E   amoeba KIAA0196

------+--------------+--------------------+---------------
                    510              520                  530
              ------+--------------+--------------------+---------------
        507   E V Q E F H Q L E S N L Q V C Q F L A D T R K F L H Q M I R   human KIAA0196
        507   E V Q E F H Q L E S N L Q V C Q F L A D T R K F L H Q M I R   orangutan KIAA0196
        507   E V Q E F H Q L E S N L Q V C Q F L A D T R K F L H Q M I R   mouse KIAA0196
        250   E V Q E F H Q L E S N L Q V C Q F L A D T R K F L H Q M I R   rat KIAA0196
        668   E V Q E F H Q L E S N L Q V C Q F L A D T R K F L H Q M I R   dog KIAA0196
        445   E V Q E F H Q L E S N L Q V C Q F L A D T R K F L H Q M I R   fowl KIAA0196
        507   E V Q E F H Q L E T N L Q V C Q F L A D T R K F L H Q M I R   frog KIAA0196
        527   D V Q E Y H N L H S N M L V X Q Q L Q E T R D M L N Q M A Q   fruit fly KIAA0196
        507   E V Q E F H Q L E S N L Q V C Q F L A D T R K F L H Q M I R   zebrafish KIAA0196
        445   Q V G D Q L G L S I N L T L K D C L S T L D T D L R A L M S   C elegans KIAA0196
        495   E V E Q F Q Q I D S S I Q V K Q F L I E T R Q F L T K M I K   amoeba KIAA0196
```

Figure 16 (Continued)

```
              ------+------------------+------------------+--------  ----
                 540                550                560
              ------+------------------+------------------+--------  ----
537   T I N I K E E V L I T M Q I V G D L S F A W Q L I D S - F T    human KIAA0196
537   T I N I K E E V L I T M Q I V G D L S F A W Q L I D S - F T    orangutan KIAA0196
537   T I N I K E E V L I T V Q I I G D L S F A W Q L I D S - F T    mouse KIAA0196
280   T I N I K E E V L I T M Q I V G D L S F A W Q L I D S - F T    rat KIAA0196
698   T I N I K E E V L I T M Q I V G D L S F A W Q L I D S - F T    dog KIAA0196
475   T I N I K E E V L I T M Q I V G D L S Y A W Q L I D S - F T    fowl KIAA0196
537   T I N I K E E V L I T M Q I V G D L S Y A W Q L I D S - F T    frog KIAA0196
557   L I N L K E D I E I H I Q M I T D F S Y A W H L L Q F D P T    fruit fly KIAA0196
537   T I N I K E E V L I T M Q I V G D L S Y A W Q I I D S - F T    zebrafish KIAA0196
475   V L S L S D S M I P E V Y S K M E S T Y L W P L I S Q - L I    C elegans KIAA0196
525   I V N I K E E V L V N L S V C A D M S Y A W E I V N N - Y V    amoeba KIAA0196

---------+------------------+------------------+-----------
                 570                580                590
           ---------+------------------+------------------+-----------
566   S I M Q E S I R V N P S M V T K L R A T F L K L A S A L D L    human KIAA0196
566   S I M Q E S I R V N P S M V T K L R A T F L K L A S A L D L    orangutan KIAA0196
566   S I M Q E S I R V N P S M V T K L R A T F L K L A S A L D L    mouse KIAA0196
309   S I M Q E S I R V N P S M V T K L R A T F L K L A S A L D L    rat KIAA0196
727   D I M Q E S I R V N P S M V T K L R A T F L K L A S A L D L    dog KIAA0196
504   S I M Q E S I R V S P S M V T K L R A T F L K L A S A L D L    fowl KIAA0196
566   A I M Q E S I R A N P S M V T K L R A T F L K L A S A L D L    frog KIAA0196
587   P P M Q E H I K R Q P Q A V I G I R A V F L K L A S T L E V    fruit fly KIAA0196
566   A I M Q E S I R A N P S M V T K L R A T L L K L A S A L D L    zebrafish KIAA0196
504   P R I Q Q N L V S - T S N T D V V R Q I F T K L S I S C Y M    C elegans KIAA0196
554   D Q M Q K G I K S D P K C V L K L R A T F L K L V S I L D L    amoeba KIAA0196

----------------+---               --------------------+--------
                 600                610                620
           ----------------+---               --------------------+--------
596   P L L R I N Q A N S P D L L S - - V S Q Y Y S G E L V S Y V    human KIAA0196
596   P L L R I N Q A N S P D L L S - - V S Q Y Y S G E L V S Y V    orangutan KIAA0196
596   P L L R I N Q A N S P D L L S - - V S Q Y Y S G E L V S Y V    mouse KIAA0196
339   P L L R I N Q A N S P D L L S - - V S Q Y Y S G E L V S Y V    rat KIAA0196
757   P L L R I N Q A N S P D L L S - - V S Q Y Y S G E L V S Y V    dog KIAA0196
534   P L L R I N Q A N S P D L L S - - V S Q Y Y S G E L V S Y V    fowl KIAA0196
596   P L L R I N Q A N S P D L L S - - V S Q Y Y S G E L V F Y V    frog KIAA0196
617   P L M R I N Q A R S E D L V S - - V S N Y Y S T E L A N F L    fruit fly KIAA0196
596   P L L R I N Q V N S P D L L S - - V S Q F Y S G E L V A Y V    zebrafish KIAA0196
533   L K L K L S N F S D K D H V A S R I A N T Y S Y A L E K N L    C elegans KIAA0196
584   P L V R I A Q C S S P D L I S - - V S E Y Y S G E L V G Y V    amoeba KIAA0196

------------+------------------+------------------+---------
                 630                640                650
              ------------+------------------+------------------+---------
624   R K V L Q I I P E S M F T S L L K I I K L Q T H D I I E V P    human KIAA0196
624   R K V L Q I I P E S M F T S L L K I I K L Q T H D I I E V P    orangutan KIAA0196
624   R K V L Q I I P E S M F T S L L K I I K L Q T H D I M E V P    mouse KIAA0196
367   R K V L Q I I P E S M F T S L L K I I K L Q T H D I I E V P    rat KIAA0196
785   R K V L Q I I P E S M F T S L L K I I K L Q T H D I I E V P    dog KIAA0196
562   R K V L Q I I P E S M F T S L L K I I K L Q T H D I I E V P    fowl KIAA0196
624   R K V L Q I I P E S M F T S L A K I I K L Q T H D I I E V P    frog KIAA0196
645   R R V L Q I V P E T M F S I L A K I I Y L L T N V I K E F P    fruit fly KIAA0196
624   R K V L Q I I P E S M F T S L A K I I K L Q I H D I M E V P    zebrafish KIAA0196
563   K T V L Q S V P Q H L F G I M Y N V I M P G L G K T F E P -    C elegans KIAA0196
612   R K V L E I V P K Q M F L I L K Q I I N M Q T N N I Q E M P    amoeba KIAA0196

------------+------------------+----------
                 660                670
              ------------+------------------+----------
654   T R L D K D K L R D Y A Q L G P R Y E V A - - - - - - - - -    human KIAA0196
654   T R L D K D K L R D Y A Q L G P R Y E V A - - - - - - - - -    orangutan KIAA0196
654   T R L D K D K L R D Y A Q L G P R Y E V A - - - - - - - - -    mouse KIAA0196
397   T R L D K D K L R D Y A Q L G P R Y E V A - - - - - - - - -    rat KIAA0196
815   T R L D K D K L R D Y A Q L G P R Y E V A C P F D F C L L I    dog KIAA0196
592   T R L D K D K L R D Y A Q L G P R Y E V A - - - - - - - - -    fowl KIAA0196
654   T R L D K D K L R D Y A Q L G A R Y E V A - - - - - - - - -    frog KIAA0196
```

Figure 16 (Continued)

```
675 T K V E K E R L K D Y A Q F E E R A K V A - - - - - - - - -  fruit fly KIAA0196
654 T R L D K D K L K D Y S Q L S A R Y E V A - - - - - - - - -  zebrafish KIAA0196
592 - Y I E K T E L R E L S E F V T N S R L V - - - - - - - - -  C elegans KIAA0196
642 T K V E K E R L R D F A Q L D Q R Y D L A - - - - - - - - -  amoeba KIAA0196
```

Figure 16 (Continued)

```
                                          ----------+---------------
                                                   680
                                          ----------+---------------
675  - - - - - - - - - - - - - - - - - - - K L T H A I S I F T E G I   human KIAA0196
675  - - - - - - - - - - - - - - - - - - - K L T H A I S I F T E G I   orangutan KIAA0196
675  - - - - - - - - - - - - - - - - - - - K L T H A I S I F T E G I   mouse KIAA0196
418  - - - - - - - - - - - - - - - - - - - K L T H A I S I F T E G I   rat KIAA0196
845  F N T Q P M T R H K S A L P A V A K L T H A I S I F T E G I       dog KIAA0196
613  - - - - - - - - - - - - - - - - - - - K L T H A I S I F T E G I   fowl KIAA0196
675  - - - - - - - - - - - - - - - - - - - K L T N A I S I F T E G I   frog KIAA0196
696  - - - - - - - - - - - - - - - - - - - Q L T N S I A V F T K G I   fruit fly KIAA0196
675  - - - - - - - - - - - - - - - - - - - K L T H A I S V F T E G I   zebrafish KIAA0196
612  - - - - - - - - - - - - - - - - - - - E T T S L I A N T S M G I   C elegans KIAA0196
663  - - - - - - - - - - - - - - - - - - - R A T H S V S V F T E G I   amoeba KIAA0196

----+--------------------+--------------------+---------------
            690                  700                  710
        ----+--------------------+--------------------+---------------
688  L M M K T T L V G I I K V D P K Q L L E D G I R K E L V K R   human KIAA0196
688  L M M K T T L V G I I K V D P K Q L L E D G I R K E L V K R   orangutan KIAA0196
688  L M M K T T L V G I I K V D P K Q L L E D G I R K E L V K R   mouse KIAA0196
431  L M M K T T L V G I I K V D P K Q L L E D G I R K E L V K R   rat KIAA0196
875  L M M K T T L V G I I K V D P K Q L L E D G I R K E L V K R   dog KIAA0196
626  L M M K T T L V G I I K V D P K Q L L E D G I R K E L V K R   fowl KIAA0196
688  L M M K T T L V G I I K V D P K Q L L E D G I R K E L V K R   frog KIAA0196
709  L M M K T T L V G V I E L D P K Q L L E D G I R K E L V N H   fruit fly KIAA0196
688  L M M K T T L V G I I Q V D P K Q L L E D G I R K E L V K R   zebrafish KIAA0196
625  S R M M L T R V G T I E I N P K E L L E E G M I R Q L Y K E   C elegans KIAA0196
676  L A M E T T L V G I I E V D P K Q L L E D G I R K E L V L Q   amoeba KIAA0196

----+--------------------    +------------                    ----
            720                          730
        ----+--------------------    +------------                    ----
718  V A F A L H R G L I F N - - P R A K P S - - - - - - - - E L   human KIAA0196
718  V A F A L H R G L I F N - - P R A K P S - - - - - - - - E L   orangutan KIAA0196
718  V A F A L H R G L I F N - - P R A K P S - - - - - - - - E L   mouse KIAA0196
461  V A F A L H R G L I F N - - P R A K P S - - - - - - - - E L   rat KIAA0196
905  V A F A L H R G L I F N - - P R A K P S - - - - - - - - E L   dog KIAA0196
656  V A L A L H R G L I F N - - P R A K P S - - - - - - - - E L   fowl KIAA0196
718  V A V A L H K G L I F N - - S R A K P S - - - - - - - - E L   frog KIAA0196
739  L A N A Y N L G L I F T P E K G K T P V Q - - - - - - - L L   fruit fly KIAA0196
718  V A Y A L H K G L I F N - - P K A K P S - - - - - - - - E L   zebrafish KIAA0196
655  I K K M I G T - - - - - - - T S A T S S - - - - - - - - - -   C elegans KIAA0196
706  I A L A M D K T L I F S G K P Y Q A P S N K Q Q Q Q E I E L   amoeba KIAA0196

----+--------------------+--------------------+---------------
            740                  750                  760
        ----+--------------------+--------------------+---------------
738  M P K L K E L G A T M D G F H R S F E Y I Q D Y V N I Y G L   human KIAA0196
738  M P K L K E L G A T M D G F H R S F E Y I Q D Y V S I Y G L   orangutan KIAA0196
738  M P K L K E L G A T M D G F H R S F E Y I Q D Y V S I Y G L   mouse KIAA0196
481  M P K L K E L G A T M D G F H R S F E Y I Q D Y V N I Y G L   rat KIAA0196
925  M P K L K E L G A T M D G F H R S F E Y I Q D Y V N I Y G L   dog KIAA0196
676  M P K L K E M A A T M D G F H R S F E Y I Q D Y V N I Y G L   fowl KIAA0196
738  L P K L K D M A A T M D G F H R S F E Y I Q D Y V S I Y G L   frog KIAA0196
762  Q Q K L Q A L A K T I E G Y R R S F E Y I E D Y L R V Q G L   fruit fly KIAA0196
738  M P K L K E M A A T M D G F Y R S F E Y I Q D Y V S I Y G L   zebrafish KIAA0196
668  I E N L L K M C D N I E T M R C S F L Y L C D Y M N L D G E   C elegans KIAA0196
736  L Q R L K E L S N I L D G F R R S F Q Y I Q D Y V N I Q G L   amoeba KIAA0196
```

Figure 16 (Continued)

```
              ----+------------------+-----------------+---------------
                  770                780               790
              ----+------------------+-----------------+---------------
       768    K I W Q E E V S R I I N Y N V E Q E C N N F L R T K I Q D W    human KIAA0196
       768    K I W Q E E V S R I I N Y N V E Q E C N N F L R T K I Q D W    orangutan KIAA0196
       768    K I W Q E E V S R I I N Y N V E Q E C N N F L R T K I Q D W    mouse KIAA0196
       511    K I W Q E E V S R I I N Y N V E Q E C N N F L R T K I Q D W    rat KIAA0196
       955    K I W Q E E V S R I I N Y N V E Q E C N N F L R T K I Q D W    dog KIAA0196
       706    K I W Q E E V S R I I N Y N V E Q E C N N F L R T K I Q D W    fowl KIAA0196
       768    K I W Q E E V S R I V N Y N V E Q E C N N F L R T K I Q D W    frog KIAA0196
       792    R I L L E E S Q R I I N Y N V E K E C N A F L R N K V Q E F    fruit fly KIAA0196
       768    K I W Q E E V S R I I N Y N V E Q E C N S F L R T K I Q D W    zebrafish KIAA0196
       698    H V W S - - - - - - - - - - - V A M D D F F S - R I S E E    C elegans KIAA0196
       766    K I W Q E E F S R I V N F Y V E Q E C N S F L K K K V Y D W    amoeba KIAA0196

----+------------------+-----------------       ----------+------
                  800                810                                820
              ----+------------------+-----------------       ----------+------
       798    Q S M Y Q S T H I P I P K F T P - - - - V D E S V T F I G    human KIAA0196
       798    Q S M Y Q S T H I P I P K F T P - - - - V D E S V T F I G    orangutan KIAA0196
       798    Q S M Y Q S T H I P I P K F A P - - - - V D E S I T F I G    mouse KIAA0196
       541    Q S I Y Q S T H I P I P K F A P - - - - V D E S I T F I G    rat KIAA0196
       985    Q S M Y Q S T H I P I P K F P P - - - - V D E S V T F I G    dog KIAA0196
       736    Q S I Y Q S T H I P I P K F T P - - - - V D E S V T F I G    fowl KIAA0196
       798    Q S M Y Q S T H I P I P K F P P - - - - V D E S M T F I G    frog KIAA0196
       822    Q S E H Q S Q I I P I P N F P P - - - L L G D P S N N F I G    fruit fly KIAA0196
       798    Q S V H Q S T H I P I P K Y P S - - - - V D E S A T F I G    zebrafish KIAA0196
       715    R A F A R S - - - - - S - - G - - - - - E L E K N Y I A    C elegans KIAA0196
       796    Q S Q Y Q S V A I P I P K F P S Q S D Q N S Q Q S V N M I G    amoeba KIAA0196

--------------+------------------+----------------+----
                            830                840              850
              --------------+------------------+----------------+----
       823    R L C R E I L R I T D P K M T C H I D Q L N T W Y D M K T -    human KIAA0196
       823    R L C R E I L R I T D P K M T C H I D Q L N T W Y D M K T -    orangutan KIAA0196
       823    R L C R E I L R I T D P K M T C Y I D Q L N T W Y D M K T -    mouse KIAA0196
       566    R L C R E I L R I T D P K V T C Y I D Q L N T W Y D M K T -    rat KIAA0196
      1010    R L C R E I L R I T D P K M T C H I D Q L N T W Y D M K T -    dog KIAA0196
       761    R L C R E I L R I T D P K I T C Y I D Q M N T W Y D V K T -    fowl KIAA0196
       823    R L C R E I L R I T D P K V T C Y I D Q M N T W Y D M K T -    frog KIAA0196
       849    R L A H E I L R C T D P K Q T I F L D L K S T W Y E K K A P    fruit fly KIAA0196
       823    R L C R E I L R I T D P K V T C Y I D Q L N T W Y D L R T -    zebrafish KIAA0196
       731    E L F - - - I K I T N P K A S R F S E S S L S W K D V K M -    C elegans KIAA0196
       826    R L A R E L L N Q T N C K T T L Y L N Q I G - W F D P S S -    amoeba KIAA0196

--------------     ----+------------------+----------------+--
                                     860                870              880
              --------------     ----+------------------+----------------+--
       852    H Q E V T S - S R L F S E I Q T T L G T F G L N G L D R L L    human KIAA0196
       852    H Q E V T S - S R L F S E I Q T T L G T F G L N G L D R L L    orangutan KIAA0196
       852    H Q E V T S - S R L F S E I Q T T L G T F G L N G L D R L L    mouse KIAA0196
       595    R Q E V T S - S R L F S E I Q T T L G T F G L N G L D R L L    rat KIAA0196
      1039    H Q E V T S - S R L F S E I Q T T L G T F G L N G L D R L L    dog KIAA0196
       790    H Q E V T S - S R L F S E I Q D T L G T F G L N G L D R L L    fowl KIAA0196
       852    H Q E V T N - N H L F S E I N D S L G T F G L N G L D R L L    frog KIAA0196
       879    H Q E V L A G S G F F E I L R E A L A P A G M V G L E R L Y    fruit fly KIAA0196
       852    H Q E V T N - N R L F S E I Q D T L G T F G L N G L D R L L    zebrafish KIAA0196
       757    S K T V L S - F D V F D R I E K I V P F H I L T S I E T H I    C elegans KIAA0196
       854    G K E L V G - I N T W S I L H Q S V G I F G L T G L D K L F    amoeba KIAA0196
```

Figure 16 (Continued)

```
                ------------------+-------------------+-------------------+-
                                 890                 900                 910
                ------------------+-------------------+-------------------+-
 881   C F M I V K E L Q N F L S M F Q K I I L R D R T V Q D T L K    human KIAA0196
 881   C F M I V K E L Q N F L S M F Q K I I L R D R T V Q D T L K    orangutan KIAA0196
 881   C F M I V K E L Q N F L S M F Q K I I L K E R T V Q E T L K    mouse KIAA0196
 624   C F M I V K E L Q N F L S M F Q K I I L R E R T V Q E T L K    rat KIAA0196
1068   C F M I V K E L Q N F L S M F Q K I I L R D R T V Q D T L K    dog KIAA0196
 819   C F M I V K E L Q N F L S M F Q K N V L R D R T V Q D T L K    fowl KIAA0196
 881   C F M I V K E L Q N F I R L Y Q R L I L R D K S G Q E T L R    frog KIAA0196
 909   A H M L A D E L K R N L E R L Q R N L T S D R M W V D T L A    fruit fly KIAA0196
 881   C F M I V K E L Q N F L T V L Q K S I L K D K A V V D V F K    zebrafish KIAA0196
 786   T V E L E K M L I E Y I S - - - - - - - - N A R K I G V S F    C elegans KIAA0196
 883   S F M M V K D L Q V F V S - - Q T R S L V E K S L K G F L N    amoeba KIAA0196

---------------      ----+-------------------+-------------------
                                         920                 930
                 ---------------      ----+-------------------+-------------------
 911   T L M N A V S - - - - P L K S I V A N S N K I Y F S A I A K    human KIAA0196
 911   T L M N A V S - - - - P L K S I V A N S N K I Y F S A I A K    orangutan KIAA0196
 911   M L M S A V N - - - - P L K S I V A N S S K V Y L S A I T K    mouse KIAA0196
 654   T L M N A V S - - - - P L R S I V A N S N K V Y L A A I T K    rat KIAA0196
1098   T L M N A V S - - - - P L K S I V A N S N K I Y F S A I A K    dog KIAA0196
 849   A L M N A V S - - - - P L K G I I A N S N K V Y S A A I A K    fowl KIAA0196
 911   A L Q K V V T - - - - P V K G I V A N S A K I Y S A A I A K    frog KIAA0196
 939   A L T R E L E A R D F P T P E V S K Q P L K Y Y Q A Y T Q R    fruit fly KIAA0196
 911   A L L T A V N - - - - P V K G I V A N A S K V Y T N A A A K    zebrafish KIAA0196
 808   N L Q N S V T - - - - H E S A F Q F F T G P N Y E R L V K S    C elegans KIAA0196
 911   E F E D Y L R - - - - P T T N I P - D T M I R Y Q Q A L D K    amoeba KIAA0196

------+-------------------+-------------------+---------------
                     940                 950                 960
                ------+-------------------+-------------------+---------------
 937   T Q K I W T A Y L E A I M K V G Q M Q I L R Q Q I A N E L N    human KIAA0196
 937   T Q K I W T A Y L E A I M K V G Q M Q I L R Q Q I A N E L N    orangutan KIAA0196
 937   T Q K I W S A Y L E A I M K V G Q M Q I L R Q Q I A N E L N    mouse KIAA0196
 680   T Q K I W S T Y L E A I M K V G Q M Q I L R R Q I A N E L N    rat KIAA0196
1124   T Q K I W T A Y L E A I M K V G Q M Q I L R Q Q I A N E L N    dog KIAA0196
 875   T Q K I W T A Y L D S I M K V G Q M Q I L R Q Q I T N E L N    fowl KIAA0196
 937   T Q K I W P A Y L D A I M K V G Q M Q V L R Q Q I A N E L N    frog KIAA0196
 969   W L K V W P T L L D W V L C I G Q K Q L L R R E I A G E L S    fruit fly KIAA0196
 937   T Q K I W S P Y L E S I M K V G Q M Q I L R Q Q I A N E L N    zebrafish KIAA0196
 834   I Q P Q S A A L A A I L A Q I G Q Y L I I L R T I C N A K Q    C elegans KIAA0196
 936   T K L L Y P I F I D V L T K I G Q I Q L I R R Q I S N Q L N    amoeba KIAA0196

------+-------------------+-------------------+---------------
                     970                 980                 990
                ------+-------------------+-------------------+---------------
 967   Y S C R F D S K H L A A A L E N L N K A L L A D I E A H Y Q    human KIAA0196
 967   Y S C R F D S K H L A A A L E N L N K A L L A D I E A H Y Q    orangutan KIAA0196
 967   S S C R F D S R H L A A A L D N L N K A L L A D I E A H Y R    mouse KIAA0196
 710   S S C R F D S R H L A A A L D N L N K A L L A D I E A H Y R    rat KIAA0196
1154   Y S C R F D S K H L A A A L E N L N K A L L A D I E A H Y Q    dog KIAA0196
 905   Y S C R F D S K H L A A A L E N L N K A I L A D I E A H Y Q    fowl KIAA0196
 967   Y S C K F D S K H L A G A L E N F N E A I L A D I Q A H Y Q    frog KIAA0196
 999   F S S K C D A K L L E N T A D T L N K A L L L E L S L S - -    fruit fly KIAA0196
 967   Y S C K F D S K H L A A A L D N L N K S L L S D I E A H Y Q    zebrafish KIAA0196
 864   L A N R H K E D S I Q R D L I E M S I S M A R D P T D L - -    C elegans KIAA0196
 966   F H C K I D S N M L F S S L D I M N K S L L N D I E S H F Q    amoeba KIAA0196
```

Figure 16 (Continued)

```
            --+--------------------+--------------------+------------
              1000                 1010                 1020
            --+--------------------+--------------------+------------
 997   D P - S L P Y P K E D N T L L Y E I T A Y L E A A G I H N P   human KIAA0196
 997   D P - S L P Y P K E D N T L L Y E I T A Y L E A A G I H N P   orangutan KIAA0196
 997   D P - S L P Y P K E D N T L L Y E I T A Y L E A A G I H N P   mouse KIAA0196
 740   D P - S L P Y P K E D N T L L Y E I T A Y L E A A G I H N P   rat KIAA0196
1184   D P - S L P Y P K E D N T L L Y E I T A Y L E A A G I H N P   dog KIAA0196
 935   N P - S L P Y P K E D N T L L Y E I T A Y L E A A G I H N P   fowl KIAA0196
 997   D P - S L P C P R E D N T L L Y E I T A Y L E A A G T H N P   frog KIAA0196
1027   K D - - L - C D E K G V V M L T E L Q E T L L Y T G N F E P   fruit fly KIAA0196
 997   D P - S L P Y P K E D N T L L Y E I T A Y L E A A G I H N P   zebrafish KIAA0196
 892   - - - - - - - P T E M G T I L K L M M Q Y S L Y D P E R M I   C elegans KIAA0196
 996   R P D S N P Y P S D D N T L L F D L A Q Y L D T A G I N D P   amoeba KIAA0196

----                ----+--------------------+---------------
                               1030                 1040
                           ----+--------------------+---------------
1026   L N - - - - - - - - K I Y I T T K R L P Y F P I V N F L F L   human KIAA0196
1026   L N - - - - - - - - K I Y I T T K R L P Y F P I V N F L F L   orangutan KIAA0196
1026   L N - - - - - - - - K I Y I T T K R L P Y F P I V N F L F L   mouse KIAA0196
 769   L N - - - - - - - - K I Y I T T K R L P Y F P I V N F L F L   rat KIAA0196
1213   L N K V S V Q I M E Q I Y I T T K R L P Y F P V V N F L F L   dog KIAA0196
 964   L N - - - - - - - - K I Y I T T K R L P Y F P I V N F L F L   fowl KIAA0196
1026   L N - - - - - - - - K I Y I T T K Q L S F F P I V N F L F L   frog KIAA0196
1054   L E - - - - - - - - Q V F L I T K N T H N M A L F M F L F T   fruit fly KIAA0196
1026   L N - - - - - - - - K I Y I T T K R L P Y F P I V N F L F L   zebrafish KIAA0196
 915   F R - - - - - - - - - - - L K D E P S P L F I I A L V Q C L   C elegans KIAA0196
1026   F T - - - - - - - - K I Y I T T S P L E Q F P C L L F L F V   amoeba KIAA0196

----+--------------------+-  -------------------+------------
           1050                 1060                 1070
       ----+--------------------+-  -------------------+------------
1048   I A Q L P K L Q Y N K N L - G M V C R K P T D P V D W P P L   human KIAA0196
1048   I A Q L P K L Q Y N K N L - G M V C R K P T D P V D W P P L   orangutan KIAA0196
1048   I A Q L P K L Q Y N K N L - G M V C R K P A D P V D W P P L   mouse KIAA0196
 791   I A Q L P K L Q Y N K N L - G M V C R K P A D P V D W P P L   rat KIAA0196
1243   I A Q L P K L Q Y N K N L - G M V C R K P A D P V D W P P L   dog KIAA0196
 986   I S Q F P K L Q Y S K N L - G V V C K R P A D Q I D W L P L   fowl KIAA0196
1048   V A Q L P K L Q Y N K N L - G M T C R K P A D P V D W P V P L   frog KIAA0196
1076   I A H L G R M Q H S T I T D C L L P K S A K D N I D N V P F   fruit fly KIAA0196
1048   I A Q L P K L Q Y N K S Q - G M A C R K P A D A L D W A P L   zebrafish KIAA0196
 934   L P K I G D P Y F V C P K - - - - - - - Q - - - - - - - L   C elegans KIAA0196
1048   L S Q V S K F Q F N S K L N V M S S K K Q K N S Y D W T P F   amoeba KIAA0196

------+--------------------+--------------------+------------
             1080                 1090                 1100
       ------+--------------------+--------------------+------------
1077   V L G L L T L L K Q F H S R Y T E Q F L A L I G Q F I C S T   human KIAA0196
1077   V L G L L T L L K Q F H S R Y T E Q F L A L I G Q F I C S T   orangutan KIAA0196
1077   V L G L L T L L K Q F H S R Y T E Q F L A L I G Q F I R S T   mouse KIAA0196
 820   V L G L L T L L K Q F H S R Y T E Q F L A L I G Q F I R S T   rat KIAA0196
1272   V L G L L T L L K Q F H S R Y T E Q F L A L I G Q F I R S T   dog KIAA0196
1015   V L G L L T L L K Q F H S R Y T E Q F L T L I G Q F I R S T   fowl KIAA0196
1077   V L G L L T L L K Q F H S R Y T E Q F L A L I G Q F I R S S   frog KIAA0196
1106   I V G L V T I L Q Q F H K N V K M L Y I S Y M S Q Y V V T V   fruit fly KIAA0196
1077   V L G L L T L L K Q F H S R Y T E Q F L A L I G Q F I R S I   zebrafish KIAA0196
 949   E V G I R F V L R Q - - S R L L P Y F L P I I R E Q L P Q S   C elegans KIAA0196
1078   I I G C I T I L Q Q F H S L H T Q K F L A F V G Q Y I K S H   amoeba KIAA0196
```

Figure 16 (Continued)

```
                  -----+-----              ---------------+-------------------+-
                     1110                              1120                 1130
                  -----+-----              ---------------+-------------------+-
1107   V E Q C T S - - - - - - Q K I P E T P A D V V G A L L F L E   human KIAA0196
1107   V E Q C T S - - - - - - Q K I P E I P A D V V G A L L F L E   orangutan KIAA0196
1107   M E Q C T S - - - - - - Q K M P E M P A D A V G A L L F L E   mouse KIAA0196
 850   M E Q C T S - - - - - - Q K M P E M P A D A V G A L L F L E   rat KIAA0196
1302   V E Q C T S - - - - - - Q K I P E M P A D V V G A L L F L E   dog KIAA0196
1045   M E Q C M S - - - - - - Q K I P E M P A D V V A A L M F L E   fowl KIAA0196
1107   L E Q S T S - - - - - - Q K I P E M P A D V V G A L M F L E   frog KIAA0196
1136   S E A Q L L - - - - - - - D K E T L G P E V V T A L H F L L   fruit fly KIAA0196
1107   M E Q C T S - - - - - - Q K I P D M P S D V V G A L M F L E   zebrafish KIAA0196
 977   S R P K K R - - - - - - - - - - V S - D V D R F L R H L I     C elegans KIAA0196
1108   I N I A L A N P K E N N K D D A D Y P E D V I G L L R F L E   amoeba KIAA0196

---------------+-------------------+-
                          1140                 1150
              ---------------+-------------------+-
1131   D Y V R Y T K L P R R V A E A H V P N F - - - - - - - - - -   human KIAA0196
1131   D Y A R Y T K L P R R V A E A H V P N F - - - - - - - - - -   orangutan KIAA0196
1131   D Y V R Y T K L P R R V A E A H V P N F - - - - - - - - - -   mouse KIAA0196
 874   D Y V R Y T K L P R R V A E A H V P N F - - - - - - - - - -   rat KIAA0196
1326   D Y V R C G G G E R C I A A P A A P L L S S A R K S D P G V   dog KIAA0196
1069   D Y I R Y T K L P R K G D S S S V T L V P Y T V S V C E L L   fowl KIAA0196
1131   D Y V H F A K L P R R V V E A H V P N F - - - - - - - - - -   frog KIAA0196
1159   A F I R I A R L P L G V L E Q R I P N I I L S - - - - - - -   fruit fly KIAA0196
1131   D Y V R Y T K L P R K V A E A H V P S F - - - - - - - - - -   zebrafish KIAA0196
 995   S N L                                                         C elegans KIAA0196
1138   D F C K Y S H T S R K I V E G Y V P P Y - - - - - - - - - -   amoeba KIAA0196

---------------------
                    ---------------------
1151   - - - - - - - - - I F D E F R T V L                           human KIAA0196
1151   - - - - - - - - - I F D E F R T V L                           orangutan KIAA0196
1151   - - - - - - - - - I F D E F R T V L                           mouse KIAA0196
 894   - - - - - - - - - I F D E F R T V L                           rat KIAA0196
1356   R N S R N T G Q Q F M E W P T H L C I Q P L P V T R L A P K   dog KIAA0196
1099   G A G - - T G T R W D G A L G C L G T K K T N I P F P L P H   fowl KIAA0196
1151   - - - - - - - - - I F D E F R T I Q                           frog KIAA0196
1182   - - - - - - - - - E Y E Y L S T L L K                         fruit fly KIAA0196
1151   - - - - - - - - - I F D E F R T V L                           zebrafish KIAA0196
 997                                                                 C elegans KIAA0196
1158   - - - - - - - - - I F D Y Y N N                               amoeba KIAA0196

1159                                                                 human KIAA0196
1159                                                                 orangutan KIAA0196
1159                                                                 mouse KIAA0196
 902                                                                 rat KIAA0196
1386   D I F I                                                       dog KIAA0196
1127   N Y L Q F L G Y H V A T E K A Q L S A Y S S P F N T N M G I   fowl KIAA0196
1159                                                                 frog KIAA0196
1191                                                                 fruit fly KIAA0196
1159                                                                 zebrafish KIAA0196
 997                                                                 C elegans KIAA0196
1164                                                                 amoeba KIAA0196
```

Figure 16 (Continued)

SEQUENCE LISTING

<160> NUMBER OF SEQ ID NOS: 119

<210> SEQ ID NO 1
<211> LENGTH: 13
<212> TYPE: DNA
<213> ORGANISM: Homo sapiens

<400> SEQUENCE: 1
ctgaagtttt tgc                                                      13

<210> SEQ ID NO 2
<211> LENGTH: 13
<212> TYPE: DNA
<213> ORGANISM: Homo sapiens

<400> SEQUENCE: 2
ctgaaggttt tgc                                                      13

<210> SEQ ID NO 3
<211> LENGTH: 13
<212> TYPE: DNA
<213> ORGANISM: Homo sapiens

<400> SEQUENCE: 3
agagttcgta tcc                                                      13

<210> SEQ ID NO 4
<211> LENGTH: 13
<212> TYPE: DNA
<213> ORGANISM: Homo sapiens

<400> SEQUENCE: 4
agagttggta tcc                                                      13

<210> SEQ ID NO 5
<211> LENGTH: 13
<212> TYPE: DNA
<213> ORGANISM: Homo sapiens

<400> SEQUENCE: 5
ctagaagacc ttc                                                      13

<210> SEQ ID NO 6
<211> LENGTH: 13
<212> TYPE: DNA
<213> ORGANISM: Homo sapiens

<400> SEQUENCE: 6
ctagaaaacc ttc                                                      13

```
<210> SEQ ID NO 7
<211> LENGTH: 25
<212> TYPE: PRT
<213> ORGANISM: Homo sapiens

<400> SEQUENCE: 7

Val Ser Gln Tyr Tyr Ser Gly Glu Leu Val Ser Tyr Val Arg Lys Val
1               5                   10                  15

Leu Gln Ile Ile Pro Glu Ser Met Phe
            20                  25

<210> SEQ ID NO 8
<211> LENGTH: 25
<212> TYPE: PRT
<213> ORGANISM: Pan troglodytes

<400> SEQUENCE: 8

Val Ser Gln Tyr Tyr Ser Gly Glu Leu Val Ser Tyr Val Arg Lys Val
1               5                   10                  15

Leu Gln Ile Ile Pro Glu Ser Met Phe
            20                  25

<210> SEQ ID NO 9
<211> LENGTH: 25
<212> TYPE: PRT
<213> ORGANISM: Rattus norvegicus

<400> SEQUENCE: 9

Val Ser Gln Tyr Tyr Ser Gly Glu Leu Val Ser Tyr Val Arg Lys Val
1               5                   10                  15

Leu Gln Ile Ile Pro Glu Ser Met Phe
            20                  25

<210> SEQ ID NO 10
<211> LENGTH: 25
<212> TYPE: PRT
<213> ORGANISM: Mus musculus

<400> SEQUENCE: 10

Val Ser Gln Tyr Tyr Ser Gly Glu Leu Val Ser Tyr Val Arg Lys Val
1               5                   10                  15

Leu Gln Ile Ile Pro Glu Ser Met Phe
            20                  25

<210> SEQ ID NO 11
<211> LENGTH: 25
<212> TYPE: PRT
<213> ORGANISM: Canis familiaris

<400> SEQUENCE: 11

Val Ser Gln Tyr Tyr Ser Gly Glu Leu Val Ser Tyr Val Arg Lys Val
1               5                   10                  15

Leu Gln Ile Ile Pro Glu Ser Met Phe
            20                  25

<210> SEQ ID NO 12
<211> LENGTH: 25
<212> TYPE: PRT
<213> ORGANISM: Gallus gallus

<400> SEQUENCE: 12

Val Ser Gln Tyr Tyr Ser Gly Glu Leu Val Ser Tyr Val Arg Lys Val
1               5                   10                  15
```

Leu Gln Ile Ile Pro Glu Ser Met Phe
            20                  25

<210> SEQ ID NO 13
<211> LENGTH: 25
<212> TYPE: PRT
<213> ORGANISM: Danio rerio

<400> SEQUENCE: 13

Val Ser Gln Phe Tyr Ser Gly Glu Leu Val Ala Tyr Val Arg Lys Val
1               5                   10                  15

Leu Gln Ile Ile Pro Glu Ser Met Phe
            20                  25

<210> SEQ ID NO 14
<211> LENGTH: 25
<212> TYPE: PRT
<213> ORGANISM: Drosophila melanogaster

<400> SEQUENCE: 14

Val Ser Asn Tyr Tyr Ser Thr Glu Leu Ala Asn Phe Leu Arg Arg Val
1               5                   10                  15

Leu Gln Ile Val Pro Glu Thr Met Phe
            20                  25

<210> SEQ ID NO 15
<211> LENGTH: 25
<212> TYPE: PRT
<213> ORGANISM: Caenorhabditis elegans

<400> SEQUENCE: 15

Ile Ala Asn Thr Tyr Ser Tyr Ala Leu Glu Lys Asn Leu Lys Thr Val
1               5                   10                  15

Leu Gln Ser Val Pro Gln His Leu Phe
            20                  25

<210> SEQ ID NO 16
<211> LENGTH: 25
<212> TYPE: PRT
<213> ORGANISM: Xenopus tropicalis

<400> SEQUENCE: 16

Val Ser Gln Tyr Tyr Ser Gly Glu Leu Val Phe Tyr Val Arg Lys Val
1               5                   10                  15

Leu Gln Ile Ile Pro Glu Ser Met Phe
            20                  25

<210> SEQ ID NO 17
<211> LENGTH: 25
<212> TYPE: PRT
<213> ORGANISM: Dictyostelium discoideum

<400> SEQUENCE: 17

Val Ser Glu Tyr Tyr Ser Gly Glu Leu Val Gly Tyr Val Arg Lys Val
1               5                   10                  15

Leu Glu Ile Val Pro Lys Gln Met Phe
            20                  25

<210> SEQ ID NO 18
<211> LENGTH: 4173
<212> TYPE: DNA
<213> ORGANISM: Homo sapiens

<400> SEQUENCE: 18

```
acatgatgcc cctccctgct cccagccgct tcggtcatgt gaccgcctgg ggagtcaggg      60
gcggaagtcg gggtctgacc cgctccaggt ccgggactgc ggatagaaga ggaccgccgc     120
cttgagggag gggtggaaac tgggtgccga ctccgcgcgc gacctccggc cctgcgcgtg     180
cgccgtggcg cggcccggct gacaggttct ttaatggagg agccaatctc tctgcacacc     240
tggtttcatc taataatata cagacaccag ctctgaggcc agttaatcat ccccagtgtc     300
caggcacaga gtagtcggtc cgcctcacaa tgttggactt tctagccgag aacaacctct     360
gtggccaagc aatcctaagg attgttcct gtggtaatgc catcattgct gaacttttga     420
gactctctga gtttattcct gctgtgttca ggttaaaaga cagagctgat caacagaaat     480
atggagatat catatttgat ttcagctatt ttaagggtcc agaattatgg gaaagcaaac     540
tggatgctaa gccagagcta caggatttag atgaagaatt tcgtgaaaac aacatagaaa     600
ttgtgaccag atttattta gcatttcaaa gtgtacataa atatattgta gacttaaaca     660
gatatctaga tgatctcaat gaaggggttt atattcagca aaccttagaa actgtgcttc     720
tcaatgaaga tggaaaacaa cttctatgtg aagcactgta cttatatgga gttatgctac     780
tggtcattga ccaaaagatt gaaggagaag tcagagagag gatgctggtt tcttactacc     840
gatacagtgc tgctcgatct tctgctgatt caaatatgga cgatatttgt aagctgcttc     900
gaagtacagg ttattctagc caaccaggtg ccaaaagacc atccaactat cccgagagct     960
atttccagag agtgcctatc aacgaatcct tcatcagtat ggtcattggt cgactgagat    1020
ctgatgatat ttacaaccag gtctcagcgt atcctttgcc ggagcatcgc agcacagccc    1080
tggcaaacca agctgccatg ctgtacgtga ttctctactt tgagccttcc atccttcaca    1140
cccatcaagc aaaaatgaga gagatagtgg ataaatactt tccagataat tgggtaatta    1200
gtatttacat ggggatcaca gttaatctag tagatgcttg ggaaccttac aaagctgcaa    1260
aaactgcttt aaataatacc ctggaccttt caaatgtcag agaacaggca agcagatatg    1320
ctactgtcag tgaaagagtg catgctcaag tgcagcaatt tctaaaagaa ggttatttaa    1380
gggaggagat ggttctggac aatatcccaa agcttctgaa ctgcctgaga gactgcaatg    1440
ttgccatccg atggctgatg cttcatacag cagactcagc ctgtgaccca acaacaaac    1500
gccttcgtca aatcaaggac cagattctaa cagactctcg gtacaatccc aggatcctct    1560
tccagctgct gttagatact gcacaatttg agtttatact caaagagatg ttcaagcaaa    1620
tgctttcaga aaagcaaacc aaatgggagc attacaagaa agagggttcg gagcggatga    1680
ctgagcttgc tgatgtcttt tcaggagtga accccctaac cagagtggag aaaaatgaaa    1740
accttcaagc ttggttcaga gagatctcaa aacaaatatt gtctttaaat tatgatgatt    1800
ctactgctgc gggcagaaaa actgtacaac tgatacaagc tttggaagag gttcaagaat    1860
tccaccagtt ggaatccaat ctgcaagtat gtcagtttct tgccgatact cgaaagtttc    1920
ttcatcaaat gatcagaacc attaacatta agaggaggt tctgatcaca atgcagatcg    1980
ttggggacct ttctttcgct tggcagttga ttgacagttt cacatccatc atgcaagaaa    2040
gcataagggt aaatccatcc atggttacta aactcagagc taccttccta aagcttgcct    2100
ctgccctcga tctgccccctt ttcgtatta atcaggcaaa tagccccgac tgctcagcg    2160
tgtcacagta ctattctgga gagttggtat cctatgtgag aaaagttttg cagatcatcc    2220
cagaaagcat gtttacatct cttctaaaga tcataaagct tcagacccac gacattattg    2280
```

| | |
|---|---|
| aagtgcctac ccgcctggac aaagacaagc tgagggacta tgctcagcta ggcccacgat | 2340 |
| acgaggttgc caagcttact catgctattt ccattttttac tgaaggcatc ttaatgatga | 2400 |
| aaacgacttt ggttggcatc atcaaggtgg atccaaagca gttgctggaa gatggaataa | 2460 |
| ggaaagagct tgtgaagcgc gttgcctttg ccctgcatag gggactgata ttcaaccctc | 2520 |
| gagccaagcc aagtgaattg atgcccaagc tgaaagagtt gggagcgacc atggatggat | 2580 |
| tccatcgttc ttttgaatac ataccaggact atgtcaacat ttatggtctg aagatttggc | 2640 |
| aggaagaagt atctcgtatc ataaattaca acgtggagca agagtgtaat aactttctaa | 2700 |
| gaacgaagat tcaagattgg caaagcatgt accagtccac tcatattcca atacccaagt | 2760 |
| ttaccccctgt ggatgagtct gtaacgttta ttggtcgact ctgcagagaa atcctgcgga | 2820 |
| tcacagaccc aaaaatgaca tgtcacatag accagctgaa cacttggtat gatatgaaaa | 2880 |
| ctcatcagga agtgaccagc agccgcctct tctcagaaat ccagaccacc ttgggaacct | 2940 |
| ttggtctaaa tggcttagac aggcttctgt gctttatgat tgtaaaagag ttacagaatt | 3000 |
| tcctcagtat gtttcagaaa attatcctga gagacagaac tgttcaggac actttaaaaa | 3060 |
| ccctcatgaa tgctgtcagt cccctaaaaa gtattgtcgc aaattcaaat aaaatttatt | 3120 |
| tttccgccat tgccaaaaca cagaagattt ggactgcgta tctcgaggct ataatgaagg | 3180 |
| ttgggcagat gcagattctg agacaacaga ttgccaatga attaaattat tcttgtcggt | 3240 |
| ttgattctaa acatctggca gctgctctgg agaatctcaa taaggctctc ctagcagaca | 3300 |
| ttgaagccca ctatcaggac ccttcacttc cttaccccaa agaagataac acactttttat | 3360 |
| atgaaatcac agcctatctg gaggcagctg gcattcacaa cccactgaat aagatataca | 3420 |
| taacaacaaa gcgcttaccc tattttccaa ttgtaaactt tctattttg atcgctcagt | 3480 |
| tgccaaaact tcaatacaac aaaaatctgg gaatggtctg ccgaaaaccg accgacccgg | 3540 |
| ttgattggcc accacttgtc ctgggactgc tcactctgct gaagcagttc cattcccggt | 3600 |
| acaccgagca gttcctggcg ctgattggcc agtttatctg ctccacggtg gagcagtgta | 3660 |
| caagccagaa gatacctgaa ttcctgcag atgttgtggg tgcccttctg ttcctggagg | 3720 |
| attatgttcg gtacacaaag ctacccagga gggttgctga agcacatgtg cctaatttca | 3780 |
| tttttgatga gttcagaaca gtgctgtaac tgttttttcct acttcttcaa tggaaggatt | 3840 |
| gtccttagat cttcccacca tcacaaatga atttgaagat gaaaagaaac tcagttgctc | 3900 |
| atacaactgc atttttttctg tctattatgg gaaacatcag acgttctgag taagatatat | 3960 |
| ctcatggcat tagttaatat aactgatatt gtttaaatca tggtattaca tgcaatttat | 4020 |
| atcagataaa agcagaacac attttttgtac tgcctctctt aaatgctgaa tgtaactgtt | 4080 |
| atgtataaat ccatttagtt ttatgttcta aagaactatt tgtgcaactc cagattttca | 4140 |
| gtaaaatagt attactagta cccaaaaaaa aaa | 4173 |

<210> SEQ ID NO 19
<211> LENGTH: 1159
<212> TYPE: PRT
<213> ORGANISM: Homo sapiens

<400> SEQUENCE: 19

Met Leu Asp Phe Leu Ala Glu Asn Asn Leu Cys Gly Gln Ala Ile Leu
 1               5                  10                  15

Arg Ile Val Ser Cys Gly Asn Ala Ile Ile Ala Glu Leu Leu Arg Leu
            20                  25                  30

Ser Glu Phe Ile Pro Ala Val Phe Arg Leu Lys Asp Arg Ala Asp Gln

```
            35                  40                  45
Gln Lys Tyr Gly Asp Ile Ile Phe Asp Phe Ser Tyr Phe Lys Gly Pro
 50                  55                  60

Glu Leu Trp Glu Ser Lys Leu Asp Ala Lys Pro Glu Leu Gln Asp Leu
 65                  70                  75                  80

Asp Glu Glu Phe Arg Glu Asn Asn Ile Glu Ile Val Thr Arg Phe Tyr
                     85                  90                  95

Leu Ala Phe Gln Ser Val His Lys Tyr Ile Val Asp Leu Asn Arg Tyr
                    100                 105                 110

Leu Asp Asp Leu Asn Glu Gly Val Tyr Ile Gln Gln Thr Leu Glu Thr
                115                 120                 125

Val Leu Leu Asn Glu Asp Gly Lys Gln Leu Leu Cys Glu Ala Leu Tyr
            130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Arg Tyr Ser Ala Ala Arg
                    165                 170                 175

Ser Ser Ala Asp Ser Asn Met Asp Asp Ile Cys Lys Leu Leu Arg Ser
                180                 185                 190

Thr Gly Tyr Ser Ser Gln Pro Gly Ala Lys Arg Pro Ser Asn Tyr Pro
                195                 200                 205

Glu Ser Tyr Phe Gln Arg Val Pro Ile Asn Glu Ser Phe Ile Ser Met
            210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
                    245                 250                 255

Met Leu Tyr Val Ile Leu Tyr Phe Glu Pro Ser Ile Leu His Thr His
                260                 265                 270

Gln Ala Lys Met Arg Glu Ile Val Asp Lys Tyr Phe Pro Asp Asn Trp
                275                 280                 285

Val Ile Ser Ile Tyr Met Gly Ile Thr Val Asn Leu Val Asp Ala Trp
            290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                    325                 330                 335

Val His Ala Gln Val Gln Gln Phe Leu Lys Glu Gly Tyr Leu Arg Glu
                340                 345                 350

Glu Met Val Leu Asp Asn Ile Pro Lys Leu Leu Asn Cys Leu Arg Asp
                355                 360                 365

Cys Asn Val Ala Ile Arg Trp Leu Met Leu His Thr Ala Asp Ser Ala
            370                 375                 380

Cys Asp Pro Asn Asn Lys Arg Leu Arg Gln Ile Lys Asp Gln Ile Leu
385                 390                 395                 400

Thr Asp Ser Arg Tyr Asn Pro Arg Ile Leu Phe Gln Leu Leu Leu Asp
                    405                 410                 415

Thr Ala Gln Phe Glu Phe Ile Leu Lys Glu Met Phe Lys Gln Met Leu
                420                 425                 430

Ser Glu Lys Gln Thr Lys Trp Glu His Tyr Lys Lys Glu Gly Ser Glu
            435                 440                 445

Arg Met Thr Glu Leu Ala Asp Val Phe Ser Gly Val Lys Pro Leu Thr
450                 455                 460
```

```
Arg Val Glu Lys Asn Glu Asn Leu Gln Ala Trp Phe Arg Glu Ile Ser
465                 470                 475                 480

Lys Gln Ile Leu Ser Leu Asn Tyr Asp Asp Ser Thr Ala Ala Gly Arg
            485                 490                 495

Lys Thr Val Gln Leu Ile Gln Ala Leu Glu Glu Val Gln Glu Phe His
                500                 505                 510

Gln Leu Glu Ser Asn Leu Gln Val Cys Gln Phe Leu Ala Asp Thr Arg
            515                 520                 525

Lys Phe Leu His Gln Met Ile Arg Thr Ile Asn Ile Lys Glu Glu Val
        530                 535                 540

Leu Ile Thr Met Gln Ile Val Gly Asp Leu Ser Phe Ala Trp Gln Leu
545                 550                 555                 560

Ile Asp Ser Phe Thr Ser Ile Met Gln Glu Ser Ile Arg Val Asn Pro
                565                 570                 575

Ser Met Val Thr Lys Leu Arg Ala Thr Phe Leu Lys Leu Ala Ser Ala
            580                 585                 590

Leu Asp Leu Pro Leu Leu Arg Ile Asn Gln Ala Asn Ser Pro Asp Leu
            595                 600                 605

Leu Ser Val Ser Gln Tyr Tyr Ser Gly Glu Leu Val Ser Tyr Val Arg
        610                 615                 620

Lys Val Leu Gln Ile Ile Pro Glu Ser Met Phe Thr Ser Leu Leu Lys
625                 630                 635                 640

Ile Ile Lys Leu Gln Thr His Asp Ile Ile Glu Val Pro Thr Arg Leu
                645                 650                 655

Asp Lys Asp Lys Leu Arg Asp Tyr Ala Gln Leu Gly Pro Arg Tyr Glu
            660                 665                 670

Val Ala Lys Leu Thr His Ala Ile Ser Ile Phe Thr Glu Gly Ile Leu
        675                 680                 685

Met Met Lys Thr Thr Leu Val Gly Ile Ile Lys Val Asp Pro Lys Gln
        690                 695                 700

Leu Leu Glu Asp Gly Ile Arg Lys Glu Leu Val Lys Arg Val Ala Phe
705                 710                 715                 720

Ala Leu His Arg Gly Leu Ile Phe Asn Pro Arg Ala Lys Pro Ser Glu
                725                 730                 735

Leu Met Pro Lys Leu Lys Glu Leu Gly Ala Thr Met Asp Gly Phe His
            740                 745                 750

Arg Ser Phe Glu Tyr Ile Gln Asp Tyr Val Asn Ile Tyr Gly Leu Lys
        755                 760                 765

Ile Trp Gln Glu Glu Val Ser Arg Ile Ile Asn Tyr Asn Val Glu Gln
        770                 775                 780

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Thr Pro Val Asp Glu
                805                 810                 815

Ser Val Thr Phe Ile Gly Arg Leu Cys Arg Glu Ile Leu Arg Ile Thr
            820                 825                 830

Asp Pro Lys Met Thr Cys His Ile Asp Gln Leu Asn Thr Trp Tyr Asp
        835                 840                 845

Met Lys Thr His Gln Glu Val Thr Ser Ser Arg Leu Phe Ser Glu Ile
        850                 855                 860

Gln Thr Thr Leu Gly Thr Phe Gly Leu Asn Gly Leu Asp Arg Leu Leu
865                 870                 875                 880
```

```
Cys Phe Met Ile Val Lys Glu Leu Gln Asn Phe Leu Ser Met Phe Gln
                885                 890                 895

Lys Ile Ile Leu Arg Asp Arg Thr Val Gln Asp Thr Leu Lys Thr Leu
            900                 905                 910

Met Asn Ala Val Ser Pro Leu Lys Ser Ile Val Ala Asn Ser Asn Lys
        915                 920                 925

Ile Tyr Phe Ser Ala Ile Ala Lys Thr Gln Lys Ile Trp Thr Ala Tyr
    930                 935                 940

Leu Glu Ala Ile Met Lys Val Gly Gln Met Gln Ile Leu Arg Gln Gln
945                 950                 955                 960

Ile Ala Asn Glu Leu Asn Tyr Ser Cys Arg Phe Asp Ser Lys His Leu
                965                 970                 975

Ala Ala Ala Leu Glu Asn Leu Asn Lys Ala Leu Leu Ala Asp Ile Glu
            980                 985                 990

Ala His Tyr Gln Asp Pro Ser Leu Pro Tyr Pro Lys Glu Asp Asn Thr
        995                 1000                1005

Leu Leu Tyr Glu Ile Thr Ala Tyr Leu Glu Ala Gly Ile His Asn
    1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
                1045                1050                1055

Asn Lys Asn Leu Gly Met Val Cys Arg Lys Pro Thr Asp Pro Val Asp
            1060                1065                1070

Trp Pro Pro Leu Val Leu Gly Leu Leu Thr Leu Leu Lys Gln Phe His
        1075                1080                1085

Ser Arg Tyr Thr Glu Gln Phe Leu Ala Leu Ile Gly Gln Phe Ile Cys
    1090                1095                1100

Ser Thr Val Glu Gln Cys Thr Ser Gln Lys Ile Pro Glu Ile Pro Ala
1105                1110                1115                1120

Asp Val Val Gly Ala Leu Leu Phe Leu Glu Asp Tyr Val Arg Tyr Thr
                1125                1130                1135

Lys Leu Pro Arg Arg Val Ala Glu Ala His Val Pro Asn Phe Ile Phe
            1140                1145                1150

Asp Glu Phe Arg Thr Val Leu
    1155

<210> SEQ ID NO 20
<211> LENGTH: 4173
<212> TYPE: DNA
<213> ORGANISM: Homo sapiens

<400> SEQUENCE: 20
acatgatgcc cctccctgct cccagccgct tcggtcatgt gaccgcctgg ggagtcaggg    60
gcggaagtcg gggtctgacc cgctccaggt ccgggactgc ggatagaaga ggaccgccgc   120
cttgagggag gggtggaaac tgggtgccgg ctccgcgcgc gacctccggc cctgcgcgtg   180
cgccgtggcg cggcccggct gacaggttct ttaatggagg agccaatctc tctgcacacc   240
tggtttcatc taataatata cagacaccag ctctgaggcc agttaatcat ccccagtgtc   300
caggcacaga gtagtcggtc cgcctcacaa tgttggactt tctagccgag aacaacctct   360
gtggccaagc aatcctaagg attgtttcct gtggtaatgc catcattgct gaacttttga   420
gactctctga gttattcct gctgtgttca ggttaaaaga cagagctgat caacagaaat    480
atggagatat catatttgat ttcagctatt ttaagggtcc agaattatgg gaaagcaaac   540
```

```
tggatgctaa gccagagcta caggatttag atgaagaatt tcgtgaaaac aacatagaaa      600
ttgtgaccag attttattta gcatttcaaa gtgtacataa atatattgta gacttaaaca      660
gatatctaga tgatctcaat gaaggggttt atattcagca aaccttagaa actgtgcttc      720
tcaatgaaga tggaaaacaa cttctatgtg aagcactgta cttatatgga gttatgctac      780
tggtcattga ccaaaagatt gaaggagaag tcagagagag gatgctggtt tcttactacc      840
gatacagtgc tgctcgatct tctgctgatt caaatatgga cgatatttgt aagctgcttc      900
gaagtacagg ttattctagc caaccaggtg ccaaaagacc atccaactat cccgagagct      960
atttccagag agtgcctatc aacgaatcct tcatcagtat ggtcattggt cgactgagat     1020
ctgatgatat ttacaaccag gtctcagcgt atcctttgcc ggagcatcgc agcacagccc     1080
tggcaaacca agctgccatg ctgtacgtga ttctctactt tgagccttcc atccttcaca     1140
cccatcaagc aaaaatgaga gagatagtgg ataaatactt tccagataat tgggtaatta     1200
gtatttacat ggggatcaca gttaatctag tagatgcttg gaaccttac aaagctgcaa      1260 aaactgcttt aaataatacc ctggacctt caaatgtcag agaacaggca agcagatatg      1320
ctactgtcag tgaaagagtg catgctcaag tgcagcaatt tctaaaagaa ggttatttaa      1380
gggaggagat ggttctggac aatatcccaa agcttctgaa ctgcctgaga gactgcaatg     1440
ttgccatccg atggctgatg cttcatacag cagactcagc ctgtgaccca acaacaaac     1500 gccttcgtca aatcaaggac cagattctaa cagactctcg gtacaatccc aggatcctct     1560
tccagctgct gttagatact gcacaatttg agtttatact caaagagatg ttcaagcaaa     1620
tgctttcaga aaagcaaacc aaatgggagc attacaagaa agagggttcg gagcggatga     1680
ctgagcttgc tgatgtcttt tcaggagtga accccctaac cagagtggag aaaaatgaag     1740
accttcaagc ttggttcaga gagatctcaa aacaaatatt gtctttaaat tatgatgatt     1800
ctactgctgc gggcagaaaa actgtacaac tgatacaagc tttggaagag gttcaagaat     1860
tccaccagtt ggaatccaat ctgcaagtat gtcagtttct tgccgatact cgaaagtttc     1920
ttcatcaaat gatcagaacc attaacatta agaggaggt tctgatcaca atgcagatcg      1980
ttggggacct ttctttcgct tggcagttga ttgacagttt cacatccatc atgcaagaaa     2040
gcataagggt aaatccatcc atggttacta aactcagagc taccttccta aagcttgcct     2100
ctgccctcga tctgccccctt cttcgtatta tcaggcaaa tagcccccgac tgctcagcg     2160 tgtcacagta ctattctgga gagttggtat cctatgtgag aaaagttttg cagatcatcc     2220
cagaaagcat gtttacatct cttctaaaga tcataaagct tcagacccac gacattattg     2280
aagtgcctac ccgcctggac aaagacaagc tgagggacta tgctcagcta ggcccacgat     2340
acgaggttgc caagcttact catgctattt ccatttttac tgaaggcatc ttaatgatga     2400
aaacgacttt ggttggcatc atcaaggtgg atccaaagca gttgctggaa gatggaataa     2460
ggaaagagct tgtgaagcgc gttgcctttg ccctgcatag gggactgata ttcaaccctc     2520
gagccaagcc aagtgaattg atgcccaagc tgaaagagtt gggagcgacc atggatggat     2580
tccatcgttc ttttgaatac atacaggact atgtcaacat ttatggtctg aagatttggc     2640
aggaagaagt atctcgtatc ataaattaca acgtggagca agagtgtaat aactttctaa     2700
gaacgaagat tcaagattgg caaagcatgt accagtccac tcatattcca atacccaagt     2760
ttacccctgt ggatgagtct gtaacgttta ttggtcgact ctgcagagaa atcctgcgga     2820
tcacagaccc aaaaatgaca tgtcacatag accagctgaa cacttggtat gatatgaaaa     2880
```

```
ctcatcagga agtgaccagc agccgcctct tctcagaaat ccagaccacc ttgggaacct      2940
ttggtctaaa tggcttagac aggcttctgt gctttatgat tgtaaaagag ttacagaatt      3000
tcctcagtat gtttcagaaa attatcctga gagacagaac tgttcaggac actttaaaaa      3060
ccctcatgaa tgctgtcagt ccctaaaaa gtattgtcgc aaattcaaat aaaatttatt       3120
tttccgccat tgccaaaaca cagaagattt ggactgcgta tctcgaggct ataatgaagg      3180
ttgggcagat gcagattctg agacaacaga ttgccaatga attaaattat tcttgtcggt      3240
ttgattctaa acatctggca gctgctctgg agaatctcaa taaggctctc ctagcagaca      3300
ttgaagccca ctatcaggac ccttcacttc cttaccccaa agaagataac acactttat       3360 atgaaatcac agcctatctg gaggcagctg gcattcacaa cccactgaat aagatataca      3420
taacaacaaa gcgcttaccc tattttccaa ttgtaaactt tctattttg atcgctcagt       3480 tgccaaaact tcaatacaac aaaaatctgg gaatggtctg ccgaaaaccg accgacccgg      3540
ttgattggcc accacttgtc ctgggactgc tcactctgct gaagcagttc cattcccggt      3600
acaccgagca gttcctggcg ctgattggcc agtttatctg ctccacggtg gagcagtgta      3660
caagccagaa gatacctgaa attcctgcag atgttgtggg tgcccttctg ttcctggagg      3720
attatgttcg gtacacaaag ctacccagga gggttgctga agcacatgtg cctaatttca      3780
tttttgatga gttcagaaca gtgctgtaac tgttttcct acttcttcaa tggaaggatt      3840
gtccttagat cttcccacca tcacaaatga atttgaagat gaaagaaac tcagttgctc       3900 atacaactgc attttttctg tctattatgg gaaacatcag acgttctgag taagatatat      3960
ctcatggcat tagttaatat aactgatatt gtttaaatca tggtattaca tgcaatttat      4020
atcagataaa agcagaacac attttttgtac tgcctctctt aaatgctgaa tgtaactgtt       4080
atgtataaat ccatttagtt ttatgttcta aagaactatt tgtgcaactc cagattttca      4140
gtaaaatagt attactagta cccaaaaaaa aaa                                   4173

<210> SEQ ID NO 21
<211> LENGTH: 1159
<212> TYPE: PRT
<213> ORGANISM: Homo sapiens

<400> SEQUENCE: 21

Met Leu Asp Phe Leu Ala Glu Asn Asn Leu Cys Gly Gln Ala Ile Leu
1               5                   10                  15

Arg Ile Val Ser Cys Gly Asn Ala Ile Ile Ala Glu Leu Leu Arg Leu
            20                  25                  30

Ser Glu Phe Ile Pro Ala Val Phe Arg Leu Lys Asp Arg Ala Asp Gln
        35                  40                  45

Gln Lys Tyr Gly Asp Ile Ile Phe Asp Phe Ser Tyr Phe Lys Gly Pro
    50                  55                  60

Glu Leu Trp Glu Ser Lys Leu Asp Ala Lys Pro Glu Leu Gln Asp Leu
65                  70                  75                  80

Asp Glu Glu Phe Arg Glu Asn Asn Ile Glu Ile Val Thr Arg Phe Tyr
                85                  90                  95

Leu Ala Phe Gln Ser Val His Lys Tyr Ile Val Asp Leu Asn Arg Tyr
            100                 105                 110

Leu Asp Asp Leu Asn Glu Gly Val Tyr Ile Gln Gln Thr Leu Glu Thr
        115                 120                 125

Val Leu Leu Asn Glu Asp Gly Lys Gln Leu Leu Cys Glu Ala Leu Tyr
    130                 135                 140
```

```
Leu Tyr Gly Val Met Leu Val Ile Asp Gln Lys Ile Glu Gly Glu
145                 150                 155                 160

Val Arg Glu Arg Met Leu Val Ser Tyr Arg Tyr Ser Ala Ala Arg
            165                 170                 175

Ser Ser Ala Asp Ser Asn Met Asp Asp Ile Cys Lys Leu Leu Arg Ser
            180                 185                 190

Thr Gly Tyr Ser Ser Gln Pro Gly Ala Lys Arg Pro Ser Asn Tyr Pro
            195                 200                 205

Glu Ser Tyr Phe Gln Arg Val Pro Ile Asn Glu Ser Phe Ile Ser Met
    210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
            245                 250                 255

Met Leu Tyr Val Ile Leu Tyr Phe Glu Pro Ser Ile Leu His Thr His
            260                 265                 270

Gln Ala Lys Met Arg Glu Ile Val Asp Lys Tyr Phe Pro Asp Asn Trp
            275                 280                 285

Val Ile Ser Ile Tyr Met Gly Ile Thr Val Asn Leu Val Asp Ala Trp
            290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                325                 330                 335

Val His Ala Gln Val Gln Gln Phe Leu Lys Glu Gly Tyr Leu Arg Glu
            340                 345                 350

Glu Met Val Leu Asp Asn Ile Pro Lys Leu Leu Asn Cys Leu Arg Asp
            355                 360                 365

Cys Asn Val Ala Ile Arg Trp Leu Met Leu His Thr Ala Asp Ser Ala
370                 375                 380

Cys Asp Pro Asn Asn Lys Arg Leu Arg Gln Ile Lys Asp Gln Ile Leu
385                 390                 395                 400

Thr Asp Ser Arg Tyr Asn Pro Arg Ile Leu Phe Gln Leu Leu Leu Asp
            405                 410                 415

Thr Ala Gln Phe Glu Phe Ile Leu Lys Glu Met Phe Lys Gln Met Leu
            420                 425                 430

Ser Glu Lys Gln Thr Lys Trp Glu His Tyr Lys Lys Glu Gly Ser Glu
            435                 440                 445

Arg Met Thr Glu Leu Ala Asp Val Phe Ser Gly Val Lys Pro Leu Thr
450                 455                 460

Arg Val Glu Lys Asn Glu Asp Leu Gln Ala Trp Phe Arg Glu Ile Ser
465                 470                 475                 480

Lys Gln Ile Leu Ser Leu Asn Tyr Asp Asp Ser Thr Ala Ala Gly Arg
            485                 490                 495

Lys Thr Val Gln Leu Ile Gln Ala Leu Glu Glu Val Gln Glu Phe His
            500                 505                 510

Gln Leu Glu Ser Asn Leu Gln Val Cys Gln Phe Leu Ala Asp Thr Arg
            515                 520                 525

Lys Phe Leu His Gln Met Ile Arg Thr Ile Asn Ile Lys Glu Glu Val
            530                 535                 540

Leu Ile Thr Met Gln Ile Val Gly Asp Leu Ser Phe Ala Trp Gln Leu
545                 550                 555                 560

Ile Asp Ser Phe Thr Ser Ile Met Gln Glu Ser Ile Arg Val Asn Pro
```

```
            565                 570                 575
Ser Met Val Thr Lys Leu Arg Ala Thr Phe Leu Lys Leu Ala Ser Ala
                580                 585                 590
Leu Asp Leu Pro Leu Arg Ile Asn Gln Ala Asn Ser Pro Asp Leu
            595                 600                 605
Leu Ser Val Ser Gln Tyr Tyr Ser Gly Glu Leu Val Ser Tyr Val Arg
            610                 615                 620
Lys Val Leu Gln Ile Ile Pro Glu Ser Met Phe Thr Ser Leu Leu Lys
625                 630                 635                 640
Ile Ile Lys Leu Gln Thr His Asp Ile Ile Glu Val Pro Thr Arg Leu
                645                 650                 655
Asp Lys Asp Lys Leu Arg Asp Tyr Ala Gln Leu Gly Pro Arg Tyr Glu
                660                 665                 670
Val Ala Lys Leu Thr His Ala Ile Ser Ile Phe Thr Glu Gly Ile Leu
                675                 680                 685
Met Met Lys Thr Thr Leu Val Gly Ile Ile Lys Val Asp Pro Lys Gln
                690                 695                 700
Leu Leu Glu Asp Gly Ile Arg Lys Glu Leu Val Lys Arg Val Ala Phe
705                 710                 715                 720
Ala Leu His Arg Gly Leu Ile Phe Asn Pro Arg Ala Lys Pro Ser Glu
                725                 730                 735
Leu Met Pro Lys Leu Lys Glu Leu Gly Ala Thr Met Asp Gly Phe His
                740                 745                 750
Arg Ser Phe Glu Tyr Ile Gln Asp Tyr Val Asn Ile Tyr Gly Leu Lys
                755                 760                 765
Ile Trp Gln Glu Glu Val Ser Arg Ile Ile Asn Tyr Asn Val Glu Gln
                770                 775                 780
Glu Cys Asn Asn Phe Leu Arg Thr Lys Ile Gln Asp Trp Gln Ser Met
785                 790                 795                 800
Tyr Gln Ser Thr His Ile Pro Ile Pro Lys Phe Thr Pro Val Asp Glu
                805                 810                 815
Ser Val Thr Phe Ile Gly Arg Leu Cys Arg Glu Ile Leu Arg Ile Thr
                820                 825                 830
Asp Pro Lys Met Thr Cys His Ile Asp Gln Leu Asn Thr Trp Tyr Asp
                835                 840                 845
Met Lys Thr His Gln Glu Val Thr Ser Ser Arg Leu Phe Ser Glu Ile
                850                 855                 860
Gln Thr Thr Leu Gly Thr Phe Gly Leu Asn Gly Leu Asp Arg Leu Leu
865                 870                 875                 880
Cys Phe Met Ile Val Lys Glu Leu Gln Asn Phe Leu Ser Met Phe Gln
                885                 890                 895
Lys Ile Ile Leu Arg Asp Arg Thr Val Gln Asp Thr Leu Lys Thr Leu
                900                 905                 910
Met Asn Ala Val Ser Pro Leu Lys Ser Ile Val Ala Asn Ser Asn Lys
                915                 920                 925
Ile Tyr Phe Ser Ala Ile Ala Lys Thr Gln Lys Ile Trp Thr Ala Tyr
                930                 935                 940
Leu Glu Ala Ile Met Lys Val Gly Gln Met Gln Ile Leu Arg Gln Gln
945                 950                 955                 960
Ile Ala Asn Glu Leu Asn Tyr Ser Cys Arg Phe Asp Ser Lys His Leu
                965                 970                 975
Ala Ala Ala Leu Glu Asn Leu Asn Lys Ala Leu Leu Ala Asp Ile Glu
                980                 985                 990
```

```
Ala His Tyr Gln Asp Pro Ser Leu Pro Tyr Pro Lys Glu Asp Asn Thr
        995                1000                1005

Leu Leu Tyr Glu Ile Thr Ala Tyr Leu Glu Ala Ala Gly Ile His Asn
    1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
                1045                1050                1055

Asn Lys Asn Leu Gly Met Val Cys Arg Lys Pro Thr Asp Pro Val Asp
            1060                1065                1070

Trp Pro Pro Leu Val Leu Gly Leu Leu Thr Leu Leu Lys Gln Phe His
        1075                1080                1085

Ser Arg Tyr Thr Glu Gln Phe Leu Ala Leu Ile Gly Gln Phe Ile Cys
    1090                1095                1100

Ser Thr Val Glu Gln Cys Thr Ser Gln Lys Ile Pro Glu Ile Pro Ala
1105                1110                1115                1120

Asp Val Val Gly Ala Leu Leu Phe Leu Glu Asp Tyr Val Arg Tyr Thr
                1125                1130                1135

Lys Leu Pro Arg Arg Val Ala Glu Ala His Val Pro Asn Phe Ile Phe
            1140                1145                1150

Asp Glu Phe Arg Thr Val Leu
        1155
```

<210> SEQ ID NO 22
<211> LENGTH: 4173
<212> TYPE: DNA
<213> ORGANISM: Homo sapiens

<400> SEQUENCE: 22

```
acatgatgcc cctccctgct cccagccgct tcggtcatgt gaccgcctgg ggagtcaggg    60
gcggaagtcg gggtctgacc cgctccaggt ccgggactgc ggatagaaga ggaccgccgc   120
cttgagggag gggtggaaac tgggtgccgg ctccgcgcgc gacctccggc cctgcgcgtg   180
cgccgtggcg cggcccggct gacaggttct ttaatggagg agccaatctc tctgcacacc   240
tggtttcatc taataatata cagacaccag ctctgaggcc agttaatcat ccccagtgtc   300
caggcacaga gtagtcggtc cgcctcacaa tgttggactt tctagccgag aacaacctct   360
gtggccaagc aatcctaagg attgtttcct gtggtaatgc catcattgct gaacttttga   420
gactctctga gtttattcct gctgtgttca ggttaaaaga cagagctgat caacagaaat   480
atggagatat catatttgat ttcagctatt ttaagggtcc agaattatgg gaaagcaaac   540
tggatgctaa gccagagcta caggatttag atgaagaatt tcgtgaaaac aacatagaaa   600
ttgtgaccag attttattta gcatttcaaa gtgtacataa atatattgta gacttaaaca   660
gatatctaga tgatctcaat gaaggggttt atattcagca aaccttagaa actgtgcttc   720
tcaatgaaga tggaaaacaa cttctatgtg aagcactgta cttatatgga gttatgctac   780
tggtcattga ccaaaagatt gaaggagaag tcagagagag gatgctggtt tcttactacc   840
gatacagtgc tgctcgatct tctgctgatt caaatatgga cgatatttgt aagctgcttc   900
gaagtacagg ttattctagc caaccaggtg ccaaaagacc atccaactat cccgagagct   960
atttccagag agtgcctatc aacgaatcct tcatcagtat ggtcattggt cgactgagat  1020
ctgatgatat ttacaaccag gtctcagcgt atcctttgcc ggagcatcgc agcacagccc  1080
tggcaaacca agctgccatg ctgtacgtga ttctctactt tgagccttcc atccttcaca  1140
```

```
cccatcaagc aaaaatgaga gagatagtgg ataaatactt tccagataat tgggtaatta    1200
gtatttacat ggggatcaca gttaatctag tagatgcttg ggaaccttac aaagctgcaa    1260
aaactgcttt aaataatacc ctggaccttt caaatgtcag agaacaggca agcagatatg    1320
ctactgtcag tgaaagagtg catgctcaag tgcagcaatt tctaaaagaa ggttatttaa    1380
gggaggagat ggttctggac aatatcccaa agcttctgaa ctgcctgaga gactgcaatg    1440
ttgccatccg atggctgatg cttcatacag cagactcagc ctgtgaccca acaacaaac     1500 gccttcgtca aatcaaggac cagattctaa cagactctcg gtacaatccc aggatcctct    1560
tccagctgct gttagatact gcacaatttg agtttatact caaagagatg ttcaagcaaa    1620
tgctttcaga aaagcaaacc aaatgggagc attacaagaa agagggttcg gagcggatga    1680
ctgagcttgc tgatgtcttt tcaggagtga accccctaac cagagtggag aaaaatgaaa    1740
accttcaagc ttggttcaga gagatctcaa acaaatatt gtctttaaat tatgatgatt      1800
ctactgctgc gggcagaaaa actgtacaac tgatacaagc tttggaagag gttcaagaat    1860
tccaccagtt ggaatccaat ctgcaagtat gtcagtttct tgccgatact cgaaagtttc    1920
ttcatcaaat gatcagaacc attaacatta agaggaggt tctgatcaca atgcagatcg      1980
ttggggacct ttctttcgct tggcagttga ttgacagttt cacatccatc atgcaagaaa    2040
gcataagggt aaatccatcc atggttacta aactcagagc taccttccta aagcttgcct    2100
ctgccctcga tctgccccctt cttcgtatta atcaggcaaa tagccccgac ctgctcagcg    2160
tgtcacagta ctattctgga gagttcgtat cctatgtgag aaaagttttg cagatcatcc    2220
cagaaagcat gtttacatct cttctaaaga tcataaagct tcagacccac gacattattg    2280
aagtgcctac ccgcctggac aaagacaagc tgagggacta tgctcagcta ggcccacgat    2340
acgaggttgc caagcttact catgctattt ccatttttac tgaaggcatc ttaatgatga    2400
aaacgacttt ggttggcatc atcaaggtgg atccaaagca gttgctgaa gatggaataa      2460 ggaaagagct tgtgaagcgc gttgcctttg ccctgcatag gggactgata ttcaaccctc    2520
gagccaagcc aagtgaattg atgcccaagc tgaaagagtt gggagcgacc atggatggat    2580
tccatcgttc ttttgaatac atacaggact atgtcaacat ttatggtctg aagatttggc    2640
aggaagaagt atctcgtatc ataaattaca cgtggagca agagtgtaat aactttctaa      2700
gaacgaagat tcaagattgg caaagcatgt accagtccac tcatattcca atacccaagt    2760 ttaccctgt ggatgagtct gtaacgttta ttggtcgact ctgcagagaa atcctgcgga      2820
tcacagaccc aaaaatgaca tgtcacatag accagctgaa cacttggtat gatatgaaaa    2880
ctcatcagga agtgaccagc agccgcctct tctcagaaat ccagaccacc ttgggaacct    2940
ttggtctaaa tggcttagac aggcttctgt gctttatgat tgtaaaagag ttacagaatt    3000
tcctcagtat gtttcagaaa attatcctga gagacagaac tgttcaggac actttaaaaa    3060
ccctcatgaa tgctgtcagt cccctaaaaa gtattgtcgc aaattcaaat aaaatttatt    3120
tttccgccat tgccaaaaca cagaagattt ggactgcgta tctcgaggct ataatgaagg    3180
ttgggcagat gcagattctg agacaacaga ttgccaatga attaaattat tcttgtcggt    3240
ttgattctaa acatctggca gctgctctgg agaatctcaa taaggctctc ctagcagaca    3300
ttgaagccca ctatcaggac ccttcacttc cttaccccaa agaagataac acactttttat    3360 atgaaatcac agcctatctg gaggcagctg gcattcacaa cccactgaat aagatataca    3420
taacaacaaa gcgcttaccc tatttttccaa ttgtaaactt tctattttg atcgctcagt     3480
```

-continued

```
tgccaaaact tcaatacaac aaaaatctgg gaatggtctg ccgaaaaccg accgacccgg   3540
ttgattggcc accacttgtc ctgggactgc tcactctgct gaagcagttc cattcccggt   3600
acaccgagca gttcctggcg ctgattggcc agtttatctg ctccacggtg gagcagtgta   3660
caagccagaa gatacctgaa attcctgcag atgttgtggg tgcccttctg ttcctggagg   3720
attatgttcg gtacacaaag ctacccagga gggttgctga agcacatgtg cctaatttca   3780
tttttgatga gttcagaaca gtgctgtaac tgttttttcct acttcttcaa tggaaggatt   3840
gtccttagat cttcccacca tcacaaatga atttgaagat gaaagaaac tcagttgctc   3900 atacaactgc attttttctg tctattatgg gaaacatcag acgttctgag taagatatat   3960
ctcatggcat tagttaatat aactgatatt gtttaaatca tggtattaca tgcaatttat   4020
atcagataaa agcagaacac attttttgtac tgcctctctt aaatgctgaa tgtaactgtt   4080
atgtataaat ccatttagtt ttatgttcta aagaactatt tgtgcaactc cagattttca   4140
gtaaaatagt attactagta cccaaaaaaa aaa                                 4173
```

<210> SEQ ID NO 23
<211> LENGTH: 1159
<212> TYPE: PRT
<213> ORGANISM: Homo sapiens

<400> SEQUENCE: 23

```
Met Leu Asp Phe Leu Ala Glu Asn Asn Leu Cys Gly Gln Ala Ile Leu
 1               5                  10                  15

Arg Ile Val Ser Cys Gly Asn Ala Ile Ile Ala Glu Leu Leu Arg Leu
            20                  25                  30

Ser Glu Phe Ile Pro Ala Val Phe Arg Leu Lys Asp Arg Ala Asp Gln
        35                  40                  45

Gln Lys Tyr Gly Asp Ile Ile Phe Asp Phe Ser Tyr Phe Lys Gly Pro
    50                  55                  60

Glu Leu Trp Glu Ser Lys Leu Asp Ala Lys Pro Glu Leu Gln Asp Leu
65                  70                  75                  80

Asp Glu Glu Phe Arg Glu Asn Asn Ile Glu Ile Val Thr Arg Phe Tyr
                85                  90                  95

Leu Ala Phe Gln Ser Val His Lys Tyr Ile Val Asp Leu Asn Arg Tyr
            100                 105                 110

Leu Asp Asp Leu Asn Glu Gly Val Tyr Ile Gln Gln Thr Leu Glu Thr
        115                 120                 125

Val Leu Leu Asn Glu Asp Gly Lys Gln Leu Leu Cys Glu Ala Leu Tyr
    130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Tyr Arg Tyr Ser Ala Ala Arg
                165                 170                 175

Ser Ser Ala Asp Ser Asn Met Asp Asp Ile Cys Lys Leu Leu Arg Ser
            180                 185                 190

Thr Gly Tyr Ser Ser Gln Pro Gly Ala Lys Arg Pro Ser Asn Tyr Pro
        195                 200                 205

Glu Ser Tyr Phe Gln Arg Val Pro Ile Asn Glu Ser Phe Ile Ser Met
    210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
                245                 250                 255
```

```
Met Leu Tyr Val Ile Leu Tyr Phe Glu Pro Ser Ile Leu His Thr His
            260                 265                 270

Gln Ala Lys Met Arg Glu Ile Val Asp Lys Tyr Phe Pro Asp Asn Trp
        275                 280                 285

Val Ile Ser Ile Tyr Met Gly Ile Thr Val Asn Leu Val Asp Ala Trp
290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                325                 330                 335

Val His Ala Gln Val Gln Phe Leu Lys Glu Gly Tyr Leu Arg Glu
            340                 345                 350

Glu Met Val Leu Asp Asn Ile Pro Lys Leu Leu Asn Cys Leu Arg Asp
        355                 360                 365

Cys Asn Val Ala Ile Arg Trp Leu Met Leu His Thr Ala Asp Ser Ala
    370                 375                 380

Cys Asp Pro Asn Asn Lys Arg Leu Arg Gln Ile Lys Asp Gln Ile Leu
385                 390                 395                 400

Thr Asp Ser Arg Tyr Asn Pro Arg Ile Leu Phe Gln Leu Leu Leu Asp
                405                 410                 415

Thr Ala Gln Phe Glu Phe Ile Leu Lys Glu Met Phe Lys Gln Met Leu
            420                 425                 430

Ser Glu Lys Gln Thr Lys Trp Glu His Tyr Lys Lys Glu Gly Ser Glu
        435                 440                 445

Arg Met Thr Glu Leu Ala Asp Val Phe Ser Gly Val Lys Pro Leu Thr
    450                 455                 460

Arg Val Glu Lys Asn Glu Asn Leu Gln Ala Trp Phe Arg Glu Ile Ser
465                 470                 475                 480

Lys Gln Ile Leu Ser Leu Asn Tyr Asp Asp Ser Thr Ala Ala Gly Arg
                485                 490                 495

Lys Thr Val Gln Leu Ile Gln Ala Leu Glu Glu Val Gln Glu Phe His
            500                 505                 510

Gln Leu Glu Ser Asn Leu Gln Val Cys Gln Phe Leu Ala Asp Thr Arg
        515                 520                 525

Lys Phe Leu His Gln Met Ile Arg Thr Ile Asn Ile Lys Glu Glu Val
    530                 535                 540

Leu Ile Thr Met Gln Ile Val Gly Asp Leu Ser Phe Ala Trp Gln Leu
545                 550                 555                 560

Ile Asp Ser Phe Thr Ser Ile Met Gln Glu Ser Ile Arg Val Asn Pro
                565                 570                 575

Ser Met Val Thr Lys Leu Arg Ala Thr Phe Leu Lys Leu Ala Ser Ala
            580                 585                 590

Leu Asp Leu Pro Leu Leu Arg Ile Asn Gln Ala Asn Ser Pro Asp Leu
        595                 600                 605

Leu Ser Val Ser Gln Tyr Tyr Ser Gly Glu Phe Val Ser Tyr Val Arg
    610                 615                 620

Lys Val Leu Gln Ile Ile Pro Glu Ser Met Phe Thr Ser Leu Leu Lys
625                 630                 635                 640

Ile Ile Lys Leu Gln Thr His Asp Ile Ile Glu Val Pro Thr Arg Leu
                645                 650                 655

Asp Lys Asp Lys Leu Arg Asp Tyr Ala Gln Leu Gly Pro Arg Tyr Glu
            660                 665                 670
```

```
Val Ala Lys Leu Thr His Ala Ile Ser Ile Phe Thr Glu Gly Ile Leu
            675                 680                 685

Met Met Lys Thr Thr Leu Val Gly Ile Ile Lys Val Asp Pro Lys Gln
690                 695                 700

Leu Leu Glu Asp Gly Ile Arg Lys Glu Leu Val Lys Arg Val Ala Phe
705                 710                 715                 720

Ala Leu His Arg Gly Leu Ile Phe Asn Pro Arg Ala Lys Pro Ser Glu
            725                 730                 735

Leu Met Pro Lys Leu Lys Glu Leu Gly Ala Thr Met Asp Gly Phe His
            740                 745                 750

Arg Ser Phe Glu Tyr Ile Gln Asp Tyr Val Asn Ile Tyr Gly Leu Lys
            755                 760                 765

Ile Trp Gln Glu Glu Val Ser Arg Ile Ile Asn Tyr Asn Val Glu Gln
            770                 775                 780

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Thr Pro Val Asp Glu
            805                 810                 815

Ser Val Thr Phe Ile Gly Arg Leu Cys Arg Glu Ile Leu Arg Ile Thr
            820                 825                 830

Asp Pro Lys Met Thr Cys His Ile Asp Gln Leu Asn Thr Trp Tyr Asp
            835                 840                 845

Met Lys Thr His Gln Glu Val Thr Ser Ser Arg Leu Phe Ser Glu Ile
            850                 855                 860

Gln Thr Thr Leu Gly Thr Phe Gly Leu Asn Gly Leu Asp Arg Leu Leu
865                 870                 875                 880

Cys Phe Met Ile Val Lys Glu Leu Gln Asn Phe Leu Ser Met Phe Gln
            885                 890                 895

Lys Ile Ile Leu Arg Asp Arg Thr Val Gln Asp Thr Leu Lys Thr Leu
            900                 905                 910

Met Asn Ala Val Ser Pro Leu Lys Ser Ile Val Ala Asn Ser Asn Lys
            915                 920                 925

Ile Tyr Phe Ser Ala Ile Ala Lys Thr Gln Lys Ile Trp Thr Ala Tyr
            930                 935                 940

Leu Glu Ala Ile Met Lys Val Gly Gln Met Gln Ile Leu Arg Gln Gln
945                 950                 955                 960

Ile Ala Asn Glu Leu Asn Tyr Ser Cys Arg Phe Asp Ser Lys His Leu
            965                 970                 975

Ala Ala Ala Leu Glu Asn Leu Asn Lys Ala Leu Leu Ala Asp Ile Glu
            980                 985                 990

Ala His Tyr Gln Asp Pro Ser Leu Pro Tyr Pro Lys Glu Asp Asn Thr
            995                 1000                1005

Leu Leu Tyr Glu Ile Thr Ala Tyr Leu Glu Ala Ala Gly Ile His Asn
    1010                1015                1020

Pro Leu Asn Lys Ile Tyr Ile Thr Thr Lys Arg Leu Pro Tyr Phe Pro
1025                    1030                1035                1040

Ile Val Asn Phe Leu Phe Leu Ile Ala Gln Leu Pro Lys Leu Gln Tyr
            1045                1050                1055

Asn Lys Asn Leu Gly Met Val Cys Arg Lys Pro Thr Asp Pro Val Asp
            1060                1065                1070

Trp Pro Pro Leu Val Leu Gly Leu Leu Thr Leu Leu Lys Gln Phe His
    1075                1080                1085

Ser Arg Tyr Thr Glu Gln Phe Leu Ala Leu Ile Gly Gln Phe Ile Cys
```

```
                    1090              1095              1100
Ser Thr Val Glu Gln Cys Thr Ser Gln Lys Ile Pro Glu Ile Pro Ala
1105                1110              1115              1120

Asp Val Val Gly Ala Leu Leu Phe Leu Glu Asp Tyr Val Arg Tyr Thr
                    1125              1130              1135

Lys Leu Pro Arg Arg Val Ala Glu Ala His Val Pro Asn Phe Ile Phe
            1140              1145              1150

Asp Glu Phe Arg Thr Val Leu
        1155

<210> SEQ ID NO 24
<211> LENGTH: 4173
<212> TYPE: DNA
<213> ORGANISM: Homo sapiens

<400> SEQUENCE: 24
```

| | | | | | |
|---|---|---|---|---|---|
| acatgatgcc | cctccctgct | cccagccgct | tcggtcatgt | gaccgcctgg | ggagtcaggg | 60 |
| gcggaagtcg | gggtctgacc | cgctccaggt | ccgggactgc | ggatagaaga | ggaccgccgc | 120 |
| cttgagggag | gggtggaaac | tgggtgccgg | ctccgcgcgc | gacctccggc | cctgcgcgtg | 180 |
| cgccgtggcg | cggcccggct | gacaggttct | ttaatggagg | agccaatctc | tctgcacacc | 240 |
| tggtttcatc | taataatata | cagacaccag | ctctgaggcc | agttaatcat | ccccagtgtc | 300 |
| caggcacaga | gtagtcggtc | cgcctcacaa | tgttggactt | tctagccgag | aacaacctct | 360 |
| gtggccaagc | aatcctaagg | attgtttcct | gtggtaatgc | catcattgct | gaacttttga | 420 |
| gactctctga | gtttattcct | gctgtgttca | ggttaaaaga | cagagctgat | caacagaaat | 480 |
| atggagatat | catatttgat | ttcagctatt | ttaagggtcc | agaattatgg | gaaagcaaac | 540 |
| tggatgctaa | gccagagcta | caggatttag | atgaagaatt | tcgtgaaaac | aacatagaaa | 600 |
| ttgtgaccag | attttatta | gcatttcaaa | gtgtacataa | atatattgta | gacttaaaca | 660 |
| gatatctaga | tgatctcaat | gaaggggttt | atattcagca | aaccttagaa | actgtgcttc | 720 |
| tcaatgaaga | tggaaaacaa | cttctatgtg | aagcactgta | cttatatgga | gttatgctac | 780 |
| tggtcattga | ccaaaagatt | gaaggagaag | tcagagagag | gatgctggtt | tcttactacc | 840 |
| gatacagtgc | tgctcgatct | tctgctgatt | caaatatgga | cgatatttgt | aagctgcttc | 900 |
| gaagtacagg | ttattctagc | caaccaggtg | ccaaaagacc | atccaactat | cccgagagct | 960 |
| atttccagag | agtgcctatc | aacgaatcct | tcatcagtat | ggtcattggt | cgactgagat | 1020 |
| ctgatgatat | ttacaaccag | gtctcagcgt | atcctttgcc | ggagcatcgc | agcacagccc | 1080 |
| tggcaaaacca | agctgccatg | ctgtacgtga | ttctctactt | tgagccttcc | atccttcaca | 1140 |
| cccatcaagc | aaaaatgaga | gagatagtgg | ataaatactt | tccagataat | tgggtaatta | 1200 |
| gtatttacat | ggggatcaca | gttaatctag | tagatgcttg | gaaccttac | aaagctgcaa | 1260 |
| aaactgcttt | aaataatacc | ctggaccttt | caaatgtcag | agaacaggca | agcagatatg | 1320 |
| ctactgtcag | tgaaagagtg | catgctcaag | tgcagcaatt | tctaaaagaa | ggttatttaa | 1380 |
| gggaggagat | ggttctggac | aatatcccaa | agcttctgaa | ctgcctgaga | gactgcaatg | 1440 |
| ttgccatccg | atggctgatg | cttcatacag | cagactcagc | ctgtgaccca | aacaacaaac | 1500 |
| gccttcgtca | aatcaaggac | cagattctaa | cagactctcg | gtacaatccc | aggatcctct | 1560 |
| tccagctgct | gttagatact | gcacaatttg | agtttatact | caaagagatg | ttcaagcaaa | 1620 |
| tgctttcaga | aaagcaaacc | aaatgggagc | attacaagaa | agagggttcg | gagcggatga | 1680 |
| ctgagcttgc | tgatgtcttt | tcaggagtga | aaccctaac | cagagtggag | aaaaatgaaa | 1740 |

```
accttcaagc ttggttcaga gagatctcaa acaaatatt gtctttaaat tatgatgatt    1800
ctactgctgc gggcagaaaa actgtacaac tgatacaagc tttggaagag gttcaagaat    1860
tccaccagtt ggaatccaat ctgcaagtat gtcagtttct tgccgatact cgaaagtttc    1920
ttcatcaaat gatcagaacc attaacatta agaggaggt tctgatcaca atgcagatcg    1980
ttggggacct ttctttcgct tggcagttga ttgacagttt cacatccatc atgcaagaaa    2040
gcataagggt aaatccatcc atggttacta aactcagagc taccttccta aagcttgcct    2100
ctgccctcga tctgccccct cttcgtatta atcaggcaaa tagccccgac tgctcagcg    2160 tgtcacagta ctattctgga gagttggtat cctatgtgag aaaattttg cagatcatcc    2220 cagaaagcat gtttacatct cttctaaaga tcataaagct tcagacccac gacattattg    2280
aagtgcctac ccgcctggac aaagacaagc tgagggacta tgctcagcta ggcccacgat    2340
acgaggttgc caagcttact catgctattt ccattttac tgaaggcatc ttaatgatga    2400
aaacgacttt ggttggcatc atcaaggtgg atccaaagca gttgctgaa gatggaataa    2460 ggaaagagct tgtgaagcgc gttgcctttg ccctgcatag gggactgata ttcaaccctc    2520
gagccaagcc aagtgaattg atgcccaagc tgaaagagtt gggagcgacc atggatggat    2580
tccatcgttc ttttgaatac atacaggact atgtcaacat ttatggtctg aagatttggc    2640
aggaagaagt atctcgtatc ataaattaca acgtggagca agagtgtaat aactttctaa    2700
gaacgaagat tcaagattgg caaagcatgt accagtccac tcatattcca atacccaagt    2760 ttaccctgt ggatgagtct gtaacgttta ttggtcgact ctgcagagaa atcctgcgga    2820
tcacagaccc aaaaatgaca tgtcacatag accagctgaa cacttggtat gatatgaaaa    2880
ctcatcagga agtgaccagc agccgcctct tctcagaaat ccagaccacc ttgggaacct    2940
ttggtctaaa tggcttagac aggcttctgt gctttatgat tgtaaaagag ttacagaatt    3000
tcctcagtat gtttcagaaa attatcctga gagacagaac tgttcaggac actttaaaaa    3060
ccctcatgaa tgctgtcagt cccctaaaaa gtattgtcgc aaattcaaat aaaaatttatt    3120 tttccgccat tgccaaaaca cagaagattt ggactgcgta tctcgaggct ataatgaagg    3180
ttgggcagat gcagattctg agacaacaga ttgccaatga attaaattat tcttgtcggt    3240
ttgattctaa acatctggca gctgctctgg agaatctcaa taaggctctc ctagcagaca    3300
ttgaagccca ctatcaggac ccttcacttc cttaccccaa agaagataac acacttttat    3360
atgaaatcac agcctatctg gaggcagctg gcattcacaa cccactgaat aagatataca    3420
taacaacaaa gcgcttaccc tattttccaa ttgtaaactt tctattttg atcgctcagt    3480 tgccaaaact tcaatacaac aaaaatctgg gaatggtctg ccgaaaaccg accgacccgg    3540
ttgattggcc accacttgtc ctgggactgc tcactctgct gaagcagttc cattcccggt    3600
acaccgagca gttcctggcg ctgattggcc agtttatctg ctccacggtg gagcagtgta    3660
caagccagaa gatacctgaa attcctgcag atgttgtggg tgcccttctg ttcctggagg    3720
attatgttcg gtacacaaag ctacccagga gggttgctga agcacatgtg cctaatttca    3780
tttttgatga gttcagaaca gtgctgtaac tgttttttcct acttcttcaa tggaaggatt    3840
gtccttagat cttcccacca tcacaaatga atttgaagat gaaagaaac tcagttgctc    3900 atacaactgc attttttctg tctattatgg gaaacatcag acgttctgag taagatatat    3960
ctcatggcat tagttaatat aactgatatt gtttaaatca tggtattaca tgcaatttat    4020
atcagataaa agcagaacac atttttgtac tgcctctctt aaatgctgaa tgtaactgtt    4080
```

```
atgtataaat ccatttagtt ttatgttcta aagaactatt tgtgcaactc cagattttca    4140
gtaaaatagt attactagta cccaaaaaaa aaa                                 4173
```

<210> SEQ ID NO 25
<211> LENGTH: 1159
<212> TYPE: PRT
<213> ORGANISM: Homo sapiens

<400> SEQUENCE: 25

```
Met Leu Asp Phe Leu Ala Glu Asn Asn Leu Cys Gly Gln Ala Ile Leu
 1               5                  10                  15

Arg Ile Val Ser Cys Gly Asn Ala Ile Ile Ala Glu Leu Leu Arg Leu
            20                  25                  30

Ser Glu Phe Ile Pro Ala Val Phe Arg Leu Lys Asp Arg Ala Asp Gln
        35                  40                  45

Gln Lys Tyr Gly Asp Ile Ile Phe Asp Phe Ser Tyr Phe Lys Gly Pro
    50                  55                  60

Glu Leu Trp Glu Ser Lys Leu Asp Ala Lys Pro Glu Leu Gln Asp Leu
65                  70                  75                  80

Asp Glu Glu Phe Arg Glu Asn Asn Ile Glu Ile Val Thr Arg Phe Tyr
                85                  90                  95

Leu Ala Phe Gln Ser Val His Lys Tyr Ile Val Asp Leu Asn Arg Tyr
           100                 105                 110

Leu Asp Asp Leu Asn Glu Gly Val Tyr Ile Gln Gln Thr Leu Glu Thr
       115                 120                 125

Val Leu Leu Asn Glu Asp Gly Lys Gln Leu Leu Cys Glu Ala Leu Tyr
   130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Tyr Arg Tyr Ser Ala Ala Arg
                165                 170                 175

Ser Ser Ala Asp Ser Asn Met Asp Asp Ile Cys Lys Leu Leu Arg Ser
           180                 185                 190

Thr Gly Tyr Ser Ser Gln Pro Gly Ala Lys Arg Pro Ser Asn Tyr Pro
       195                 200                 205

Glu Ser Tyr Phe Gln Arg Val Pro Ile Asn Glu Ser Phe Ile Ser Met
   210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
                245                 250                 255

Met Leu Tyr Val Ile Leu Tyr Phe Glu Pro Ser Ile Leu His Thr His
           260                 265                 270

Gln Ala Lys Met Arg Glu Ile Val Asp Lys Tyr Phe Pro Asp Asn Trp
       275                 280                 285

Val Ile Ser Ile Tyr Met Gly Ile Thr Val Asn Leu Val Asp Ala Trp
   290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                325                 330                 335

Val His Ala Gln Val Gln Gln Phe Leu Lys Glu Gly Tyr Leu Arg Glu
           340                 345                 350

Glu Met Val Leu Asp Asn Ile Pro Lys Leu Leu Asn Cys Leu Arg Asp
```

-continued

```
                355                 360                 365
Cys Asn Val Ala Ile Arg Trp Leu Met Leu His Thr Ala Asp Ser Ala
370                 375                 380
Cys Asp Pro Asn Asn Lys Arg Leu Arg Gln Ile Lys Asp Gln Ile Leu
385                 390                 395                 400
Thr Asp Ser Arg Tyr Asn Pro Arg Ile Leu Phe Gln Leu Leu Leu Asp
                405                 410                 415
Thr Ala Gln Phe Glu Phe Ile Leu Lys Glu Met Phe Lys Gln Met Leu
                420                 425                 430
Ser Glu Lys Gln Thr Lys Trp Glu His Tyr Lys Lys Glu Gly Ser Glu
                435                 440                 445
Arg Met Thr Glu Leu Ala Asp Val Phe Ser Gly Val Lys Pro Leu Thr
                450                 455                 460
Arg Val Glu Lys Asn Glu Asn Leu Gln Ala Trp Phe Arg Glu Ile Ser
465                 470                 475                 480
Lys Gln Ile Leu Ser Leu Asn Tyr Asp Asp Ser Thr Ala Ala Gly Arg
                485                 490                 495
Lys Thr Val Gln Leu Ile Gln Ala Leu Glu Glu Val Gln Glu Phe His
                500                 505                 510
Gln Leu Glu Ser Asn Leu Gln Val Cys Gln Phe Leu Ala Asp Thr Arg
                515                 520                 525
Lys Phe Leu His Gln Met Ile Arg Thr Ile Asn Ile Lys Glu Glu Val
                530                 535                 540
Leu Ile Thr Met Gln Ile Val Gly Asp Leu Ser Phe Ala Trp Gln Leu
545                 550                 555                 560
Ile Asp Ser Phe Thr Ser Ile Met Gln Glu Ser Ile Arg Val Asn Pro
                565                 570                 575
Ser Met Val Thr Lys Leu Arg Ala Thr Phe Leu Lys Leu Ala Ser Ala
                580                 585                 590
Leu Asp Leu Pro Leu Leu Arg Ile Asn Gln Ala Asn Ser Pro Asp Leu
                595                 600                 605
Leu Ser Val Ser Gln Tyr Tyr Ser Gly Glu Leu Val Ser Tyr Val Arg
                610                 615                 620
Lys Phe Leu Gln Ile Ile Pro Glu Ser Met Phe Thr Ser Leu Leu Lys
625                 630                 635                 640
Ile Ile Lys Leu Gln Thr His Asp Ile Ile Glu Val Pro Thr Arg Leu
                645                 650                 655
Asp Lys Asp Lys Leu Arg Asp Tyr Ala Gln Leu Gly Pro Arg Tyr Glu
                660                 665                 670
Val Ala Lys Leu Thr His Ala Ile Ser Ile Phe Thr Glu Gly Ile Leu
                675                 680                 685
Met Met Lys Thr Thr Leu Val Gly Ile Ile Lys Val Asp Pro Lys Gln
                690                 695                 700
Leu Leu Glu Asp Gly Ile Arg Lys Glu Leu Val Lys Arg Val Ala Phe
705                 710                 715                 720
Ala Leu His Arg Gly Leu Ile Phe Asn Pro Arg Ala Lys Pro Ser Glu
                725                 730                 735
Leu Met Pro Lys Leu Lys Glu Leu Gly Ala Thr Met Asp Gly Phe His
                740                 745                 750
Arg Ser Phe Glu Tyr Ile Gln Asp Tyr Val Asn Ile Tyr Gly Leu Lys
                755                 760                 765
Ile Trp Gln Glu Glu Val Ser Arg Ile Ile Asn Tyr Asn Val Glu Gln
770                 775                 780
```

-continued

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Thr Pro Val Asp Glu
            805                 810                 815

Ser Val Thr Phe Ile Gly Arg Leu Cys Arg Glu Ile Leu Arg Ile Thr
        820                 825                 830

Asp Pro Lys Met Thr Cys His Ile Asp Gln Leu Asn Thr Trp Tyr Asp
            835                 840                 845

Met Lys Thr His Gln Glu Val Thr Ser Ser Arg Leu Phe Ser Glu Ile
850                 855                 860

Gln Thr Thr Leu Gly Thr Phe Gly Leu Asn Gly Leu Asp Arg Leu Leu
865                 870                 875                 880

Cys Phe Met Ile Val Lys Glu Leu Gln Asn Phe Leu Ser Met Phe Gln
            885                 890                 895

Lys Ile Ile Leu Arg Asp Arg Thr Val Gln Asp Thr Leu Lys Thr Leu
            900                 905                 910

Met Asn Ala Val Ser Pro Leu Lys Ser Ile Val Ala Asn Ser Asn Lys
            915                 920                 925

Ile Tyr Phe Ser Ala Ile Ala Lys Thr Gln Lys Ile Trp Thr Ala Tyr
930                 935                 940

Leu Glu Ala Ile Met Lys Val Gly Gln Met Gln Ile Leu Arg Gln Gln
945                 950                 955                 960

Ile Ala Asn Glu Leu Asn Tyr Ser Cys Arg Phe Asp Ser Lys His Leu
            965                 970                 975

Ala Ala Ala Leu Glu Asn Leu Asn Lys Ala Leu Leu Ala Asp Ile Glu
            980                 985                 990

Ala His Tyr Gln Asp Pro Ser Leu Pro Tyr Pro Lys Glu Asp Asn Thr
            995                 1000                1005

Leu Leu Tyr Glu Ile Thr Ala Tyr Leu Glu Ala Ala Gly Ile His Asn
    1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
            1045                1050                1055

Asn Lys Asn Leu Gly Met Val Cys Arg Lys Pro Thr Asp Pro Val Asp
            1060                1065                1070

Trp Pro Pro Leu Val Leu Gly Leu Leu Thr Leu Leu Lys Gln Phe His
            1075                1080                1085

Ser Arg Tyr Thr Glu Gln Phe Leu Ala Leu Ile Gly Gln Phe Ile Cys
            1090                1095                1100

Ser Thr Val Glu Gln Cys Thr Ser Gln Lys Ile Pro Glu Ile Pro Ala
1105                1110                1115                1120

Asp Val Val Gly Ala Leu Leu Phe Leu Glu Asp Tyr Val Arg Tyr Thr
            1125                1130                1135

Lys Leu Pro Arg Arg Val Ala Glu Ala His Val Pro Asn Phe Ile Phe
            1140                1145                1150

Asp Glu Phe Arg Thr Val Leu
        1155

<210> SEQ ID NO 26
<211> LENGTH: 1159
<212> TYPE: PRT
<213> ORGANISM: Homo sapiens

```
<400> SEQUENCE: 26

Met Leu Asp Phe Leu Ala Glu Asn Asn Leu Cys Gly Gln Ala Ile Leu
 1               5                  10                  15

Arg Ile Val Ser Cys Gly Asn Ala Ile Ile Ala Glu Leu Leu Arg Leu
             20                  25                  30

Ser Glu Phe Ile Pro Ala Val Phe Arg Leu Lys Asp Arg Ala Asp Gln
         35                  40                  45

Gln Lys Tyr Gly Asp Ile Ile Phe Asp Phe Ser Tyr Phe Lys Gly Pro
     50                  55                  60

Glu Leu Trp Glu Ser Lys Leu Asp Ala Lys Pro Glu Leu Gln Asp Leu
 65                  70                  75                  80

Asp Glu Glu Phe Arg Glu Asn Asn Ile Glu Ile Val Thr Arg Phe Tyr
                 85                  90                  95

Leu Ala Phe Gln Ser Val His Lys Tyr Ile Val Asp Leu Asn Arg Tyr
            100                 105                 110

Leu Asp Asp Leu Asn Glu Gly Val Tyr Ile Gln Gln Thr Leu Glu Thr
        115                 120                 125

Val Leu Leu Asn Glu Asp Gly Lys Gln Leu Leu Cys Glu Ala Leu Tyr
130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Arg Tyr Ser Ala Ala Arg
                165                 170                 175

Ser Ser Ala Asp Ser Asn Met Asp Asp Ile Cys Lys Leu Leu Arg Ser
            180                 185                 190

Thr Gly Tyr Ser Ser Gln Pro Gly Ala Lys Arg Pro Ser Asn Tyr Pro
        195                 200                 205

Glu Ser Tyr Phe Gln Arg Val Pro Ile Asn Glu Ser Phe Ile Ser Met
    210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
                245                 250                 255

Met Leu Tyr Val Ile Leu Tyr Phe Glu Pro Ser Ile Leu His Thr His
            260                 265                 270

Gln Ala Lys Met Arg Glu Ile Val Asp Lys Tyr Phe Pro Asp Asn Trp
        275                 280                 285

Val Ile Ser Ile Tyr Met Gly Ile Thr Val Asn Leu Val Asp Ala Trp
    290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                325                 330                 335

Val His Ala Gln Val Gln Gln Phe Leu Lys Glu Gly Tyr Leu Arg Glu
            340                 345                 350

Glu Met Val Leu Asp Asn Ile Pro Lys Leu Leu Asn Cys Leu Arg Asp
        355                 360                 365

Cys Asn Val Ala Ile Arg Trp Leu Met Leu His Thr Ala Asp Ser Ala
    370                 375                 380

Cys Asp Pro Asn Asn Lys Arg Leu Arg Gln Ile Lys Asp Gln Ile Leu
385                 390                 395                 400

Thr Asp Ser Arg Tyr Asn Pro Arg Ile Leu Phe Gln Leu Leu Leu Asp
                405                 410                 415
```

```
Thr Ala Gln Phe Glu Phe Ile Leu Lys Glu Met Phe Lys Gln Met Leu
                420                 425                 430

Ser Glu Lys Gln Thr Lys Trp Glu His Tyr Lys Lys Glu Gly Ser Glu
            435                 440                 445

Arg Met Thr Glu Leu Ala Asp Val Phe Ser Gly Val Lys Pro Leu Thr
        450                 455                 460

Arg Val Glu Lys Asn Glu Asn Leu Gln Ala Trp Phe Arg Glu Ile Ser
465                 470                 475                 480

Lys Gln Ile Leu Ser Leu Asn Tyr Asp Asp Ser Thr Ala Ala Gly Arg
                485                 490                 495

Lys Thr Val Gln Leu Ile Gln Ala Leu Glu Glu Val Gln Glu Phe His
            500                 505                 510

Gln Leu Glu Ser Asn Leu Gln Val Cys Gln Phe Leu Ala Asp Thr Arg
        515                 520                 525

Lys Phe Leu His Gln Met Ile Arg Thr Ile Asn Ile Lys Glu Glu Val
530                 535                 540

Leu Ile Thr Met Gln Ile Val Gly Asp Leu Ser Phe Ala Trp Gln Leu
545                 550                 555                 560

Ile Asp Ser Phe Thr Ser Ile Met Gln Glu Ser Ile Arg Val Asn Pro
                565                 570                 575

Ser Met Val Thr Lys Leu Arg Ala Thr Phe Leu Lys Leu Ala Ser Ala
            580                 585                 590

Leu Asp Leu Pro Leu Leu Arg Ile Asn Gln Ala Asn Ser Pro Asp Leu
        595                 600                 605

Leu Ser Val Ser Gln Tyr Tyr Ser Gly Glu Leu Val Ser Tyr Val Arg
            610                 615                 620

Lys Val Leu Gln Ile Ile Pro Glu Ser Met Phe Thr Ser Leu Leu Lys
625                 630                 635                 640

Ile Ile Lys Leu Gln Thr His Asp Ile Ile Glu Val Pro Thr Arg Leu
                645                 650                 655

Asp Lys Asp Lys Leu Arg Asp Tyr Ala Gln Leu Gly Pro Arg Tyr Glu
            660                 665                 670

Val Ala Lys Leu Thr His Ala Ile Ser Ile Phe Thr Glu Gly Ile Leu
        675                 680                 685

Met Met Lys Thr Thr Leu Val Gly Ile Ile Lys Val Asp Pro Lys Gln
        690                 695                 700

Leu Leu Glu Asp Gly Ile Arg Lys Glu Leu Val Lys Arg Val Ala Phe
705                 710                 715                 720

Ala Leu His Arg Gly Leu Ile Phe Asn Pro Arg Ala Lys Pro Ser Glu
                725                 730                 735

Leu Met Pro Lys Leu Lys Glu Leu Gly Ala Thr Met Asp Gly Phe His
            740                 745                 750

Arg Ser Phe Glu Tyr Ile Gln Asp Tyr Val Asn Ile Tyr Gly Leu Lys
        755                 760                 765

Ile Trp Gln Glu Glu Val Ser Arg Ile Ile Asn Tyr Asn Val Glu Gln
        770                 775                 780

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Thr Pro Val Asp Glu
                805                 810                 815

Ser Val Thr Phe Ile Gly Arg Leu Cys Arg Glu Ile Leu Arg Ile Thr
            820                 825                 830
```

```
Asp Pro Lys Met Thr Cys His Ile Asp Gln Leu Asn Thr Trp Tyr Asp
            835                 840                 845

Met Lys Thr His Gln Glu Val Thr Ser Ser Arg Leu Phe Ser Glu Ile
850                 855                 860

Gln Thr Thr Leu Gly Thr Phe Gly Leu Asn Gly Leu Asp Arg Leu Leu
865                 870                 875                 880

Cys Phe Met Ile Val Lys Glu Leu Gln Asn Phe Leu Ser Met Phe Gln
                885                 890                 895

Lys Ile Ile Leu Arg Asp Arg Thr Val Gln Asp Thr Leu Lys Thr Leu
            900                 905                 910

Met Asn Ala Val Ser Pro Leu Lys Ser Ile Val Ala Asn Ser Asn Lys
            915                 920                 925

Ile Tyr Phe Ser Ala Ile Ala Lys Thr Gln Lys Ile Trp Thr Ala Tyr
            930                 935                 940

Leu Glu Ala Ile Met Lys Val Gly Gln Met Gln Ile Leu Arg Gln Gln
945                 950                 955                 960

Ile Ala Asn Glu Leu Asn Tyr Ser Cys Arg Phe Asp Ser Lys His Leu
                965                 970                 975

Ala Ala Ala Leu Glu Asn Leu Asn Lys Ala Leu Leu Ala Asp Ile Glu
            980                 985                 990

Ala His Tyr Gln Asp Pro Ser Leu Pro Tyr Pro Lys Glu Asp Asn Thr
            995                1000                1005

Leu Leu Tyr Glu Ile Thr Ala Tyr Leu Glu Ala Ala Gly Ile His Asn
           1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
                1045                1050                1055

Asn Lys Asn Leu Gly Met Val Cys Arg Lys Pro Thr Asp Pro Val Asp
           1060                1065                1070

Trp Pro Pro Leu Val Leu Gly Leu Leu Thr Leu Leu Lys Gln Phe His
           1075                1080                1085

Ser Arg Tyr Thr Glu Gln Phe Leu Ala Leu Ile Gly Gln Phe Ile Cys
           1090                1095                1100

Ser Thr Val Glu Gln Cys Thr Ser Gln Lys Ile Pro Glu Ile Pro Ala
1105                1110                1115                1120

Asp Val Val Gly Ala Leu Leu Phe Leu Glu Asp Tyr Val Arg Tyr Thr
                1125                1130                1135

Lys Leu Pro Arg Arg Val Ala Glu Ala His Val Pro Asn Phe Ile Phe
           1140                1145                1150

Asp Glu Phe Arg Thr Val Leu
           1155

<210> SEQ ID NO 27
<211> LENGTH: 1159
<212> TYPE: PRT
<213> ORGANISM: Pan troglodytes

<400> SEQUENCE: 27

Met Leu Asp Phe Leu Ala Glu Asn Asn Leu Cys Gly Gln Ala Ile Leu
 1               5                  10                  15

Arg Ile Val Ser Cys Gly Asn Ala Ile Ile Ala Glu Leu Leu Arg Leu
            20                  25                  30

Ser Glu Phe Ile Pro Ala Val Phe Arg Leu Lys Asp Arg Ala Asp Gln
            35                  40                  45
```

```
Gln Lys Tyr Gly Asp Ile Ile Phe Asp Phe Ser Tyr Phe Lys Gly Pro
    50                  55                  60

Glu Leu Trp Glu Ser Lys Leu Asp Ala Lys Pro Glu Leu Gln Asp Leu
65                  70                  75                  80

Asp Glu Glu Phe Arg Glu Asn Asn Ile Glu Ile Val Thr Arg Phe Tyr
                85                  90                  95

Leu Ala Phe Gln Ser Val His Lys Tyr Ile Val Asp Leu Asn Arg Tyr
                100                 105                 110

Leu Asp Asp Leu Asn Glu Gly Val Tyr Ile Gln Gln Thr Leu Glu Thr
                115                 120                 125

Val Leu Leu Asn Glu Asp Gly Lys Gln Leu Leu Cys Glu Ala Leu Tyr
                130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Arg Tyr Ser Ala Ala Arg
                165                 170                 175

Ser Ser Ala Asp Ser Asn Met Asp Asp Ile Cys Lys Leu Leu Arg Ser
                180                 185                 190

Thr Gly Tyr Ser Ser Gln Pro Gly Ala Lys Arg Pro Ser Asn Tyr Pro
                195                 200                 205

Glu Ser Tyr Phe Gln Arg Val Pro Ile Asn Glu Ser Phe Ile Ser Met
    210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
                245                 250                 255

Met Leu Tyr Val Ile Leu Tyr Phe Glu Pro Ser Ile Leu His Thr His
                260                 265                 270

Gln Ala Lys Met Arg Glu Ile Val Asp Lys Tyr Phe Pro Asp Asn Trp
                275                 280                 285

Val Ile Ser Ile Tyr Met Gly Ile Thr Val Asn Leu Val Asp Ala Trp
                290                 295                 300

Glu Pro Tyr Lys Ala Ala Lys Thr Ala Leu Asn Asn Thr Leu Asp Leu
305                 310                 315                 320

Ser Asn Val Arg Glu Gln Ala Ser Arg Tyr Ala Thr Val Ser Glu Arg
                325                 330                 335

Val His Ala Gln Val Gln Gln Phe Leu Lys Glu Gly Tyr Leu Arg Glu
                340                 345                 350

Glu Met Val Leu Asp Asn Ile Pro Lys Leu Leu Asn Cys Leu Arg Asp
                355                 360                 365

Cys Asn Val Ala Ile Arg Trp Leu Met Leu His Thr Ala Asp Ser Ala
                370                 375                 380

Cys Asp Pro Asn Asn Lys Arg Leu Arg Gln Ile Lys Asp Gln Ile Leu
385                 390                 395                 400

Thr Asp Ser Arg Tyr Asn Pro Arg Ile Leu Phe Gln Leu Leu Leu Asp
                405                 410                 415

Thr Ala Gln Phe Glu Phe Ile Leu Lys Glu Met Phe Lys Gln Met Leu
                420                 425                 430

Ser Glu Lys Gln Thr Lys Trp Glu His Tyr Lys Lys Glu Gly Ser Glu
                435                 440                 445

Arg Met Thr Glu Leu Ala Asp Val Phe Ser Gly Val Lys Pro Leu Thr
450                 455                 460
```

-continued

Arg Val Glu Lys Asn Glu Asn Leu Gln Ala Trp Phe Arg Glu Ile Ser
465                 470                 475                 480

Lys Gln Ile Leu Ser Leu Asn Tyr Asp Asp Ser Thr Ala Ala Gly Arg
                485                 490                 495

Lys Thr Val Gln Leu Ile Gln Ala Leu Glu Glu Val Gln Glu Phe His
            500                 505                 510

Gln Leu Glu Ser Asn Leu Gln Val Cys Gln Phe Leu Ala Asp Thr Arg
        515                 520                 525

Lys Phe Leu His Gln Met Ile Arg Thr Ile Asn Ile Lys Glu Glu Val
    530                 535                 540

Leu Ile Thr Met Gln Ile Val Gly Asp Leu Ser Phe Ala Trp Gln Leu
545                 550                 555                 560

Ile Asp Ser Phe Thr Ser Ile Met Gln Glu Ser Ile Arg Val Asn Pro
                565                 570                 575

Ser Met Val Thr Lys Leu Arg Ala Thr Phe Leu Lys Leu Ala Ser Ala
            580                 585                 590

Leu Asp Leu Pro Leu Leu Arg Ile Asn Gln Ala Asn Ser Pro Asp Leu
        595                 600                 605

Leu Ser Val Ser Gln Tyr Tyr Ser Gly Glu Leu Val Ser Tyr Val Arg
    610                 615                 620

Lys Val Leu Gln Ile Ile Pro Glu Ser Met Phe Thr Ser Leu Leu Lys
625                 630                 635                 640

Ile Ile Lys Leu Gln Thr His Asp Ile Ile Glu Val Pro Thr Arg Leu
                645                 650                 655

Asp Lys Asp Lys Leu Arg Asp Tyr Ala Gln Leu Gly Pro Arg Tyr Glu
            660                 665                 670

Val Ala Lys Leu Thr His Ala Ile Ser Ile Phe Thr Glu Gly Ile Leu
        675                 680                 685

Met Met Lys Thr Thr Leu Val Gly Ile Ile Lys Val Asp Pro Lys Gln
    690                 695                 700

Leu Leu Glu Asp Gly Ile Arg Lys Glu Leu Val Lys Arg Val Ala Phe
705                 710                 715                 720

Ala Leu His Arg Gly Leu Ile Phe Asn Pro Arg Ala Lys Pro Ser Glu
                725                 730                 735

Leu Met Pro Lys Leu Lys Glu Leu Gly Ala Thr Met Asp Gly Phe His
            740                 745                 750

Arg Ser Phe Glu Tyr Ile Gln Asp Tyr Val Asn Ile Tyr Gly Leu Lys
        755                 760                 765

Ile Trp Gln Glu Glu Val Ser Arg Ile Ile Asn Tyr Asn Val Glu Gln
    770                 775                 780

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Thr Pro Val Asp Glu
                805                 810                 815

Ser Val Thr Phe Ile Gly Arg Leu Cys Arg Glu Ile Leu Arg Ile Thr
            820                 825                 830

Asp Pro Lys Met Thr Cys His Ile Asp Gln Leu Asn Thr Trp Tyr Asp
        835                 840                 845

Met Lys Thr His Gln Glu Val Thr Ser Ser Arg Leu Phe Ser Glu Ile
    850                 855                 860

Gln Thr Thr Leu Gly Thr Phe Gly Leu Asn Gly Leu Asp Arg Leu Leu
865                 870                 875                 880

Cys Phe Met Ile Val Lys Glu Leu Gln Asn Phe Leu Ser Met Phe Gln

```
            885                 890                 895
Lys Ile Ile Leu Arg Asp Arg Thr Val Gln Asp Thr Leu Lys Thr Leu
            900                 905                 910
Met Asn Ala Val Ser Pro Leu Lys Ser Ile Val Ala Asn Ser Asn Lys
            915                 920                 925
Ile Tyr Phe Ser Ala Ile Ala Lys Thr Gln Lys Ile Trp Thr Ala Tyr
            930                 935                 940
Leu Glu Ala Ile Met Lys Val Gly Gln Met Gln Ile Leu Arg Gln Gln
945                 950                 955                 960
Ile Ala Asn Glu Leu Asn Tyr Ser Cys Arg Phe Asp Ser Lys His Leu
            965                 970                 975
Ala Ala Ala Leu Glu Asn Leu Asn Lys Ala Leu Leu Ala Asp Ile Glu
            980                 985                 990
Ala His Tyr Gln Asp Pro Ser Leu Pro Tyr Pro Lys Glu Asp Asn Thr
            995                1000                1005
Leu Leu Tyr Glu Ile Thr Ala Tyr Leu Glu Ala Gly Ile His Asn
           1010                1015                1020
Pro Leu Asn Lys Ile Tyr Ile Thr Thr Lys Arg Leu Pro Tyr Phe Pro
1025                1030                1035                1040
Ile Val Asn Phe Leu Phe Leu Ile Ala Gln Leu Pro Lys Leu Gln Tyr
                   1045                1050                1055
Asn Lys Asn Leu Gly Met Val Cys Arg Lys Pro Thr Asp Pro Val Asp
            1060                1065                1070
Trp Pro Pro Leu Val Leu Gly Leu Leu Thr Leu Leu Lys Gln Phe His
                   1075                1080                1085
Ser Arg Tyr Thr Glu Gln Phe Leu Ala Leu Ile Gly Gln Phe Ile Cys
            1090                1095                1100
Ser Thr Val Glu Gln Cys Thr Ser Gln Lys Ile Pro Glu Ile Pro Ala
1105                1110                1115                1120
Asp Val Val Gly Ala Leu Leu Phe Leu Glu Asp Tyr Val Arg Tyr Thr
                   1125                1130                1135
Lys Leu Pro Arg Arg Val Ala Glu Ala His Val Pro Asn Phe Ile Phe
                   1140                1145                1150
Asp Glu Phe Arg Thr Val Leu
           1155

<210> SEQ ID NO 28
<211> LENGTH: 1159
<212> TYPE: PRT
<213> ORGANISM: Mus musculus

<400> SEQUENCE: 28

Met Leu Asp Phe Leu Ala Glu Asn Asn Leu Cys Gly Gln Ala Ile Leu
1               5                   10                  15
Arg Ile Val Ser Cys Gly Asn Ala Ile Ile Ala Glu Val Leu Arg Leu
            20                  25                  30
Ser Glu Phe Ile Pro Ala Val Phe Leu Leu Lys Asp Arg Ala Asp Gln
            35                  40                  45
Gln Arg Tyr Gly Asp Ile Ile Phe Asp Phe Ser Tyr Phe Lys Gly Pro
        50                  55                  60
Glu Phe Trp Glu Ser Lys Leu Glu Ala Lys Pro Glu Leu Gln Asp Leu
65                  70                  75                  80
Asp Glu Glu Phe Arg Glu Asn Asn Ile Glu Ile Val Thr Arg Phe Tyr
                85                  90                  95
```

-continued

```
Leu Ala Phe Gln Ser Val His Lys Tyr Ile Val Asp Leu Asn Arg Tyr
            100                 105                 110

Leu Asp Asp Leu Asn Glu Gly Val Tyr Ile Gln Gln Thr Leu Glu Thr
            115                 120                 125

Val Leu Leu Ser Glu Asp Gly Lys Gln Leu Leu Cys Glu Ala Leu Tyr
            130                 135                 140

Leu Tyr Gly Val Met Leu Leu Val Ile Asp Gln Lys Ile Glu Gly Glu
145                 150                 155                 160

Val Arg Glu Arg Met Leu Val Ser Tyr Arg Tyr Ser Ala Ala Arg
            165                 170                 175

Ser Ser Ala Asp Ser Asn Met Asp Asp Ile Cys Lys Leu Leu Arg Ser
            180                 185                 190

Thr Gly Tyr Ser Ser Gln Pro Gly Ala Lys Arg Pro Asn Tyr Pro
            195                 200                 205

Glu Ser Tyr Phe Gln Arg Val Pro Ile Asn Glu Thr Phe Ile Ser Met
            210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Asn Gln Ala Ala
            245                 250                 255

Met Leu Tyr Val Ile Leu Tyr Phe Glu Pro Ser Ile Leu His Thr His
            260                 265                 270

Gln Ala Lys Met Arg Glu Ile Val Asp Lys Tyr Phe Pro Asp Asn Trp
            275                 280                 285

Val Ile Ser Ile Tyr Met Gly Ile Thr Val Asn Leu Ala Asp Ala Trp
            290                 295                 300

Glu Pro Tyr Lys Ala Ala Lys Thr Ala Leu Asn Asn Thr Leu Asp Leu
305                 310                 315                 320

Ala Asn Val Lys Glu Gln Ala Ser Arg Tyr Ala Ser Val Ser Asp Arg
            325                 330                 335

Val Arg Ala Gln Val Gln Phe Leu Lys Glu Gly Tyr Leu Arg Glu
            340                 345                 350

Glu Val Leu Leu Asp Asn Ile Pro Arg Leu Leu Asn Cys Leu Arg Asp
            355                 360                 365

Cys Asn Val Ala Ile Arg Trp Leu Met Leu His Thr Ala Asp Ser Ala
            370                 375                 380

Cys Asp Pro Asn Asn Lys Arg Leu Arg Gln Ile Lys Asp Gln Ile Leu
385                 390                 395                 400

Ala Asp Ser Arg Tyr Asn Pro Lys Ile Leu Phe Gln Leu Leu Leu Asp
            405                 410                 415

Thr Ala Gln Phe Glu Phe Ile Leu Lys Glu Met Phe Lys Gln Met Leu
            420                 425                 430

Ser Glu Lys Gln Ser Lys Trp Glu His Tyr Lys Lys Glu Gly Ser Glu
            435                 440                 445

Arg Met Thr Glu Leu Ala Asp Val Phe Ser Gly Val Lys Pro Leu Thr
450                 455                 460

Arg Val Glu Lys Asn Glu Asn Leu Gln Ala Trp Phe Arg Glu Ile Ser
465                 470                 475                 480

Lys Gln Ile Leu Ser Leu Asn Tyr Asp Asp Ser Thr Ala Ala Gly Arg
            485                 490                 495

Lys Thr Val Gln Leu Ile Gln Ala Leu Glu Glu Val Gln Glu Phe His
            500                 505                 510

Gln Leu Glu Ser Asn Leu Gln Val Cys Gln Phe Leu Ala Asp Thr Arg
```

-continued

```
            515                 520                 525
Lys Phe Leu His Gln Met Ile Arg Thr Ile Asn Ile Lys Glu Glu Val
            530                 535                 540
Leu Ile Thr Val Gln Ile Ile Gly Asp Leu Ser Phe Ala Trp Gln Leu
545                 550                 555                 560
Ile Asp Ser Phe Thr Ser Ile Met Gln Glu Ser Ile Arg Val Asn Pro
                565                 570                 575
Ser Met Val Thr Lys Leu Arg Ala Thr Phe Leu Lys Leu Ala Ser Ala
                580                 585                 590
Leu Asp Leu Pro Leu Leu Arg Ile Asn Gln Ala Asn Ser Pro Asp Leu
                595                 600                 605
Leu Ser Val Ser Gln Tyr Tyr Ser Gly Glu Leu Val Ser Tyr Val Arg
            610                 615                 620
Lys Val Leu Gln Ile Ile Pro Glu Ser Met Phe Thr Ser Leu Leu Lys
625                 630                 635                 640
Ile Ile Lys Leu Gln Thr His Asp Ile Met Glu Val Pro Thr Arg Leu
                645                 650                 655
Asp Lys Asp Lys Leu Arg Asp Tyr Ala Gln Leu Gly Pro Arg Tyr Glu
                660                 665                 670
Val Ala Lys Leu Thr His Ala Ile Ser Ile Phe Thr Glu Gly Ile Leu
            675                 680                 685
Met Met Lys Thr Thr Leu Val Gly Ile Ile Lys Val Asp Pro Lys Gln
            690                 695                 700
Leu Leu Glu Asp Gly Ile Arg Lys Glu Leu Val Lys Arg Val Ala Phe
705                 710                 715                 720
Ala Leu His Arg Gly Leu Ile Phe Asn Pro Arg Ala Lys Pro Ser Glu
                725                 730                 735
Leu Met Pro Lys Leu Lys Glu Leu Gly Ala Thr Met Asp Gly Phe His
                740                 745                 750
Arg Ser Phe Glu Tyr Ile Gln Asp Tyr Val Ser Ile Tyr Gly Leu Lys
            755                 760                 765
Ile Trp Gln Glu Glu Val Ser Arg Ile Ile Asn Tyr Asn Val Glu Gln
            770                 775                 780
Glu Cys Asn Asn Phe Leu Arg Thr Lys Ile Gln Asp Trp Gln Ser Met
785                 790                 795                 800
Tyr Gln Ser Thr His Ile Pro Ile Pro Lys Phe Ala Pro Val Asp Glu
                805                 810                 815
Ser Ile Thr Phe Ile Gly Arg Leu Cys Arg Glu Ile Leu Arg Ile Thr
                820                 825                 830
Asp Pro Lys Met Thr Cys Tyr Ile Asp Gln Leu Asn Thr Trp Tyr Asp
            835                 840                 845
Val Lys Thr His Gln Glu Val Thr Ser Ser Arg Leu Phe Ser Glu Ile
            850                 855                 860
Gln Thr Thr Leu Gly Thr Phe Gly Leu Asn Gly Leu Asp Arg Leu Leu
865                 870                 875                 880
Cys Phe Met Ile Val Lys Glu Leu Gln Asn Phe Leu Ser Met Phe Gln
                885                 890                 895
Lys Ile Ile Leu Lys Glu Arg Thr Val Gln Glu Thr Leu Lys Met Leu
                900                 905                 910
Met Ser Ala Val Asn Pro Leu Lys Ser Ile Val Ala Asn Ser Ser Lys
            915                 920                 925
Val Tyr Leu Ser Ala Ile Thr Lys Thr Gln Lys Ile Trp Ser Ala Tyr
            930                 935                 940
```

```
Leu Glu Ala Ile Met Lys Val Gly Gln Met Gln Ile Leu Arg Gln Gln
945                 950                 955                 960

Ile Ala Asn Glu Leu Asn Ser Ser Cys Arg Phe Asp Ser Arg His Leu
            965                 970                 975

Ala Ala Ala Leu Asp Asn Leu Asn Lys Ala Leu Leu Ala Asp Ile Glu
        980                 985                 990

Ala His Tyr Arg Asp Pro Ser Leu Pro Tyr Pro Lys Glu Asp Asn Thr
    995                 1000                1005

Leu Leu Tyr Glu Ile Thr Ala Tyr Leu Glu Ala Ala Gly Ile His Asn
    1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
                1045                1050                1055

Asn Lys Asn Leu Gly Met Val Cys Arg Lys Pro Ala Asp Pro Val Asp
                1060                1065                1070

Trp Pro Pro Leu Val Leu Gly Leu Leu Thr Leu Leu Lys Gln Phe His
        1075                1080                1085

Ser Arg Tyr Thr Glu Gln Phe Leu Ala Leu Ile Gly Gln Phe Ile Arg
    1090                1095                1100

Ser Thr Met Glu Gln Cys Thr Ser Gln Lys Met Pro Glu Met Pro Ala
1105                1110                1115                1120

Asp Ala Val Gly Ala Leu Leu Phe Leu Glu Asp Tyr Val Arg Tyr Thr
                1125                1130                1135

Lys Leu Pro Arg Arg Val Ala Glu Ala His Val Pro Asn Phe Ile Phe
                1140                1145                1150

Asp Glu Phe Arg Thr Val Leu
        1155

<210> SEQ ID NO 29
<211> LENGTH: 902
<212> TYPE: PRT
<213> ORGANISM: Rattus norvegicus

<400> SEQUENCE: 29

Met Ser Phe Lys Gly Val Arg Lys Ile Arg Val Gly His Phe Val Phe
1               5                   10                  15

Tyr Ala Asp Ala Gly Gln Ile Leu Ser Asp Ser Leu Leu Ser Gln Val
                20                  25                  30

Ile Ser Ile Tyr Met Gly Ile Thr Val Asn Leu Ala Asp Ala Trp Glu
            35                  40                  45

Pro Tyr Lys Ala Ala Lys Thr Ala Leu Asn Asn Thr Leu Asp Leu Pro
        50                  55                  60

Asn Val Lys Glu Gln Ala Ser Arg Tyr Ala Ser Val Ser Glu Arg Val
65                  70                  75                  80

Arg Ala Gln Val Gln Gln Phe Lys Glu Gly Tyr Leu Arg Glu Glu
                85                  90                  95

Val Leu Leu Asp Asn Ile Pro Arg Leu Asn Cys Leu Arg Asp Cys
                100                 105                 110

Asn Val Ala Ile Arg Trp Leu Met Leu His Thr Ala Asp Ser Ala Cys
            115                 120                 125

Asp Pro Asn Asn Lys Arg Leu Arg Gln Ile Lys Asp Gln Ile Leu Ala
        130                 135                 140

Asp Ser Arg Tyr Asn Pro Lys Ile Leu Phe Gln Leu Leu Leu Asp Thr
```

-continued

```
                145                 150                 155                 160
Ala Gln Phe Glu Phe Ile Leu Lys Glu Met Phe Lys Gln Met Leu Ser
                    165                 170                 175
Glu Lys Gln Ser Lys Trp Glu His Tyr Lys Lys Glu Gly Ser Glu Arg
                    180                 185                 190
Met Ile Glu Leu Ala Asp Val Phe Ser Gly Val Lys Pro Leu Thr Arg
                    195                 200                 205
Val Glu Lys Asn Glu Asn Leu Gln Ala Trp Phe Arg Glu Ile Ser Lys
210                 215                 220
Gln Ile Leu Ser Leu Asn Tyr Asp Asp Ser Thr Ala Ala Gly Arg Lys
225                 230                 235                 240
Thr Val Gln Leu Ile Gln Ala Leu Glu Glu Val Gln Glu Phe His Gln
                    245                 250                 255
Leu Glu Ser Asn Leu Gln Val Cys Gln Phe Leu Ala Asp Thr Arg Lys
                    260                 265                 270
Phe Leu His Gln Met Ile Arg Thr Ile Asn Ile Lys Glu Glu Val Leu
                    275                 280                 285
Ile Thr Met Gln Ile Val Gly Asp Leu Ser Phe Ala Trp Gln Leu Ile
                    290                 295                 300
Asp Ser Phe Thr Ser Ile Met Gln Glu Ser Ile Arg Val Asn Pro Ser
305                 310                 315                 320
Met Val Thr Lys Leu Arg Ala Thr Phe Leu Lys Leu Ala Ser Ala Leu
                    325                 330                 335
Asp Leu Pro Leu Leu Arg Ile Asn Gln Ala Asn Ser Pro Asp Leu Leu
                    340                 345                 350
Ser Val Ser Gln Tyr Tyr Ser Gly Glu Leu Val Ser Tyr Val Arg Lys
                    355                 360                 365
Val Leu Gln Ile Ile Pro Glu Ser Met Phe Thr Ser Leu Leu Lys Ile
                    370                 375                 380
Ile Lys Leu Gln Thr His Asp Ile Ile Glu Val Pro Thr Arg Leu Asp
385                 390                 395                 400
Lys Asp Lys Leu Arg Asp Tyr Ala Gln Leu Gly Pro Arg Tyr Glu Val
                    405                 410                 415
Ala Lys Leu Thr His Ala Ile Ser Ile Phe Thr Glu Gly Ile Leu Met
                    420                 425                 430
Met Lys Thr Thr Leu Val Gly Ile Ile Lys Val Asp Pro Lys Gln Leu
                    435                 440                 445
Leu Glu Asp Gly Ile Arg Lys Glu Leu Val Lys Arg Val Ala Phe Ala
                    450                 455                 460
Leu His Arg Gly Leu Ile Phe Asn Pro Arg Ala Lys Pro Ser Glu Leu
465                 470                 475                 480
Met Pro Lys Leu Lys Glu Leu Gly Ala Thr Met Asp Gly Phe His Arg
                    485                 490                 495
Ser Phe Glu Tyr Ile Gln Asp Tyr Val Asn Ile Tyr Gly Leu Lys Ile
                    500                 505                 510
Trp Gln Glu Glu Val Ser Arg Ile Ile Asn Tyr Asn Val Glu Gln Glu
                    515                 520                 525
Cys Asn Asn Phe Leu Arg Thr Lys Ile Gln Asp Trp Gln Ser Ile Tyr
                    530                 535                 540
Gln Ser Thr His Ile Pro Ile Pro Lys Phe Ala Pro Val Asp Glu Ser
545                 550                 555                 560
Ile Thr Phe Ile Gly Arg Leu Cys Arg Glu Ile Leu Arg Ile Thr Asp
                    565                 570                 575
```

```
Pro Lys Val Thr Cys Tyr Ile Asp Gln Leu Asn Thr Trp Tyr Asp Met
            580                 585                 590

Lys Thr Arg Gln Glu Val Thr Ser Arg Leu Phe Ser Glu Ile Gln
        595                 600                 605

Thr Thr Leu Gly Thr Phe Gly Leu Asn Gly Leu Asp Arg Leu Cys
        610                 615                 620

Phe Met Ile Val Lys Glu Leu Gln Asn Phe Leu Ser Met Phe Gln Lys
625                 630                 635                 640

Ile Ile Leu Arg Glu Arg Thr Val Gln Glu Thr Leu Lys Thr Leu Met
            645                 650                 655

Asn Ala Val Ser Pro Leu Arg Ser Ile Val Ala Asn Ser Ser Lys Val
            660                 665                 670

Tyr Leu Ala Ala Ile Thr Lys Thr Gln Lys Ile Trp Ser Thr Tyr Leu
            675                 680                 685

Glu Ala Ile Met Lys Val Gly Gln Met Gln Ile Leu Arg Arg Gln Ile
            690                 695                 700

Ala Asn Glu Leu Asn Ser Ser Cys Arg Phe Asp Ser Arg His Leu Ala
705                 710                 715                 720

Ala Ala Leu Asp Asn Leu Asn Lys Ala Leu Leu Ala Asp Ile Glu Ala
            725                 730                 735

His Tyr Arg Asp Pro Ser Leu Pro Tyr Pro Lys Glu Asp Asn Thr Leu
            740                 745                 750

Leu Tyr Glu Ile Thr Ala Tyr Leu Glu Ala Ala Gly Ile His Asn Pro
            755                 760                 765

Leu Asn Lys Ile Tyr Ile Thr Thr Lys Arg Leu Pro Tyr Phe Pro Ile
            770                 775                 780

Val Asn Phe Leu Phe Leu Ile Ala Gln Leu Pro Lys Leu Gln Tyr Asn
785                 790                 795                 800

Lys Asn Leu Gly Met Val Cys Arg Lys Pro Ala Asp Pro Val Asp Trp
                805                 810                 815

Pro Pro Leu Val Leu Gly Leu Leu Thr Leu Leu Lys Gln Phe His Ser
                820                 825                 830

Arg Tyr Thr Glu Gln Phe Leu Ala Leu Ile Gly Gln Phe Ile Arg Ser
            835                 840                 845

Thr Met Glu Gln Cys Thr Ser Gln Lys Met Pro Glu Met Pro Ala Asp
850                 855                 860

Ala Val Gly Ala Leu Leu Phe Leu Glu Asp Tyr Val Arg Tyr Thr Lys
865                 870                 875                 880

Leu Pro Arg Arg Val Ala Glu Ala His Val Pro Asn Phe Ile Phe Asp
                885                 890                 895

Glu Phe Arg Thr Val Leu
            900

<210> SEQ ID NO 30
<211> LENGTH: 1389
<212> TYPE: PRT
<213> ORGANISM: Canis familiaris

<400> SEQUENCE: 30

Met Glu Arg Arg Arg Leu Gly Glu Gly Ala Ala Cys Pro Ser Leu Arg
  1               5                  10                  15

Ala Arg Arg Ala Glu Pro Gly Pro Gln Pro Gly Arg Thr Asp Pro Ser
            20                  25                  30

Ser Gly His Pro Arg Gly Ala Pro Arg Gly Gly Asp Thr Cys Arg His
```

```
            35                  40                  45
Pro Arg Pro Arg His Pro Pro Leu Pro Pro Tyr Leu Glu Ala Arg Pro
 50                  55                  60

Gly Ser Val Trp Gln His Pro Asp Arg Pro Arg Pro Asp Pro Asn Ser
 65                  70                  75                  80

Phe Leu Asn Ser Leu Pro Gln Ser Leu Lys Pro Arg Ala Arg Ala Arg
                 85                  90                  95

Ala Ser Ser Ala Val Ala Gly Gln Arg Ser His Asp Ala Pro Pro Cys
                100                 105                 110

Ser Arg Pro Leu Trp Ser Cys Asp Cys His Gly Arg His Arg Arg Lys
                115                 120                 125

Pro Gly Ser Arg Arg Leu Ala Ile Gly Gly Cys Gly Arg Arg Gly Arg
130                 135                 140

Pro Glu Asn Asn Leu Cys Gly Gln Ala Ile Leu Arg Ile Val Ser Cys
145                 150                 155                 160

Gly Asn Ala Ile Ile Ala Glu Leu Leu Arg Leu Ser Glu Phe Ile Pro
                165                 170                 175

Ala Val Phe Arg Leu Lys Asp Arg Ala Asp Gln Gln Lys Tyr Gly Asp
                180                 185                 190

Ile Ile Phe Asp Phe Ser Tyr Phe Lys Gly Pro Glu Leu Trp Glu Ser
                195                 200                 205

Lys Leu Glu Ala Lys Pro Glu Leu Gln Asp Leu Asp Glu Glu Phe Arg
210                 215                 220

Glu Asn Asn Ile Glu Ile Val Thr Arg Phe Tyr Leu Ala Phe Gln Ser
225                 230                 235                 240

Val His Lys Tyr Ile Val Asp Leu Asn Arg Tyr Leu Asp Asp Leu Asn
                245                 250                 255

Glu Gly Val Tyr Ile Gln Gln Thr Leu Glu Thr Val Leu Leu Asn Glu
                260                 265                 270

Asp Gly Lys Gln Leu Leu Cys Glu Ala Leu Tyr Leu Tyr Gly Val Met
                275                 280                 285

Leu Leu Val Ile Asp Gln Lys Ile Glu Gly Glu Val Arg Glu Arg Met
                290                 295                 300

Leu Val Ser Tyr Tyr Arg Tyr Ser Ala Ala Arg Ser Ser Ala Asp Ser
305                 310                 315                 320

Asn Met Asp Asp Ile Cys Lys Leu Leu Arg Ser Thr Gly Tyr Ser Ser
                325                 330                 335

Gln Pro Gly Ala Lys Arg Pro Pro Asn Tyr Pro Glu Ser Tyr Phe Gln
                340                 345                 350

Arg Val Pro Ile Asn Glu Ala Phe Ile Ser Met Val Ile Gly Arg Leu
                355                 360                 365

Arg Ser Asp Asp Ile Tyr Asn Gln Val Ser Ala Tyr Pro Leu Pro Glu
                370                 375                 380

His Arg Ser Thr Ala Leu Ala Thr Gln Ala Ala Met Leu Tyr Val Ile
385                 390                 395                 400

Leu Tyr Phe Glu Pro Ser Ile Leu His Thr His Gln Ala Lys Met Arg
                405                 410                 415

Glu Ile Val Asp Lys Tyr Phe Pro Asp Asn Trp Val Ile Ser Ile Tyr
                420                 425                 430

Met Gly Ile Thr Val Asn Leu Ala Asp Ala Trp Glu Pro Tyr Lys Ala
                435                 440                 445

Ala Lys Thr Ala Leu Asn Asn Thr Leu Asp Leu Ser Asn Val Arg Glu
                450                 455                 460
```

```
Gln Ser Ser Arg Tyr Ala Thr Val Ser Glu Arg Val His Ala Gln Val
465                 470                 475                 480

Gln Gln Phe Leu Lys Glu Gly Tyr Leu Arg Glu Met Val Leu Asp
                    485                 490                 495

Asn Ile Pro Arg Leu Leu Asn Cys Leu Arg Asp Cys Asn Val Ala Ile
                500                 505                 510

Arg Trp Leu Met Leu His Thr Ala Asp Ser Ala Cys Asp Pro Asn Asn
                515                 520                 525

Lys Arg Leu Arg Gln Ile Lys Asp Gln Ile Leu Thr Asp Ser Arg Tyr
530                 535                 540

Asn Pro Lys Ile Leu Phe Gln Leu Leu Leu Asp Thr Ala Gln Phe Glu
545                 550                 555                 560

Phe Ile Leu Lys Glu Met Phe Lys Gln Met Leu Ser Glu Lys Gln Ala
                565                 570                 575

Lys Trp Glu His Tyr Lys Lys Glu Ser Ser Glu Arg Met Thr Glu Leu
                580                 585                 590

Ala Asp Val Phe Ser Gly Val Lys Pro Leu Thr Arg Val Glu Lys Asn
            595                 600                 605

Gly Asn Cys Arg Arg Asn Ile Gly Val Leu Glu Met Tyr Thr Gln
610                 615                 620

Ile Thr Gly Lys Gln Gln Lys Asn Leu Gln Ala Trp Phe Arg Glu Ile
625                 630                 635                 640

Ser Lys Gln Ile Leu Ser Leu Asn His Asp Asp Ser Thr Ala Ala Gly
                645                 650                 655

Arg Lys Thr Val Gln Leu Ile Gln Ala Leu Glu Glu Val Gln Glu Phe
                660                 665                 670

His Gln Leu Glu Ser Asn Leu Gln Val Cys Gln Phe Leu Ala Asp Thr
                675                 680                 685

Arg Lys Phe Leu His Gln Met Ile Arg Thr Ile Asn Ile Lys Glu Glu
                690                 695                 700

Val Leu Ile Thr Met Gln Ile Val Gly Asp Leu Ser Phe Ala Trp Gln
705                 710                 715                 720

Leu Ile Asp Ser Phe Thr Asp Ile Met Gln Glu Ser Ile Arg Val Asn
                725                 730                 735

Pro Ser Met Val Thr Lys Leu Arg Ala Thr Phe Leu Lys Leu Ala Ser
                740                 745                 750

Ala Leu Asp Leu Pro Leu Leu Arg Ile Asn Gln Ala Asn Ser Pro Asp
                755                 760                 765

Leu Leu Ser Val Ser Gln Tyr Tyr Ser Gly Glu Leu Val Ser Tyr Val
                770                 775                 780

Arg Lys Val Leu Gln Ile Ile Pro Glu Ser Met Phe Thr Ser Leu Leu
785                 790                 795                 800

Lys Ile Ile Lys Leu Gln Thr His Asp Ile Ile Glu Val Pro Thr Arg
                805                 810                 815

Leu Asp Lys Asp Lys Leu Arg Asp Tyr Ala Gln Leu Gly Pro Arg Tyr
                820                 825                 830

Glu Val Ala Cys Pro Phe Asp Phe Cys Leu Leu Ile Phe Asn Thr Gln
                835                 840                 845

Pro Met Thr Arg His Lys Ser Ala Leu Pro Ala Val Ala Lys Leu Thr
                850                 855                 860

His Ala Ile Ser Ile Phe Thr Glu Gly Ile Leu Met Met Lys Thr Thr
865                 870                 875                 880
```

-continued

Leu Val Gly Ile Ile Lys Val Asp Pro Lys Gln Leu Glu Asp Gly
                885                 890                 895

Ile Arg Lys Glu Leu Val Lys Arg Val Ala Phe Ala Leu His Arg Gly
        900                 905                 910

Leu Ile Phe Asn Pro Arg Ala Lys Pro Ser Glu Leu Met Pro Lys Leu
        915                 920                 925

Lys Glu Leu Gly Ala Thr Met Asp Gly Phe His Arg Ser Phe Glu Tyr
        930                 935                 940

Ile Gln Asp Tyr Val Asn Ile Tyr Gly Leu Lys Ile Trp Gln Glu Glu
945                 950                 955                 960

Val Ser Arg Ile Ile Asn Tyr Asn Val Glu Gln Glu Cys Asn Asn Phe
                965                 970                 975

Leu Arg Thr Lys Ile Gln Asp Trp Gln Ser Met Tyr Gln Ser Thr His
        980                 985                 990

Ile Pro Ile Pro Lys Phe Pro Pro Val Asp Glu Ser Val Thr Phe Ile
        995                 1000                1005

Gly Arg Leu Cys Arg Glu Ile Leu Arg Ile Thr Asp Pro Lys Met Thr
        1010                1015                1020

Cys His Ile Asp Gln Leu Asn Thr Trp Tyr Asp Met Lys Thr His Gln
1025                1030                1035                1040

Glu Val Thr Ser Ser Arg Leu Phe Ser Glu Ile Gln Thr Thr Leu Gly
        1045                1050                1055

Thr Phe Gly Leu Asn Gly Leu Asp Arg Leu Leu Cys Phe Met Ile Val
        1060                1065                1070

Lys Glu Leu Gln Asn Phe Leu Ser Met Phe Gln Lys Ile Ile Leu Arg
        1075                1080                1085

Asp Arg Thr Val Gln Asp Thr Leu Lys Thr Leu Met Asn Ala Val Ser
        1090                1095                1100

Pro Leu Lys Ser Ile Val Ala Asn Ser Asn Lys Ile Tyr Phe Ser Ala
1105                1110                1115                1120

Ile Ala Lys Thr Gln Lys Ile Trp Thr Ala Tyr Leu Glu Ala Ile Met
        1125                1130                1135

Lys Val Gly Gln Met Gln Ile Leu Arg Gln Gln Ile Ala Asn Glu Leu
        1140                1145                1150

Asn Tyr Ser Cys Arg Phe Asp Ser Lys His Leu Ala Ala Ala Leu Glu
        1155                1160                1165

Asn Leu Asn Lys Ala Leu Leu Ala Asp Ile Glu Ala His Tyr Gln Asp
        1170                1175                1180

Pro Ser Leu Pro Tyr Pro Lys Glu Asp Asn Thr Leu Leu Tyr Glu Ile
1185                1190                1195                1200

Thr Ala Tyr Leu Glu Ala Ala Gly Ile His Asn Pro Leu Asn Lys Val
        1205                1210                1215

Ser Val Gln Ile Met Glu Gln Ile Tyr Ile Thr Thr Lys Arg Leu Pro
        1220                1225                1230

Tyr Phe Pro Val Val Asn Phe Leu Phe Leu Ile Ala Gln Leu Pro Lys
        1235                1240                1245

Leu Gln Tyr Asn Lys Asn Leu Gly Met Val Cys Arg Lys Pro Ala Asp
        1250                1255                1260

Pro Val Asp Trp Pro Pro Leu Val Leu Gly Leu Leu Thr Leu Leu Lys
1265                1270                1275                1280

Gln Phe His Ser Arg Tyr Thr Glu Gln Phe Leu Ala Leu Ile Gly Gln
        1285                1290                1295

Phe Ile Arg Ser Thr Val Glu Gln Cys Thr Ser Gln Lys Ile Pro Glu

```
                    1300                1305                1310

Met Pro Ala Asp Val Gly Ala Leu Leu Phe Leu Glu Asp Tyr Val
                    1315                1320                1325

Arg Cys Gly Gly Glu Arg Cys Ile Ala Ala Pro Ala Ala Pro Leu
                    1330                1335                1340

Leu Ser Ser Ala Arg Lys Ser Asp Pro Gly Val Arg Asn Ser Arg Asn
1345                1350                1355                1360

Thr Gly Gln Gln Phe Met Glu Trp Pro Thr His Leu Cys Ile Gln Pro
                    1365                1370                1375

Leu Pro Val Thr Arg Leu Ala Pro Lys Asp Ile Phe Ile
                    1380                1385

<210> SEQ ID NO 31
<211> LENGTH: 1156
<212> TYPE: PRT
<213> ORGANISM: Gallus gallus

<400> SEQUENCE: 31

Met Val Asp Phe Leu Ala Glu Asn Asn Leu Cys Gly Gln Ala Ile Leu
1               5                   10                  15

Arg Ile Val Ser Cys Gly Asn Ala Ile Ile Ala Glu Leu Leu Arg Leu
                20                  25                  30

Ser Glu Phe Ile Pro Gly Val Phe Arg Leu Lys Asp Lys Ala Asp Gln
                35                  40                  45

Gln Lys Tyr Gly Asp Ile Ile Phe Asp Phe Ser Tyr Phe Lys Gly Pro
        50                  55                  60

Glu Ala Cys Glu Gly Arg Leu Glu Ala Lys Pro Glu Leu Leu Asp Leu
65                  70                  75                  80

Asp Glu Glu Phe Arg Glu Asn Asn Ile Glu Ile Leu Thr Arg Phe Tyr
                85                  90                  95

Leu Ala Phe Gln Ser Val His Lys Tyr Ile Ile Asp Leu Asn Ser Ala
                100                 105                 110

Ala Arg Ser Ser Ala Asp Ser Asn Leu Asp Asp Ile Cys Lys Leu Leu
            115                 120                 125

Arg Ser Thr Gly Tyr Ser Ser Gln Pro Gly Ala Lys Arg Pro Pro Asn
        130                 135                 140

Tyr Pro Glu Ser Tyr Phe Ser Arg Val Pro Ile Ser Glu Thr Phe Ile
145                 150                 155                 160

Ser Met Val Val Gly Arg Leu Arg Ser Asp Asp Ile Tyr Asn Gln Val
                165                 170                 175

Ser Ala Tyr Pro Leu Pro Glu His Arg Ser Thr Ala Leu Ala Thr Gln
                180                 185                 190

Ala Ala Met Leu Tyr Val Ile Leu Tyr Phe Asp Ala Ser Ile Leu His
            195                 200                 205

Thr Gln Gln Ala Lys Met Arg Glu Ile Val Asp Lys Tyr Phe Pro Asp
        210                 215                 220

Asn Trp Val Ile Ser Ile Tyr Met Gly Ile Thr Val Asn Leu Ala Glu
225                 230                 235                 240

Ala Trp Glu Pro Tyr Lys Ala Ala Lys Thr Ala Leu Asn Tyr Thr Leu
                245                 250                 255

Asp Ile Ala Asn Val Lys Glu Gln Ala Asn Arg Tyr Ala Ala Val Thr
                260                 265                 270

Glu Arg Val His Thr Gln Val Gln Gln Phe Leu Lys Glu Gly Cys Leu
            275                 280                 285
```

```
Arg Glu Glu Leu Val Leu Asp Asn Ile Pro Lys Leu Leu Asn Tyr Leu
    290                 295                 300

Arg Asp Cys Asn Val Ala Ile Arg Trp Leu Met Leu His Thr Ala Asp
305                 310                 315                 320

Thr Ala Cys Asp Pro Asn Asn Lys Arg Leu Arg Gln Ile Lys Asp Gln
                325                 330                 335

Ile Leu Thr Asp Ser Arg Tyr Asn Pro Lys Val Leu Phe Gln Leu Leu
            340                 345                 350

Leu Asp Thr Ala Gln Phe Glu Phe Ile Leu Lys Glu Met Phe Lys Gln
            355                 360                 365

Met Leu Ser Glu Lys Gln Ala Lys Trp Glu Asn Tyr Lys Lys Glu Gly
370                 375                 380

Ser Glu Arg Met Thr Glu Leu Ala Asp Val Phe Ser Gly Val Lys Pro
385                 390                 395                 400

Leu Thr Arg Val Glu Lys Asn Glu Asn Leu Gln Ala Trp Phe Arg Glu
                405                 410                 415

Ile Ser Lys Gln Ile Met Ser Leu Asn Tyr Asp Asp Ser Thr Ala Ala
            420                 425                 430

Gly Arg Lys Thr Val Gln Leu Ile Gln Ala Leu Glu Glu Val Gln Glu
            435                 440                 445

Phe His Gln Leu Glu Thr Asn Leu Gln Val Cys Gln Phe Leu Ala Asp
    450                 455                 460

Thr Arg Lys Phe Leu His Gln Met Ile Arg Thr Ile Asn Ile Lys Glu
465                 470                 475                 480

Glu Val Leu Ile Thr Met Gln Ile Val Gly Asp Leu Ser Tyr Ala Trp
                485                 490                 495

Gln Leu Ile Asp Ser Phe Thr Ser Ile Met Gln Glu Ser Ile Arg Val
            500                 505                 510

Ser Pro Ser Met Val Thr Lys Leu Arg Ala Thr Phe Leu Lys Leu Ala
            515                 520                 525

Ser Ala Leu Asp Leu Pro Leu Leu Arg Ile Asn Gln Ala Asn Ser Pro
    530                 535                 540

Asp Leu Leu Ser Val Ser Gln Tyr Tyr Ser Gly Glu Leu Val Ser Tyr
545                 550                 555                 560

Val Arg Lys Val Leu Gln Ile Ile Pro Glu Ser Met Phe Thr Ser Leu
                565                 570                 575

Leu Lys Ile Ile Lys Leu Gln Thr His Asp Ile Ile Glu Val Pro Thr
            580                 585                 590

Arg Leu Asp Lys Asp Lys Leu Arg Asp Tyr Ala Gln Leu Gly Pro Arg
            595                 600                 605

Tyr Glu Val Ala Lys Leu Thr His Ala Ile Ser Ile Phe Thr Glu Gly
    610                 615                 620

Ile Leu Met Met Lys Thr Thr Leu Val Gly Ile Ile Lys Val Asp Pro
625                 630                 635                 640

Lys Gln Leu Leu Glu Asp Gly Ile Arg Lys Glu Leu Val Lys Arg Val
                645                 650                 655

Ala Leu Ala Leu His Arg Gly Leu Ile Phe Asn Pro Arg Ala Lys Pro
            660                 665                 670

Ser Glu Leu Met Pro Lys Leu Lys Glu Met Ala Ala Thr Met Asp Gly
            675                 680                 685

Phe His Arg Ser Phe Glu Tyr Ile Gln Asp Tyr Val Asn Ile Tyr Gly
    690                 695                 700

Leu Lys Ile Trp Gln Glu Glu Val Ser Arg Ile Ile Asn Tyr Asn Val
```

-continued

```
            705                 710                 715                 720
Glu Gln Glu Cys Asn Asn Phe Leu Arg Thr Lys Ile Gln Asp Trp Gln
                725                 730                 735

Ser Ile Tyr Gln Ser Thr His Ile Pro Ile Pro Lys Phe Thr Pro Val
                740                 745                 750

Asp Glu Ser Val Thr Phe Ile Gly Arg Leu Cys Arg Glu Ile Leu Arg
                755                 760                 765

Ile Thr Asp Pro Lys Ile Thr Cys Tyr Ile Asp Gln Met Asn Thr Trp
            770                 775                 780

Tyr Asp Val Lys Thr His Gln Glu Val Thr Ser Ser Arg Leu Phe Ser
785                 790                 795                 800

Glu Ile Gln Asp Thr Leu Gly Thr Phe Gly Leu Asn Gly Leu Asp Arg
                805                 810                 815

Leu Leu Cys Phe Met Ile Val Lys Glu Leu Gln Asn Phe Leu Ser Met
                820                 825                 830

Phe Gln Lys Asn Val Leu Arg Asp Arg Thr Val Gln Asp Thr Leu Lys
                835                 840                 845

Ala Leu Met Asn Ala Val Ser Pro Leu Lys Gly Ile Ile Ala Asn Ser
                850                 855                 860

Asn Lys Val Tyr Ser Ala Ala Ile Ala Lys Thr Gln Lys Ile Trp Thr
865                 870                 875                 880

Ala Tyr Leu Asp Ser Ile Met Lys Val Gly Gln Met Gln Ile Leu Arg
                885                 890                 895

Arg Gln Ile Thr Asn Glu Leu Asn Tyr Ser Cys Arg Phe Asp Ser Lys
                900                 905                 910

His Leu Ala Ala Ala Leu Glu Asn Leu Asn Lys Ala Ile Leu Ala Asp
                915                 920                 925

Ile Glu Ala His Tyr Gln Asn Pro Ser Leu Pro Tyr Pro Lys Glu Asp
            930                 935                 940

Asn Thr Leu Leu Tyr Glu Ile Thr Ala Tyr Leu Glu Ala Ala Gly Ile
945                 950                 955                 960

His Asn Pro Leu Asn Lys Ile Tyr Ile Thr Thr Lys Arg Leu Pro Tyr
                965                 970                 975

Phe Pro Thr Val Asn Phe Leu Phe Leu Ile Ser Gln Phe Pro Lys Leu
                980                 985                 990

Gln Tyr Ser Lys Asn Leu Gly Val Val Cys Lys Arg Pro Ala Asp Gln
                995                 1000                1005

Ile Asp Trp Leu Pro Leu Val Leu Gly Leu Leu Thr Leu Leu Lys Gln
            1010                1015                1020

Phe His Ser Arg Tyr Thr Glu Gln Phe Leu Thr Leu Ile Gly Gln Phe
1025                1030                1035                1040

Ile Arg Ser Thr Met Glu Gln Cys Met Ser Gln Lys Ile Pro Glu Met
                1045                1050                1055

Pro Ala Asp Val Val Ala Ala Leu Met Phe Leu Glu Asp Tyr Ile Arg
                1060                1065                1070

Tyr Thr Lys Leu Pro Arg Lys Gly Asp Ser Ser Val Thr Leu Val
            1075                1080                1085

Pro Tyr Thr Val Ser Val Cys Gly Leu Leu Gly Ala Gly Thr Gly Thr
            1090                1095                1100

Arg Trp Asp Gly Ala Leu Gly Cys Leu Gly Lys Lys Thr Asn Ile
1105                1110                1115                1120

Pro Phe Pro Leu Pro His Asn Tyr Leu Gln Phe Leu Gly Tyr His Val
                1125                1130                1135
```

```
Ala Thr Glu Lys Ala Gln Leu Ser Ala Tyr Ser Ser Pro Phe Asn Thr
            1140                1145                1150

Asn Met Gly Ile
        1155

<210> SEQ ID NO 32
<211> LENGTH: 1159
<212> TYPE: PRT
<213> ORGANISM: Xenopus tropicalis

<400> SEQUENCE: 32

Met Val Asp Phe Leu Ala Glu Asn Asn Leu Cys Gly Gln Ala Ile Leu
  1               5                  10                  15

Arg Ile Val Ser Arg Gly Asn Ala Ile Ile Ala Glu Leu Leu Arg Leu
             20                  25                  30

Ser Glu Phe Val Pro Ser Val Phe Arg Leu Lys Asp Lys Ala Asp Gln
         35                  40                  45

Gln Lys Tyr Gly Asp Ile Ile Phe Asp Phe Ser Tyr Phe Lys Gly Pro
     50                  55                  60

Glu Val Cys Glu Gly Arg Leu Glu Ala Lys Pro Glu Leu Gln Asp Leu
 65                  70                  75                  80

Asp Glu Glu Phe Arg Glu Asn Asn Ile Glu Ile Leu Thr Arg Phe Tyr
                 85                  90                  95

Leu Ala Phe Glu Ser Val His Lys Tyr Ile Val Asp Leu Asn Arg Tyr
            100                 105                 110

Leu Glu Asp Leu Asn Glu Gly Ile Tyr Ile Gln Gln Thr Leu Glu Thr
        115                 120                 125

Val Leu Leu Asn Glu Asp Gly Lys Gln Leu Leu Cys Glu Ala Leu Tyr
    130                 135                 140

Leu Tyr Gly Val Met Leu Leu Val Ile Asp Gln Lys Ile Glu Gly Glu
145                 150                 155                 160

Val Arg Glu Arg Met Leu Val Ala Tyr Tyr Arg Tyr Ser Ala Ala Arg
                165                 170                 175

Ser Ser Val Asp Ser Asn Met Asp Asp Ile Cys Lys Leu Leu Arg Ser
            180                 185                 190

Thr Gly Tyr Ser Ser Gln Pro Gly Ala Lys Arg Pro Pro Asn Tyr Pro
        195                 200                 205

Glu Ser Tyr Phe Ser Arg Val Pro Ile Ser Glu Thr Phe Ile Ser Met
    210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Thr Gln Ala Ala
                245                 250                 255

Ile Leu Tyr Val Ile Leu Tyr Phe His Pro Pro Thr Leu His Thr His
            260                 265                 270

Gln Ala Lys Met Arg Glu Ile Val Asp Lys Tyr Phe Pro Asp Asn Trp
        275                 280                 285

Val Ile Ser Ile Tyr Met Gly Ile Thr Val Asn Leu Met Glu Val Trp
    290                 295                 300

Glu Pro Tyr Lys Ala Ala Lys Thr Ala Leu Asn Tyr Thr Leu Asp Leu
305                 310                 315                 320

Pro Asn Ile Lys Glu Gln Ala Ser Arg Tyr Ala Lys Ile Ile Glu Ser
                325                 330                 335

Leu His Pro Gln Val Gln Gln Phe Leu Lys Glu Gly Phe Leu Arg Glu
```

-continued

```
                340                 345                 350
Glu Phe Val Leu Asp Asn Ile Pro Lys Leu Leu Asn Cys Leu Arg Asp
            355                 360                 365
Cys Asn Val Ala Ile Arg Trp Leu Met Leu His Thr Ala Asp Ser Ala
        370                 375                 380
Tyr Asp Pro Asn Asn Lys Arg Leu Arg Gln Val Lys Asp Gln Val Leu
385                 390                 395                 400
Ala Asp Ser Lys Tyr Asn Pro Lys Ile Leu Phe Gln Leu Leu Leu Asp
                405                 410                 415
Thr Ala Gln Phe Glu Phe Leu Leu Lys Glu Met Phe Lys Gln Met Leu
            420                 425                 430
Ser Glu Lys Gln Asn Lys Trp Glu Ser Tyr Lys Lys Glu Gly Ser Glu
        435                 440                 445
Arg Met Thr Glu Leu Ala Asp Val Phe Ser Gly Val Lys Pro Leu Thr
    450                 455                 460
Arg Val Glu Lys Asn Glu His Leu Gln Ala Trp Phe Arg Glu Ile Ala
465                 470                 475                 480
Lys Gln Ile His Ser Leu Asn Tyr Asp Asp Ser Thr Ala Ala Gly Arg
                485                 490                 495
Lys Thr Val Gln Leu Ile Gln Ala Leu Glu Val Gln Glu Phe His
            500                 505                 510
Gln Leu Glu Thr Asn Leu Gln Val Cys Gln Phe Leu Ala Asp Thr Arg
        515                 520                 525
Lys Phe Leu His Gln Met Ile Arg Thr Ile Asn Ile Lys Glu Glu Val
    530                 535                 540
Leu Ile Thr Met Gln Ile Val Gly Asp Leu Ser Tyr Ala Trp Gln Leu
545                 550                 555                 560
Ile Asp Ser Phe Thr Ala Ile Met Gln Glu Ser Ile Arg Ala Asn Pro
                565                 570                 575
Ser Met Val Thr Lys Leu Arg Ala Thr Phe Leu Lys Leu Ala Ser Ala
            580                 585                 590
Leu Asp Leu Pro Leu Leu Arg Ile Asn Gln Ala Asn Ser Pro Asp Leu
        595                 600                 605
Leu Ser Val Ser Gln Tyr Tyr Ser Gly Glu Leu Val Phe Tyr Val Arg
    610                 615                 620
Lys Val Leu Gln Ile Ile Pro Glu Ser Met Phe Thr Ser Leu Ala Lys
625                 630                 635                 640
Ile Ile Lys Leu Gln Thr His Asp Ile Ile Glu Val Pro Thr Arg Leu
                645                 650                 655
Asp Lys Asp Lys Leu Arg Asp Tyr Ala Gln Leu Gly Ala Arg Tyr Glu
            660                 665                 670
Val Ala Lys Leu Thr Asn Ala Ile Ser Ile Phe Thr Glu Gly Ile Leu
        675                 680                 685
Met Met Lys Thr Thr Leu Val Gly Ile Ile Lys Val Asp Pro Lys Gln
    690                 695                 700
Leu Leu Glu Asp Gly Ile Arg Lys Glu Leu Val Lys Arg Val Ala Val
705                 710                 715                 720
Ala Leu His Lys Gly Leu Ile Phe Asn Ser Arg Ala Lys Pro Ser Glu
                725                 730                 735
Leu Leu Pro Lys Leu Lys Asp Met Ala Ala Thr Met Asp Gly Phe His
            740                 745                 750
Arg Ser Phe Glu Tyr Ile Gln Asp Tyr Val Ser Ile Tyr Gly Leu Lys
        755                 760                 765
```

Ile Trp Gln Glu Glu Val Ser Arg Ile Val Asn Tyr Asn Val Glu Gln
770                 775                 780

Glu Cys Asn Asn Phe Leu Arg Thr Lys Ile Gln Asp Trp Gln Ser Met
785                 790                 795                 800

Tyr Gln Ser Thr His Ile Pro Ile Pro Lys Phe Pro Pro Val Asp Glu
            805                 810                 815

Ser Met Thr Phe Ile Gly Arg Leu Cys Arg Glu Ile Leu Arg Ile Thr
            820                 825                 830

Asp Pro Lys Val Thr Cys Tyr Ile Asp Gln Met Asn Thr Trp Tyr Asp
            835                 840                 845

Met Lys Thr His Gln Glu Val Thr Asn Asn His Leu Phe Ser Glu Ile
850                 855                 860

Asn Asp Ser Leu Gly Thr Phe Gly Leu Asn Gly Leu Asp Arg Leu Leu
865                 870                 875                 880

Cys Phe Met Ile Val Lys Glu Leu Gln Asn Phe Ile Arg Leu Tyr Gln
                885                 890                 895

Arg Leu Ile Leu Arg Asp Lys Ser Gly Gln Glu Thr Leu Arg Ala Leu
            900                 905                 910

Gln Lys Val Val Thr Pro Val Lys Gly Ile Val Ala Asn Ser Ala Lys
            915                 920                 925

Ile Tyr Ser Ala Ala Ile Ala Lys Thr Gln Lys Ile Trp Pro Ala Tyr
930                 935                 940

Leu Asp Ala Ile Met Lys Val Gly Gln Met Gln Val Leu Arg Gln Gln
945                 950                 955                 960

Ile Ala Asn Glu Leu Asn Tyr Ser Cys Lys Phe Asp Ser Lys His Leu
                965                 970                 975

Ala Gly Ala Leu Glu Asn Phe Asn Glu Ala Ile Leu Ala Asp Ile Gln
            980                 985                 990

Ala His Tyr Gln Asp Pro Ser Leu Pro Cys Pro Arg Glu Asp Asn Thr
            995                 1000                1005

Leu Leu Tyr Glu Ile Thr Ala Tyr Leu Glu Ala Ala Gly Thr His Asn
    1010                1015                1020

Pro Leu Asn Lys Ile Tyr Ile Thr Thr Lys Gln Leu Ser Phe Phe Pro
1025                1030                1035                1040

Ile Val Asn Phe Leu Phe Leu Val Ala Gln Leu Pro Lys Leu Gln Tyr
            1045                1050                1055

Asn Lys Asn Leu Gly Met Thr Cys Arg Lys Pro Ala Asp Pro Ile Asp
            1060                1065                1070

Trp Val Pro Leu Val Leu Gly Leu Leu Thr Leu Leu Lys Gln Phe His
            1075                1080                1085

Ser Arg Tyr Thr Glu Gln Phe Leu Ala Leu Ile Gly Gln Phe Ile Arg
    1090                1095                1100

Ser Ser Leu Glu Gln Ser Thr Ser Gln Lys Ile Pro Glu Met Pro Ala
1105                1110                1115                1120

Asp Val Val Gly Ala Leu Met Phe Leu Glu Asp Tyr Val His Phe Ala
            1125                1130                1135

Lys Leu Pro Arg Arg Val Val Glu Ala His Val Pro Asn Phe Ile Phe
            1140                1145                1150

Asp Glu Phe Arg Thr Ile Gln
            1155

<210> SEQ ID NO 33
<211> LENGTH: 1191

```
<212> TYPE: PRT
<213> ORGANISM: Drosophila melanogaster

<400> SEQUENCE: 33

Met Ser Phe Leu Asp Asp Asn Asn Ala Cys Gly Gln Asn Leu Leu Asn
 1               5                  10                  15

Ile Val Ser Val Gly Asn Ser Ile Ile Ala Glu Ile Leu Arg Leu Lys
             20                  25                  30

Asp Tyr Val Pro Ser Ile Tyr Arg Leu Asp Asn Lys Ala Asp Lys Ala
         35                  40                  45

Lys Tyr Gly Glu Leu Ile Leu Asp Phe Ser Tyr Phe Lys Ile Ala Glu
 50                  55                  60

Asp His Glu Arg Arg Ile Glu Gln Ser Pro Glu Leu Thr Glu Leu Asp
 65                  70                  75                  80

Asp Glu Ala Arg Ala Gln Leu Pro Leu Ile Thr Arg Phe Tyr Leu Ala
                 85                  90                  95

Phe Gln Ser Ile His His Tyr Ala Ser Asp Leu Gln Gln Tyr Ile Glu
            100                 105                 110

Glu Leu Asn Thr Gly Tyr Tyr Ile Gln Gln Thr Leu Glu Thr Val Leu
        115                 120                 125

Gln Glu Glu Glu Gly Arg Gln Leu Leu Cys Glu Ser Leu Tyr Leu Phe
    130                 135                 140

Gly Val Ile Leu Leu Met Val Asp Phe His Ile Pro Gly Asp Val Arg
145                 150                 155                 160

Glu Arg Leu Leu Ile Ala Tyr Tyr Arg Tyr Ser Gly Gly Asp Ala Thr
                165                 170                 175

Pro Ser Gly Asp Glu Ser Asn Ile His Asp Val Cys Leu Leu Leu Arg
            180                 185                 190

Ser Thr Gly Tyr Val His Pro Ser Ile Ala Ala Lys Val Leu Gly Leu
        195                 200                 205

Gly Gly Lys Gln Ala Gly Ala Arg Ala Ala Ser Leu Val Val Pro Arg
    210                 215                 220

Tyr Pro Glu Ala Tyr Phe Ser Arg Phe Arg Phe Asp Glu Asn Phe Val
225                 230                 235                 240

Asp Leu Val Val Ala Arg Leu Arg Cys Asp Asp Ile Tyr Asn Gln Leu
                245                 250                 255

Asn Leu Tyr Pro His Pro Ala His Arg Ser Thr Ala Leu Ser Thr Gln
            260                 265                 270

Ala Ala Met Leu Tyr Val Cys Leu Tyr Phe Cys Pro Gln Val Leu His
        275                 280                 285

Ser Gln Gly Ser Gln Met Arg Glu Ile Val Asp Lys Phe Phe Cys Asp
    290                 295                 300

Asn Trp Thr Ile Ser Val Tyr Met Gly Met Thr Val Asn Leu Val Asp
305                 310                 315                 320

Ala Trp Leu Asp Phe Lys Ala Ala Arg Ser Ala Ile Glu Asn Val Ile
                325                 330                 335

Ser Pro Pro Ala Ile Lys Ala Leu Cys Gln Gln Lys Glu Gln Leu
            340                 345                 350

Gly Lys Ile Thr Gln Lys Thr Gln Glu Ile Val Arg Glu Gly Val Leu
        355                 360                 365

Asn Asp Asn Phe Val Leu Glu His Ala Asn Lys Ile Ile His Leu Met
    370                 375                 380

Arg Gln Ser Asn Val Leu Leu Arg Trp Phe Cys Leu His Thr Ser Arg
385                 390                 395                 400
```

```
Glu Val Phe Ile Phe Ala His Thr Ala Thr Leu Thr Gly Gln Val Gln
                405                 410                 415

Lys Cys Val Leu His Glu Leu Gln Phe Asn Arg Asn Thr Leu Tyr Asn
            420                 425                 430

Leu Leu Leu Asn Cys Ser Gln Met Glu Leu Ser Val Arg Glu Phe Leu
        435                 440                 445

Ala Glu Ile Gln Gln Thr Lys Glu Glu Arg Trp Thr Lys Ser Arg Glu
    450                 455                 460

Glu Ala Met Gln Arg Leu Asn Glu Leu Ser Glu Ala Phe Ala Gly Ser
465                 470                 475                 480

Arg Pro Leu Ser Lys Ile Glu Gln Asn Pro Gln Leu Gln Gln Trp Phe
                485                 490                 495

Gly Glu Val Ala Gly Arg Leu Gln Lys Leu Glu Leu Ser Arg Pro Gln
            500                 505                 510

Lys Ser Gly Arg Leu Ile Ile Gln Val Met Gln Ala Leu Asp Asp Val
        515                 520                 525

Gln Glu Tyr His Asn Leu His Ser Asn Met Leu Val Lys Gln Gln Leu
    530                 535                 540

Gln Glu Thr Arg Asp Met Leu Asn Gln Met Ala Gln Leu Ile Asn Leu
545                 550                 555                 560

Lys Glu Asp Ile Glu Ile His Ile Gln Met Ile Thr Asp Phe Ser Tyr
                565                 570                 575

Ala Trp His Leu Leu Gln Phe Asp Phe Thr Pro Pro Met Gln Glu His
            580                 585                 590

Ile Lys Arg Gln Pro Gln Ala Val Ile Gly Ile Arg Ala Val Phe Leu
        595                 600                 605

Lys Leu Ala Ser Thr Leu Glu Val Pro Leu Met Arg Ile Asn Gln Ala
    610                 615                 620

Arg Ser Glu Asp Leu Val Ser Val Ser Asn Tyr Tyr Ser Thr Glu Leu
625                 630                 635                 640

Ala Asn Phe Leu Arg Arg Val Leu Gln Ile Val Pro Glu Thr Met Phe
                645                 650                 655

Ser Ile Leu Ala Lys Ile Ile Tyr Leu Leu Thr Asn Val Ile Lys Glu
            660                 665                 670

Phe Pro Thr Lys Val Glu Lys Glu Arg Leu Lys Asp Tyr Ala Gln Phe
        675                 680                 685

Glu Glu Arg Ala Lys Val Ala Gln Leu Thr Asn Ser Ile Ala Val Phe
    690                 695                 700

Thr Lys Gly Ile Leu Met Met Lys Thr Thr Leu Val Gly Val Ile Glu
705                 710                 715                 720

Leu Asp Pro Lys Gln Leu Leu Glu Asp Gly Ile Arg Lys Glu Leu Val
                725                 730                 735

Asn His Leu Ala Asn Ala Tyr Asn Leu Gly Leu Ile Phe Thr Pro Glu
            740                 745                 750

Lys Gly Lys Thr Pro Val Gln Leu Leu Gln Lys Leu Gln Ala Leu
        755                 760                 765

Ala Lys Thr Ile Glu Gly Tyr Arg Arg Ser Phe Glu Tyr Ile Glu Asp
    770                 775                 780

Tyr Leu Arg Val Gln Gly Leu Arg Ile Leu Leu Glu Ser Gln Arg
785                 790                 795                 800

Ile Ile Asn Tyr Asn Val Glu Lys Glu Cys Asn Ala Phe Leu Arg Asn
                805                 810                 815
```

Lys Val Gln Glu Phe Gln Ser Glu His Gln Ser Gln Ile Ile Pro Ile
            820                 825                 830

Pro Asn Phe Pro Pro Leu Leu Gly Asp Pro Ser Asn Asn Phe Ile Gly
            835                 840                 845

Arg Leu Ala His Glu Ile Leu Arg Cys Thr Asp Pro Lys Gln Thr Ile
            850                 855                 860

Phe Leu Asp Leu Lys Ser Thr Trp Tyr Glu Lys Ala Pro His Gln
865                 870                 875                 880

Glu Val Leu Ala Gly Ser Gly Phe Phe Glu Ile Leu Arg Glu Ala Leu
            885                 890                 895

Ala Pro Ala Gly Met Val Gly Leu Glu Arg Leu Tyr Ala His Met Leu
            900                 905                 910

Ala Asp Glu Leu Lys Arg Asn Leu Glu Arg Leu Gln Arg Asn Leu Thr
            915                 920                 925

Ser Asp Arg Met Trp Val Asp Thr Leu Ala Ala Leu Thr Arg Glu Leu
            930                 935                 940

Glu Ala Arg Asp Phe Pro Thr Pro Glu Val Ser Lys Gln Pro Leu Lys
945                 950                 955                 960

Tyr Tyr Gln Ala Tyr Thr Gln Arg Trp Leu Lys Val Trp Pro Thr Leu
            965                 970                 975

Leu Asp Trp Val Leu Cys Ile Gly Gln Lys Gln Leu Leu Arg Arg Glu
            980                 985                 990

Ile Ala Gly Glu Leu Ser Phe Ser Ser Lys Cys Asp Ala Lys Leu Leu
            995                 1000                1005

Glu Asn Thr Ala Asp Thr Leu Asn Lys Ala Leu Leu Leu Glu Leu Ser
            1010                1015                1020

Leu Ser Lys Asp Leu Cys Asp Glu Lys Gly Val Val Met Leu Thr Glu
1025                1030                1035                1040

Leu Gln Glu Thr Leu Leu Tyr Thr Gly Asn Phe Glu Pro Leu Glu Gln
            1045                1050                1055

Val Phe Leu Ile Thr Lys Asn Thr His Asn Met Ala Leu Phe Met Phe
            1060                1065                1070

Leu Phe Thr Ile Ala His Leu Gly Arg Met Gln His Ser Thr Ile Thr
            1075                1080                1085

Asp Cys Leu Leu Pro Lys Ser Ala Lys Asp Asn Ile Asp Asn Val Pro
            1090                1095                1100

Phe Ile Val Gly Leu Val Thr Ile Leu Gln Gln Phe His Lys Asn Val
1105                1110                1115                1120

Lys Met Leu Tyr Ile Ser Tyr Met Ser Gln Tyr Val Val Thr Val Ser
            1125                1130                1135

Glu Ala Gln Leu Leu Asp Lys Glu Ile Leu Gly Pro Glu Val Val Thr
            1140                1145                1150

Ala Leu His Phe Leu Leu Ala Phe Ile Arg Ile Ala Arg Leu Pro Leu
            1155                1160                1165

Gly Val Leu Glu Gln Arg Ile Pro Asn Ile Ile Leu Ser Glu Tyr Glu
            1170                1175                1180

Tyr Leu Ser Thr Leu Leu Lys
1185                1190

<210> SEQ ID NO 34
<211> LENGTH: 1159
<212> TYPE: PRT
<213> ORGANISM: Danio rerio

<400> SEQUENCE: 34

```
Met Val Asp Phe Leu Ala Glu Asn Asn Leu Cys Gly Gln Ala Ile Leu
 1               5                   10                  15

Arg Ile Val Ser Arg Gly Asn Ala Ile Ala Glu Leu Leu Arg Leu
            20                  25              30

Ser Asp Phe Ile Pro Ala Val Phe Arg Leu Arg Asp Lys Thr Asp Gln
            35                  40                  45

Gln Lys Tyr Gly Asp Ile Ile Cys Asp Phe Ser Tyr Phe Lys Gly Pro
     50                  55                  60

Glu Tyr Tyr Glu Gly Lys Leu Glu Ala Lys Pro Glu Leu Gln Asp Leu
 65              70                  75                  80

Asp Glu Glu Phe Arg Glu Asn Asn Ile Glu Ile Leu Thr Arg Phe Tyr
                85                  90                  95

Leu Ala Phe Glu Ser Val His Lys Tyr Val Val Asp Leu Ile Arg Cys
                100                 105                 110

Leu Asp Asp Leu Asn Glu Gly Val Tyr Ile Gln Gln Thr Leu Glu Thr
            115                 120                 125

Val Leu Leu Asn Glu Asp Gly Lys Gln Leu Leu Cys Glu Ala Leu Tyr
        130                 135                 140

Leu Tyr Gly Val Met Leu Leu Val Ile Asp Gln Lys Met Glu Gly Glu
145                 150                 155                 160

Val Arg Glu Arg Met Leu Val Ser Tyr Arg Tyr Ser Ala Ala Arg
                165                 170                 175

Ser Ser Ala Asp Ser Asn Leu Asp Asp Ile Cys Lys Leu Leu Arg Ser
            180                 185                 190

Thr Gly Tyr Ser Ser His Pro Gly Ala Lys Arg Pro Thr Asn Tyr Pro
        195                 200                 205

Glu Ser Tyr Phe Gln Arg Val Pro Ile Ser Ser Thr Phe Ile Ser Met
210                 215                 220

Val Ile Gly Arg Leu Arg Ser Asp Asp Ile Tyr Asn Gln Val Ser Ala
225                 230                 235                 240

Tyr Pro Leu Pro Glu His Arg Ser Thr Ala Leu Ala Thr Gln Ala Ala
                245                 250                 255

Met Leu Tyr Val Cys Leu Tyr Phe Thr Pro Ser Ile Leu His Thr Gln
            260                 265                 270

Gln Ala Lys Met Arg Glu Ile Val Asp Lys Tyr Phe Pro Asp Asn Trp
        275                 280                 285

Val Ile Ser Ile Tyr Met Gly Ile Thr Val Asn Leu Val Glu Ala Trp
        290                 295                 300

Glu Pro Tyr Lys Ala Ala Lys Ile Ala Leu Asn Tyr Thr Leu Asp Thr
305                 310                 315                 320

Ala Asn Ile Arg Glu Gln Ala Gly Arg Tyr Ala Ala Ser Val Glu Thr
                325                 330                 335

Leu Arg Pro Gln Val Gln Gln Leu Leu Lys Glu Gly Phe Leu Arg Glu
        340                 345                 350

Glu Ile Ile Leu Asp Asn Ile Pro Lys Leu Leu Asn Cys Leu Arg Asp
            355                 360                 365

Cys Asn Val Ala Ile Arg Trp Leu Met Leu His Thr Ala Glu Ser Ala
    370                 375                 380

Tyr Asp Pro Asn Asn Lys Arg Leu Arg Gln Ile Lys Asp Gln Val Ile
385                 390                 395                 400

Asn Asp Ser Lys Tyr Asn Pro Lys Ile Leu Phe Gln Leu Leu Leu Asp
                405                 410                 415
```

```
Thr Ala Gln Phe Glu Phe Ile Leu Lys Glu Met Phe Lys Gln Met Leu
                420                 425                 430
Ala Glu Lys Gln Leu Lys Trp Glu Ser Tyr Lys Lys Glu Gly Ser Glu
            435                 440                 445
Arg Met Met Glu Leu Ala Glu Val Phe Ser Gly Val Lys Pro Leu Thr
        450                 455                 460
Arg Val Glu Lys Asn Glu Asn Leu Gln Ala Trp Phe Arg Glu Ile Ser
465                 470                  475                 480
Lys Gln Ile Glu Ser Leu Asn Tyr Glu Asp Ser Thr Ala Ala Gly Arg
                485                 490                 495
Lys Thr Val Gln Leu Ile Gln Ala Leu Val Glu Val Gln Glu Phe His
            500                 505                 510
Gln Leu Glu Ser Asn Leu Gln Val Cys Gln Phe Leu Ala Asp Thr Arg
        515                 520                 525
Lys Phe Leu His Gln Met Ile Arg Thr Ile Asn Ile Lys Glu Glu Val
        530                 535                 540
Leu Ile Thr Met Gln Ile Val Gly Asp Leu Ser Tyr Ala Trp Gln Ile
545                 550                 555                 560
Ile Asp Ser Phe Thr Ala Ile Met Gln Glu Ser Ile Arg Ala Asn Pro
                565                 570                 575
Ser Met Val Thr Lys Leu Arg Ala Thr Leu Leu Lys Leu Ala Ser Ala
            580                 585                 590
Leu Asp Leu Pro Leu Leu Arg Ile Asn Gln Val Asn Ser Pro Asp Leu
        595                 600                 605
Leu Ser Val Ser Gln Phe Tyr Ser Gly Glu Leu Val Ala Tyr Val Arg
        610                 615                 620
Lys Val Leu Gln Ile Ile Pro Glu Ser Met Phe Thr Ser Leu Ala Lys
625                 630                 635                 640
Ile Ile Lys Leu Gln Ile His Asp Ile Met Glu Val Pro Thr Arg Leu
                645                 650                 655
Asp Lys Asp Lys Leu Lys Asp Tyr Ser Gln Leu Ser Ala Arg Tyr Glu
            660                 665                 670
Val Ala Lys Leu Thr His Ala Ile Ser Val Phe Thr Glu Gly Ile Leu
        675                 680                 685
Met Met Lys Thr Thr Leu Val Gly Ile Ile Gln Val Asp Pro Lys Gln
        690                 695                 700
Leu Leu Glu Asp Gly Ile Arg Lys Glu Leu Val Lys Arg Val Ala Tyr
705                 710                 715                 720
Ala Leu His Lys Gly Leu Ile Phe Asn Pro Lys Ala Lys Pro Ser Glu
                725                 730                 735
Leu Met Pro Lys Leu Lys Glu Met Ala Ala Thr Met Asp Gly Phe Tyr
            740                 745                 750
Arg Ser Phe Glu Tyr Ile Gln Asp Tyr Val Ser Ile Tyr Gly Leu Lys
        755                 760                 765
Ile Trp Gln Glu Glu Val Ser Arg Ile Ile Asn Tyr Asn Val Glu Gln
770                 775                 780
Glu Cys Asn Ser Phe Leu Arg Thr Lys Ile Gln Asp Trp Gln Ser Val
785                 790                 795                 800
His Gln Ser Thr His Ile Pro Ile Pro Lys Tyr Pro Ser Val Asp Glu
                805                 810                 815
Ser Ala Thr Phe Ile Gly Arg Leu Cys Arg Glu Ile Leu Arg Ile Thr
            820                 825                 830
Asp Pro Lys Val Thr Cys Tyr Ile Asp Gln Leu Asn Thr Trp Tyr Asp
```

```
                    835                 840                 845
Leu Arg Thr His Gln Glu Val Thr Asn Asn Arg Leu Phe Ser Glu Ile
850                 855                 860

Gln Asp Thr Leu Gly Thr Phe Gly Leu Asn Gly Leu Asp Arg Leu Leu
865                 870                 875                 880

Cys Phe Met Ile Val Lys Glu Leu Gln Asn Phe Leu Thr Val Leu Gln
                885                 890                 895

Lys Ser Ile Leu Lys Asp Lys Ala Val Val Asp Val Phe Lys Ala Leu
            900                 905                 910

Leu Thr Ala Val Asn Pro Val Lys Gly Ile Val Ala Asn Ala Ser Lys
        915                 920                 925

Val Tyr Thr Asn Ala Ala Ala Lys Thr Gln Lys Ile Trp Ser Pro Tyr
    930                 935                 940

Leu Glu Ser Ile Met Lys Val Gly Gln Met Gln Ile Leu Arg Gln Gln
945                 950                 955                 960

Ile Ala Asn Glu Leu Asn Tyr Ser Cys Lys Phe Asp Ser Lys His Leu
                965                 970                 975

Ala Ala Ala Leu Asp Asn Leu Asn Lys Ser Leu Leu Ser Asp Ile Glu
            980                 985                 990

Ala His Tyr Gln Asp Pro Ser Leu Pro Tyr Pro Lys Glu Asp Asn Thr
        995                 1000                1005

Leu Leu Tyr Glu Ile Thr Ala Tyr Leu Glu Ala Ala Gly Ile His Asn
    1010                1015                1020

Pro Leu Asn Lys Ile Tyr Ile Thr Thr Lys Arg Leu Pro Tyr Phe Pro
1025                1030                1035                1040

Ile Val Asn Phe Leu Phe Leu Ile Ala Gln Leu Pro Lys Leu Gln Tyr
                1045                1050                1055

Asn Lys Ser Gln Gly Met Ala Cys Arg Lys Pro Ala Asp Ala Leu Asp
            1060                1065                1070

Trp Ala Pro Leu Val Leu Gly Leu Leu Thr Leu Leu Lys Gln Phe His
        1075                1080                1085

Ser Arg Tyr Thr Glu Gln Phe Leu Ala Leu Ile Gly Gln Phe Ile Arg
    1090                1095                1100

Ser Ile Met Glu Gln Cys Thr Ser Gln Lys Ile Pro Asp Met Pro Ser
1105                1110                1115                1120

Asp Val Val Gly Ala Leu Met Phe Leu Glu Asp Tyr Val Arg Tyr Thr
                1125                1130                1135

Lys Leu Pro Arg Lys Val Ala Glu Ala His Val Pro Ser Phe Ile Phe
            1140                1145                1150

Asp Glu Phe Arg Thr Val Leu
        1155

<210> SEQ ID NO 35
<211> LENGTH: 997
<212> TYPE: PRT
<213> ORGANISM: Caenorhabditis elegans

<400> SEQUENCE: 35

Met Thr Glu Glu Ile Asn Ile Phe Leu Ser Lys Leu Ile Leu His Gly
1               5                   10                  15

Glu Ser Ile Leu Ala Glu Ile Phe Arg Leu Ser Ser Phe Ile Pro Lys
            20                  25                  30

Asp Phe Arg Asp Pro Thr Lys Ser Ser Lys Phe Lys Asn Ile Val Gln
        35                  40                  45
```

Leu Asp Phe Lys Tyr Leu Ser Lys Val Asp Gln Ile Glu Lys Glu Leu
            50                  55                  60

Glu Ser His Leu Arg Leu Gln Thr Gln Phe Tyr Ser Thr Phe Glu Pro
 65                  70                  75                  80

Val Leu Ile Ala Phe Glu Gln Leu Phe Ser Ser Ile Ser Glu Phe Val
                 85                  90                  95

Gln Ser Phe Ile Ser Tyr Thr Lys Glu Ala Glu Ile Ile Asn Gly Glu
                100                 105                 110

Thr Arg Met Asp Val Asn Arg Thr Ser Glu Leu Glu Ala Tyr Cys Leu
            115                 120                 125

Tyr Ile Ser Gly Ile Leu Ile Ile Tyr Met Asp Thr Tyr Ile Pro Ala
130                 135                 140

Pro Ile Arg Glu Arg Ile Tyr Ile Ala Ile Tyr Arg Lys Ser Asp Val
145                 150                 155                 160

Arg Glu Asn Ala Glu Phe Leu Val Asp Phe Leu Lys Ala Thr Val Pro
                165                 170                 175

Gly Asn Asp Ser Met Ile Arg Arg Ile Pro Leu Pro Glu Ser Phe Ile
            180                 185                 190

Thr Ser Thr Ile Asn Ala Ile Glu Ile Ile Glu Gly Thr Ser Leu Gln
            195                 200                 205

Ile Pro Lys Ala Gln Leu Met Tyr Val Ala Leu Gln Phe Asp Arg Gln
210                 215                 220

Thr Leu Thr Asn Asp Ser Ala Ile Met Thr Lys Ile Ala Asn Ser Ile
225                 230                 235                 240

Tyr Arg Glu Thr Trp Val Ile Asn Leu Gly Phe Gly Val Ile Ala Asn
                245                 250                 255

Val Phe Asp Gly Trp Tyr Asn Phe Lys Ser Ala Trp Asn Ala Ile Asn
            260                 265                 270

Ser Thr Ile Thr Gln Asp Ala Gln Arg Ile Met Glu Lys His Leu
            275                 280                 285

Lys Met Met Asn Glu Thr Ser Phe Pro Gln Val Ile Asn Glu Met Ile
290                 295                 300

Asp Phe Glu Gln Asn Leu Lys Lys Ile Ser Met Cys Asn Arg Ser Leu
305                 310                 315                 320

Lys Trp Leu Phe Leu His Ser Lys Ile Ser Gln Lys Thr Ser Arg Pro
                325                 330                 335

Leu Asn Lys Tyr Arg Leu Pro Ser Asp Gln Leu Phe Gln Trp Leu
            340                 345                 350

Leu His Val Ser Arg Cys Glu Ile Leu Leu Asn Leu Tyr Thr Thr
            355                 360                 365

Thr Leu Glu Asn Arg Asp Val Glu Gly Thr Glu Arg Lys Gln Asn Ile
370                 375                 380

Arg Thr Leu Leu His Gln Leu Ala Glu Phe Phe Glu His Gly Phe Val
385                 390                 395                 400

Lys Met Gly Glu Ser Gln Lys Thr Asn Phe Val Lys Trp Val Arg Asn
                405                 410                 415

Leu Ser Glu Thr Val Glu Lys Ile Asp Leu Asn Asp Thr Thr Glu Ser
            420                 425                 430

Val Glu Thr Ile Gln Gln Ile Arg Arg Val Lys Gln Val Gly Asp
            435                 440                 445

Gln Leu Gly Leu Ser Ile Asn Leu Thr Leu Lys Asp Cys Leu Ser Thr
450                 455                 460

Leu Asp Thr Asp Leu Arg Ala Leu Met Ser Val Leu Ser Leu Ser Asp

-continued

```
                465                 470                 475                 480
            Ser Met Ile Pro Glu Val Tyr Ser Lys Met Glu Ser Thr Tyr Leu Trp
                            485                 490                 495

Pro Leu Ile Ser Gln Leu Ile Pro Arg Ile Gln Gln Asn Leu Val Ser
                        500                 505                 510

Thr Ser Asn Thr Asp Val Val Arg Gln Ile Phe Thr Lys Leu Ser Ile
                    515                 520                 525

Ser Cys Tyr Met Leu Lys Leu Lys Leu Ser Asn Phe Ser Asp Lys Asp
                530                 535                 540

His Val Ala Ser Arg Ile Ala Asn Thr Tyr Ser Tyr Ala Leu Glu Lys
            545                 550                 555                 560

Asn Leu Lys Thr Val Leu Gln Ser Val Pro Gln His Leu Phe Gly Ile
                            565                 570                 575

Met Tyr Asn Val Ile Met Pro Gly Leu Gly Lys Thr Phe Glu Pro Tyr
                        580                 585                 590

Ile Glu Lys Thr Glu Leu Arg Glu Leu Ser Glu Phe Val Thr Asn Ser
                    595                 600                 605

Arg Leu Val Glu Thr Thr Ser Leu Ile Ala Asn Thr Ser Met Gly Ile
                610                 615                 620

Ser Arg Met Met Leu Thr Arg Val Gly Thr Ile Glu Ile Asn Pro Lys
            625                 630                 635                 640

Glu Leu Leu Glu Glu Gly Met Ile Arg Gln Leu Tyr Lys Glu Ile Lys
                            645                 650                 655

Lys Met Ile Gly Thr Thr Ser Ala Thr Ser Ser Ile Glu Asn Leu Leu
                        660                 665                 670

Lys Met Cys Asp Asn Ile Glu Thr Met Arg Cys Ser Phe Leu Tyr Leu
                    675                 680                 685

Cys Asp Tyr Met Asn Leu Asp Gly Glu His Val Trp Ser Val Ala Met
                690                 695                 700

Asp Asp Phe Phe Ser Arg Ile Ser Glu Glu Arg Ala Phe Ala Arg Ser
            705                 710                 715                 720

Ser Gly Glu Leu Glu Lys Asn Tyr Ile Ala Glu Leu Phe Ile Lys Ile
                            725                 730                 735

Thr Asn Pro Lys Ala Ser Arg Phe Ser Glu Ser Ser Leu Ser Trp Lys
                        740                 745                 750

Asp Val Lys Met Ser Lys Thr Val Leu Ser Phe Asp Val Phe Asp Arg
                    755                 760                 765

Ile Glu Lys Ile Val Pro Phe His Ile Leu Thr Ser Ile Glu Thr His
                770                 775                 780

Ile Thr Val Glu Leu Glu Lys Met Leu Ile Glu Tyr Ile Ser Asn Ala
            785                 790                 795                 800

Arg Lys Ile Gly Val Ser Phe Asn Leu Gln Asn Ser Val Thr His Glu
                            805                 810                 815

Ser Ala Phe Gln Phe Phe Thr Gly Pro Asn Tyr Glu Arg Leu Val Lys
                        820                 825                 830

Ser Ile Gln Pro Gln Ser Ala Ala Leu Ala Ala Ile Leu Ala Gln Ile
                    835                 840                 845

Gly Gln Tyr Leu Ile Ile Leu Arg Thr Ile Cys Asn Ala Lys Gln Leu
                850                 855                 860

Ala Asn Arg His Lys Glu Asp Ser Ile Gln Arg Asp Leu Ile Glu Met
            865                 870                 875                 880

Ser Ile Ser Met Ala Arg Asp Pro Thr Asp Leu Pro Thr Glu Met Gly
                            885                 890                 895
```

Thr Ile Leu Lys Leu Met Met Gln Tyr Ser Leu Tyr Asp Pro Glu Arg
                900                 905                 910

Met Ile Phe Arg Leu Lys Asp Glu Pro Ser Pro Leu Phe Ile Ile Ala
            915                 920                 925

Leu Val Gln Cys Leu Leu Pro Lys Ile Gly Asp Pro Tyr Phe Val Cys
        930                 935                 940

Pro Lys Gln Leu Glu Val Gly Ile Arg Phe Val Leu Arg Gln Ser Arg
945                 950                 955                 960

Leu Leu Pro Tyr Phe Leu Pro Ile Ile Arg Glu Gln Leu Pro Gln Ser
                965                 970                 975

Ser Arg Pro Lys Lys Arg Val Ser Asp Val Asp Arg Phe Leu Arg His
            980                 985                 990

Leu Ile Ser Asn Leu
        995

<210> SEQ ID NO 36
<211> LENGTH: 1164
<212> TYPE: PRT
<213> ORGANISM: Dictyostelium discoideum

<400> SEQUENCE: 36

Met Val Lys Glu Phe Leu Gly Glu Gly Ser Gln Ala Gly Gln Asn Leu
1               5                   10                  15

Leu Arg Leu Val Ser Arg Gly Asn Ala Ile Ile Ala Glu Leu Leu Arg
            20                  25                  30

Leu Ser Ala His Ile Pro Ser Val Phe Lys Leu Glu Asp Arg Asn Glu
        35                  40                  45

Ala Arg Lys Tyr Gln Asp Ile Leu Leu Asp Phe Lys Tyr Leu Ser Asn
    50                  55                  60

Pro Asp Phe Tyr Glu Ser Lys Ile Glu Glu Asn Ala Asp Leu Val Asp
65                  70                  75                  80

Leu Glu Thr Glu Phe Arg Asp Asn His Ile Asp Ile Leu Ile Arg Phe
                85                  90                  95

Tyr His Leu Phe Glu Ser Ile Tyr Lys Tyr Ile Met Asp Leu Glu His
            100                 105                 110

Tyr Ile Val Asp Val Glu Lys Gly Phe Tyr Ile His Leu Thr Ile Glu
        115                 120                 125

Ala Ile Leu Ile Asn Gly Asp Gly Lys Gln Leu Leu Ser Glu Ala Val
    130                 135                 140

Tyr Leu Tyr Gly Val Met Leu Ile Leu Met Asp Asn Leu Ile Glu Gly
145                 150                 155                 160

Pro Val Arg Glu Arg Met Leu Ile Ser Tyr Leu Arg Asn Lys Gly Pro
                165                 170                 175

Val Asp Leu Pro Leu Ile Asp Glu Val Cys Lys Leu Cys Lys Ser Thr
            180                 185                 190

Gly Tyr Ile Pro Gly Ser Pro Lys Lys Pro Asn Tyr Pro Glu Glu
        195                 200                 205

Tyr Phe Arg Arg Val Glu Leu Pro Glu Asn Val Ile Ser Met Ile Val
    210                 215                 220

Gly Arg Leu Arg Ser Asp Asp Leu Tyr Asn Gly Thr Glu Ser Phe Pro
225                 230                 235                 240

Gln Pro Glu His Arg Ser Val Ala Leu Ser Thr Gln Ala Cys Met Ile
                245                 250                 255

Tyr Val Ile Leu Tyr Phe Ile Pro Asp Ile Leu Asn Asn Lys Asn Ser

```
                260             265             270
Ile Met Arg Glu Ile Val Asp Lys Phe Phe Pro Asp Asn Trp Val Ile
            275             280             285
Ser Phe Phe Leu Gly Phe Thr Ile Asp Leu Ser Val Ala Trp Glu Pro
290             295             300
Tyr Lys Ala Ala Lys Thr Ala Met Gly Asn Thr Ile Ile Gln Ser Asn
305             310             315             320
Ile Gln Tyr Gln Thr Gln Arg Phe Trp Lys Glu Val Ser Glu Leu Asn
            325             330             335
Lys Leu Val Asp Asp Leu Leu Val Asp Gly Leu Leu Val Glu Glu Tyr
            340             345             350
Ile Val Asp Asn Val His Lys Ile Ile Thr Thr Leu Arg Arg Cys Asn
            355             360             365
Val Thr Ile Arg Trp Val Met Leu His Ser Asn Ala Ser Gln Lys Lys
            370             375             380
Phe Lys Asp Leu Val Leu Met Gly Gly Ser Gln Glu Asp Val Leu Tyr
385             390             395             400
Leu Leu Leu Asn Thr Ala Gln Leu Glu Phe Val Phe Lys Asn Ile Phe
                405             410             415
Gln Gln Leu Leu Ala Thr Lys Glu Glu Lys Trp Glu Glu Asn Lys Lys
            420             425             430
Leu Ala Ser Asp Ser Met Val Glu Leu Ser Glu Tyr Phe Ser Gly Glu
            435             440             445
Lys Ala Leu Thr Arg Val Lys Lys Asn Glu Asn Leu Gln Lys Trp Phe
            450             455             460
Gly Glu Ile Ser Gln Lys Ile Ser Gln Leu Asp Ser Thr Asp Ser Thr
465             470             475             480
Ser Thr Gly Arg Lys Ile Gln Gln Leu Ser Leu Ala Leu Glu Glu Val
            485             490             495
Glu Gln Phe Gln Gln Ile Asp Ser Ser Ile Gln Val Lys Gln Phe Leu
            500             505             510
Ile Glu Thr Arg Gln Phe Leu Thr Lys Met Ile Lys Ile Val Asn Ile
            515             520             525
Lys Glu Glu Val Leu Val Asn Leu Ser Val Cys Ala Asp Met Ser Tyr
            530             535             540
Ala Trp Glu Ile Val Asn Asn Tyr Val Asp Gln Met Gln Lys Gly Ile
545             550             555             560
Lys Ser Asp Pro Lys Cys Val Leu Lys Leu Arg Ala Thr Phe Leu Lys
            565             570             575
Leu Val Ser Ile Leu Asp Leu Pro Leu Val Arg Ile Ala Gln Cys Ser
            580             585             590
Ser Pro Asp Leu Ile Ser Val Ser Glu Tyr Tyr Ser Gly Glu Leu Val
            595             600             605
Gly Tyr Val Arg Lys Val Leu Glu Ile Val Pro Lys Gln Met Phe Leu
            610             615             620
Ile Leu Lys Gln Ile Ile Asn Met Gln Thr Asn Asn Ile Gln Glu Met
625             630             635             640
Pro Thr Lys Val Glu Lys Glu Arg Leu Arg Asp Phe Ala Gln Leu Asp
            645             650             655
Gln Arg Tyr Asp Leu Ala Arg Ala Thr His Ser Val Ser Val Phe Thr
            660             665             670
Glu Gly Ile Leu Ala Met Glu Thr Thr Leu Val Gly Ile Ile Glu Val
            675             680             685
```

```
Asp Pro Lys Gln Leu Leu Glu Asp Gly Ile Arg Lys Glu Leu Val Leu
            690                 695                 700

Gln Ile Ala Leu Ala Met Asp Lys Thr Leu Ile Phe Ser Gly Lys Pro
705                 710                 715                 720

Tyr Gln Ala Pro Ser Asn Lys Gln Gln Gln Glu Ile Glu Leu Leu
                725                 730                 735

Gln Arg Leu Lys Glu Leu Ser Asn Ile Leu Asp Gly Phe Arg Arg Ser
            740                 745                 750

Phe Gln Tyr Ile Gln Asp Tyr Val Asn Ile Gln Gly Leu Lys Ile Trp
                755                 760                 765

Gln Glu Glu Phe Ser Arg Ile Val Asn Phe Tyr Val Glu Gln Glu Cys
770                 775                 780

Asn Ser Phe Leu Lys Lys Lys Val Tyr Asp Trp Gln Ser Gln Tyr Gln
785                 790                 795                 800

Ser Val Ala Ile Pro Ile Pro Lys Phe Pro Ser Gln Ser Asp Gln Asn
                805                 810                 815

Ser Gln Gln Ser Val Asn Met Ile Gly Arg Leu Ala Arg Glu Leu Leu
            820                 825                 830

Asn Gln Thr Asn Cys Lys Thr Thr Leu Tyr Leu Asn Gln Ile Gly Trp
            835                 840                 845

Phe Asp Pro Ser Ser Gly Lys Glu Leu Val Gly Ile Asn Thr Trp Ser
850                 855                 860

Ile Leu His Gln Ser Val Gly Ile Phe Gly Leu Thr Gly Leu Asp Lys
865                 870                 875                 880

Leu Phe Ser Phe Met Met Val Lys Asp Leu Gln Val Phe Val Ser Gln
                885                 890                 895

Thr Arg Ser Leu Val Glu Lys Ser Leu Lys Gly Phe Leu Asn Glu Phe
            900                 905                 910

Glu Asp Tyr Leu Arg Pro Thr Thr Asn Ile Pro Asp Thr Met Ile Arg
                915                 920                 925

Tyr Gln Gln Ala Leu Asp Lys Thr Lys Leu Leu Tyr Pro Ile Phe Ile
            930                 935                 940

Asp Val Leu Thr Lys Ile Gly Gln Ile Gln Leu Ile Arg Arg Gln Ile
945                 950                 955                 960

Ser Asn Gln Leu Asn Phe His Cys Lys Ile Asp Ser Asn Met Leu Phe
                965                 970                 975

Ser Ser Leu Asp Ile Met Asn Lys Ser Leu Leu Asn Asp Ile Glu Ser
            980                 985                 990

His Phe Gln Arg Pro Asp Ser Asn Pro Tyr Pro Ser Asp Asp Asn Thr
            995                 1000                1005

Leu Leu Phe Asp Leu Ala Gln Tyr Leu Asp Thr Ala Gly Ile Asn Asp
    1010                1015                1020

Pro Phe Thr Lys Ile Tyr Ile Thr Thr Ser Pro Leu Glu Gln Phe Pro
1025                1030                1035                1040

Cys Leu Leu Phe Leu Phe Val Leu Ser Gln Val Ser Lys Phe Gln Phe
                1045                1050                1055

Asn Ser Lys Leu Asn Val Met Ser Ser Lys Lys Gln Lys Asn Ser Tyr
            1060                1065                1070

Asp Trp Thr Pro Phe Ile Ile Gly Cys Ile Thr Ile Leu Gln Gln Phe
            1075                1080                1085

His Ser Leu His Thr Gln Lys Phe Leu Ala Phe Val Gly Gln Tyr Ile
    1090                1095                1100
```

```
Lys Ser His Ile Asn Ile Ala Leu Ala Asn Pro Lys Glu Asn Asn Lys
1105                1110                1115                1120

Asp Asp Ala Asp Tyr Pro Glu Asp Val Ile Gly Leu Arg Phe Leu
            1125                1130                1135

Glu Asp Phe Cys Lys Tyr Ser His Thr Ser Arg Lys Ile Val Glu Gly
            1140                1145                1150

Tyr Val Pro Pro Tyr Ile Phe Asp Tyr Tyr Asn Asn
        1155                1160

<210> SEQ ID NO 37
<211> LENGTH: 18
<212> TYPE: PRT
<213> ORGANISM: Homo sapiens

<400> SEQUENCE: 37

Val Pro Thr Arg Leu Asp Lys Asp Lys Leu Arg Asp Tyr Ala Gln Leu
 1               5                  10                  15

Gly Pro

<210> SEQ ID NO 38
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 38
gccaagagtg ttaatctagc aaagtc                                          26

<210> SEQ ID NO 39
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 39
ttcatggttc ccagagaaaa cacg                                            24

<210> SEQ ID NO 40
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 40
tctgctttaa gtttgggatg tcta                                            24

<210> SEQ ID NO 41
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 41
ttaagatgac cagtgccaca ggta                                            24

<210> SEQ ID NO 42
<211> LENGTH: 24
<212> TYPE: DNA
<213> ORGANISM: Artificial Sequence
<220> FEATURE:
```

<223> OTHER INFORMATION: Primer for mutation screening of KIAA0196

<400> SEQUENCE: 42
aatatcaaac tgtggccta aatc                                         24

<210> SEQ ID NO 43
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 43
tacaccgagg aggctcataa cttc                                        24

<210> SEQ ID NO 44
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 44
catcccagcc atctgtcctg atac                                        24

<210> SEQ ID NO 45
<211> LENGTH: 25
<212> TYPE: DNA
<213> ORGANISM: Artifical
<220> FEATURE:
<223> OTHER INFORMATION: Primer for mutation screening of KIAA0196

<400> SEQUENCE: 45
acatacactg cattttaccg acagc                                       25

<210> SEQ ID NO 46
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 46
aatggaattc tactttattg gact                                        24

<210> SEQ ID NO 47
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 47
ctcaaaaggt tttaaaaggt tctacc                                      26

<210> SEQ ID NO 48
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 48
tgggctttgg aaaaactgat gtgtct                                      26

```
<210> SEQ ID NO 49
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 49
aagtttacct aagtgatgtt atgtcc                                          26

<210> SEQ ID NO 50
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 50
caaaaagcaa cgttaatagg tgtaa                                           25

<210> SEQ ID NO 51
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 51
atcattgcat taaattatct aagtg                                           25

<210> SEQ ID NO 52
<211> LENGTH: 27
<212> TYPE: DNA
<213> ORGANISM: Artificial Sequence
<220> FEATURE:
<223> OTHER INFORMATION: Primer for mutation screening of KIAA0196

<400> SEQUENCE: 52
ttaatcacag ccagaactag gatgtag                                         27

<210> SEQ ID NO 53
<211> LENGTH: 27
<212> TYPE: DNA
<213> ORGANISM: Artificial Sequence
<220> FEATURE:
<223> OTHER INFORMATION: Primer for mutation screening of KIAA0196

<400> SEQUENCE: 53
gacaggggag agcttttcag gtatgct                                         27

<210> SEQ ID NO 54
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 54
tggcactcca tgtcagattc aactgt                                          26

<210> SEQ ID NO 55
<211> LENGTH: 21
<212> TYPE: DNA
<213> ORGANISM: Artificial Sequence
<220> FEATURE:
<223> OTHER INFORMATION: Primer for mutation screening of KIAA0196
```

<400> SEQUENCE: 55
atgtctatat tccccattag g                                          21

<210> SEQ ID NO 56
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 56
cagggtcaat gttaatttat agtgta                                     26

<210> SEQ ID NO 57
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 57
agatggaggc caactgtgac tctc                                       24

<210> SEQ ID NO 58
<211> LENGTH: 20
<212> TYPE: DNA
<213> ORGANISM: Artificial Sequence
<220> FEATURE:
<223> OTHER INFORMATION: Primer for mutation screening of KIAA0196

<400> SEQUENCE: 58
tgctccaggc atttttgtcg                                            20

<210> SEQ ID NO 59
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 59
gaacagactg ctgggtgggt cata                                       24

<210> SEQ ID NO 60
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 60
atgagcacca tagagtccat tcagg                                      25

<210> SEQ ID NO 61
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 61
attatgctct cgtggaaaaa ctgcta                                     26

<210> SEQ ID NO 62
<211> LENGTH: 27

```
<212> TYPE: DNA
<213> ORGANISM: Artificial Sequence
<220> FEATURE:
<223> OTHER INFORMATION: Primer for mutation screening of KIAA0196

<400> SEQUENCE: 62 cttttgaaa caagaaacag atatacc                                          27

<210> SEQ ID NO 63
<211> LENGTH: 27
<212> TYPE: DNA
<213> ORGANISM: Artificial Sequence
<220> FEATURE:
<223> OTHER INFORMATION: Primer for mutation screening of KIAA0196

<400> SEQUENCE: 63
ggcaagtaaa aacatctgta catccac                                         27

<210> SEQ ID NO 64
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 64
tttgcagcat ttttagaagg attagc                                          26

<210> SEQ ID NO 65
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 65 ttccctgag aatactgagg cgaaca                                           26

<210> SEQ ID NO 66
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 66
ggaggccagg gaagggagg ttacc                                            25

<210> SEQ ID NO 67
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 67
ggaatgtcaa acagccagat gatgt                                           25

<210> SEQ ID NO 68
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 68
```
actttgctga aataaacaga gtcc                                        24

<210> SEQ ID NO 69
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 69
gtaaggtctt gttcgcgata ggtt                                        24

<210> SEQ ID NO 70
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 70
agaacgaata gttgacaatc tactc                                       25

<210> SEQ ID NO 71
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 71
tgaggtttgg gatgtgtact ctaa                                        24

<210> SEQ ID NO 72
<211> LENGTH: 27
<212> TYPE: DNA
<213> ORGANISM: Artificial Sequence
<220> FEATURE:
<223> OTHER INFORMATION: Primer for mutation screening of KIAA0196

<400> SEQUENCE: 72
aattatatgg aaaagggata actaggt                                     27

<210> SEQ ID NO 73
<211> LENGTH: 27
<212> TYPE: DNA
<213> ORGANISM: Artificial Sequence
<220> FEATURE:
<223> OTHER INFORMATION: Primer for mutation screening of KIAA0196

<400> SEQUENCE: 73
taaagggtca gaatatgagt tgacaag                                     27

<210> SEQ ID NO 74
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 74
ttggtgccgc atgtcctgtt gagtc                                       25

<210> SEQ ID NO 75
<211> LENGTH: 25
<212> TYPE: DNA
<213> ORGANISM: Artificial Sequence

```
<220> FEATURE:
<223> OTHER INFORMATION: Primer for mutation screening of KIAA0196

<400> SEQUENCE: 75
aagtcttatc ttcccaagtt gaaac                                           25

<210> SEQ ID NO 76
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 76
cccagcctct gttctgcata gcat                                            24

<210> SEQ ID NO 77
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 77
aagaacagat ccagaaacgg agat                                            24

<210> SEQ ID NO 78
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 78
aaggcccagt gaagaattgt catc                                            24

<210> SEQ ID NO 79
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 79
ctgaagaaac tggggtgcgt agat                                            24

<210> SEQ ID NO 80
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 80
ctgaggcttg aaaagattac atcac                                           25

<210> SEQ ID NO 81
<211> LENGTH: 25
<212> TYPE: DNA
<213> ORGANISM: Artificial Sequence
<220> FEATURE:
<223> OTHER INFORMATION: Primer for mutation screening of KIAA0196

<400> SEQUENCE: 81
cttccccttt gtcatgagct ttcac                                           25
```

<210> SEQ ID NO 82
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 82
tcccacactc ccctatatt cacctc                                          26

<210> SEQ ID NO 83
<211> LENGTH: 26
<212> TYPE: DNA
<213> ORGANISM: Artificial Sequence
<220> FEATURE:
<223> OTHER INFORMATION: Primer for mutation screening of KIAA0196

<400> SEQUENCE: 83
agaaaagatc tcatatccga catagg                                         26

<210> SEQ ID NO 84
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 84
gacccctgga atgccctacc aatc                                           24

<210> SEQ ID NO 85
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 85
ctggcagggt gactaaggat ggac                                           24

<210> SEQ ID NO 86
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 86
gatagatagc agggatcgtg ttgt                                           24

<210> SEQ ID NO 87
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 87
aggcatctac tgtgaacgac ctat                                           24

<210> SEQ ID NO 88
<211> LENGTH: 23
<212> TYPE: DNA
<213> ORGANISM: Artificial Sequence
<220> FEATURE:
<223> OTHER INFORMATION: Primer for mutation screening of KIAA0196

<400> SEQUENCE: 88 aaagggctg tttcaaggag tcg                    23

<210> SEQ ID NO 89
<211> LENGTH: 24
<212> TYPE: DNA
<213> ORGANISM: Artificial Sequence
<220> FEATURE:
<223> OTHER INFORMATION: Primer for mutation screening of KIAA0196

<400> SEQUENCE: 89 agttttgaa tcataagcga gacg                    24

<210> SEQ ID NO 90
<211> LENGTH: 19
<212> TYPE: DNA
<213> ORGANISM: Artificial Sequence
<220> FEATURE:
<223> OTHER INFORMATION: ASO primer for exon 11

<400> SEQUENCE: 90
actagaaaac cttcaagct                    19

<210> SEQ ID NO 91
<211> LENGTH: 19
<212> TYPE: DNA
<213> ORGANISM: Artificial Sequence
<220> FEATURE:
<223> OTHER INFORMATION: ASO primer for exon 11

<400> SEQUENCE: 91
actagaagac cttcaagct                    19

<210> SEQ ID NO 92
<211> LENGTH: 14
<212> TYPE: DNA
<213> ORGANISM: Artificial Sequence
<220> FEATURE:
<223> OTHER INFORMATION: ASO primer for exon 14

<400> SEQUENCE: 92
ggagagttgg tatc                    14

<210> SEQ ID NO 93
<211> LENGTH: 14
<212> TYPE: DNA
<213> ORGANISM: Artificial Sequence
<220> FEATURE:
<223> OTHER INFORMATION: ASO primer for exon 14

<400> SEQUENCE: 93
ggagagttcg tatc                    14

<210> SEQ ID NO 94
<211> LENGTH: 14
<212> TYPE: DNA
<213> ORGANISM: Artificial Sequence
<220> FEATURE:
<223> OTHER INFORMATION: ASO primer for exon 15

<400> SEQUENCE: 94
cactgaaggt tttg                    14

<210> SEQ ID NO 95

```
<211> LENGTH: 14
<212> TYPE: DNA
<213> ORGANISM: Artificial Sequence
<220> FEATURE:
<223> OTHER INFORMATION: ASO primer for exon 15

<400> SEQUENCE: 95
cactgaagtt tttg                                                        14

<210> SEQ ID NO 96
<211> LENGTH: 23
<212> TYPE: DNA
<213> ORGANISM: Artificial Sequence
<220> FEATURE:
<223> OTHER INFORMATION: Primer for site-directed mutagenesis of exon 14

<400> SEQUENCE: 96
ctggagagtt cgtatcctat gtg                                              23

<210> SEQ ID NO 97
<211> LENGTH: 26
<212> TYPE: DNA
<213> ORGANISM: Artificial Sequence
<220> FEATURE:
<223> OTHER INFORMATION: Primer for site-directed mutagenesis of exon 15

<400> SEQUENCE: 97
cctatgtgag aaaattttg cagatc                                            26

<210> SEQ ID NO 98
<211> LENGTH: 24
<212> TYPE: DNA
<213> ORGANISM: Artificial Sequence
<220> FEATURE:
<223> OTHER INFORMATION: Antisense morpholino against the zebrafish
      strumpellin ortholog, BC045490

<400> SEQUENCE: 98
ctctgccaga aaatcaccat gatg                                             24

<210> SEQ ID NO 99
<211> LENGTH: 24
<212> TYPE: DNA
<213> ORGANISM: Artificial Sequence
<220> FEATURE:
<223> OTHER INFORMATION: Antisense morpholino mismatch control

<400> SEQUENCE: 99
ctctcccaca aaatgagcat catg                                             24

<210> SEQ ID NO 100
<211> LENGTH: 15
<212> TYPE: PRT
<213> ORGANISM: Homo sapiens

<400> SEQUENCE: 100

Lys Gly Pro Glu Leu Trp Glu Ser Lys Leu Asp Ala Lys Pro Glu
 1               5                  10                  15

<210> SEQ ID NO 101
<211> LENGTH: 16
<212> TYPE: PRT
<213> ORGANISM: Homo spaiens

<400> SEQUENCE: 101

Tyr Val Arg Tyr Thr Lys Leu Pro Arg Arg Val Ala Glu Ala His Val
```

<210> SEQ ID NO 102
<211> LENGTH: 20
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 102
ccgggactgc ggatagaaga                                               20

<210> SEQ ID NO 103
<211> LENGTH: 25
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 103
aatcctgtag ctctggctta gcatc                                         25

<210> SEQ ID NO 104
<211> LENGTH: 25
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 104
tctgagttta ttcctgctgt gttca                                         25

<210> SEQ ID NO 105
<211> LENGTH: 25
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 105
ctctcgggat agttggatgg tcttt                                         25

<210> SEQ ID NO 106
<211> LENGTH: 25
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 106
gctgctcgat cttctgctga ttcaa                                         25

<210> SEQ ID NO 107
<211> LENGTH: 25
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 107
atcggatggc aacattgcag tctct                                         25

<210> SEQ ID NO 108
<211> LENGTH: 24
<212> TYPE: DNA
<213> ORGANISM: Artificial Sequence

```
<220> FEATURE:
<223> OTHER INFORMATION: Primer for cDNA analysis of the KIAA0196 gene

<400> SEQUENCE: 108
taagggagga gatggttctg gaca                                          24

<210> SEQ ID NO 109
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 109
tcgagtatcg gcaagaaact gaca                                          24

<210> SEQ ID NO 110
<211> LENGTH: 26
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 110
tgaaacccct aaccagagtg gagaaa                                        26

<210> SEQ ID NO 111
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 111
atcgtgggcc tagctgagca tagt                                          24

<210> SEQ ID NO 112
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 112
agcttcagac ccacgacatt attg                                          24

<210> SEQ ID NO 113
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 113
ccacaggggt aaacttgggt attg                                          24

<210> SEQ ID NO 114
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 114
ttggcaaagc atgtaccagt ccac                                          24
```

```
<210> SEQ ID NO 115
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 115
tctgcatctg cccaaccttc atta                                          24

<210> SEQ ID NO 116
<211> LENGTH: 22
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 116
tccgccattg ccaaaacaca ga                                            22

<210> SEQ ID NO 117
<211> LENGTH: 21
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 117
ggccaatcag cgccaggaac t                                             21

<210> SEQ ID NO 118
<211> LENGTH: 23
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 118
gcttgtcctg ggactgctca ctc                                           23

<210> SEQ ID NO 119
<211> LENGTH: 24
<212> TYPE: DNA
<213> ORGANISM: Artificial Sequence
<220> FEATURE:
<223> OTHER INFORMATION: Primer for cDNA analysis of the KIAA0196 gene

<400> SEQUENCE: 119
agaggcagta caaaaatgtg ttct                                          24
```

METHOD OF PROGNOSING AND DIAGNOSING HEREDITARY SPASTIC PARAPLEGIA, MUTANT NUCLEIC ACID MOLECULES AND POLYPEPTIDES

RELATED APPLICATIONS

This application is a Divisional of U.S. patent application Ser. No. 13/110,640, filed May 18, 2011, which is a Divisional of U.S. patent application Ser. No. 11/983,957, filed Nov. 13, 2007, now U.S. Pat. No. 7,989,167, which claims the benefit of U.S. Provisional Application No. 60/858,354, filed on Nov. 13, 2006. The contents of these applications are incorporated by reference in their entirety.

FIELD OF THE INVENTION

The present invention relates to method of prognosing and diagnosing hereditary spastic paraplegia, mutant nucleic acid molecules and polypeptides.

BACKGROUND OF THE INVENTION

Hereditary Spastic Paraplegia (HSP) has a worldwide prevalence between 1-18 in 100,000[1-3] and is characterized by central motor system deficits leading to lower limb spastic paraperesis.[4-6] This is due to a "dying back" phenomenon whereby upper motor neurons degenerate progressively, commencing with the longest axons.[7,8] HSP can be classified into pure and complicated forms.[6] In pure HSP, lower limb spasticity is the only major presenting symptom. Alternatively, in complicated HSP, this spasticity can be accompanied by other neurological or non-neurological symptoms such as ataxia, dementia, mental retardation, deafness, epilepsy, ichthyosis, retinopathy, ocular neuropathy and extrapyramidal disturbances.[6,9] There is clinical heterogeneity within families, where age of onset and severity can differ markedly; between families that map to the same locus; and certainly between families which map to separate loci. This complicates genotype-phenotype correlations for HSP.

HSP is also extremely genetically heterogeneous. Eleven genes have been identified out of over 30 loci mapped (SPG1-33). This disease can be transmitted in a dominant (13 loci), a recessive (15 loci) or an X-linked manner (4 loci).[9-11] By far the most common locus for the disease is SPG4, with mutations in the microtubule severing protein spastin accounting for ~40 percent of dominant HSP cases (MIM604277).[12,13]

SPG8 is a pure form of hereditary spastic paraplegia with relatively little interfamilial variability in phenotype. SPG8 is considered to be one of the more aggressive subtypes of HSP with disease onset occurring for patients as early as their 20s or 30s. It was first identified in a Caucasian family as a 6.2 cM region between the markers D8S1804 and D8S1774.[14] The family contained 15 patients affected with spasticity, hyperreflexia, extensor plantar reflexes, lower limb weakness, decreased vibration sensation and limited muscle wasting. The candidate region was further reduced to 3.4 cM due to a lower recombinant in a second family, narrowing the interval between markers D8S1804 and D8S1179.[15] This family as well as a third Brazilian family linked to SPG8 also presented with pure adult onset HSP.[16] For two of the families, a muscle biopsy was performed;[14,16] however, no gross histological or histochemical abnormalities were observed. Ragged red fibers have been observed in muscle biopsies of HSP patients with paraplegin mutations.[17] These three families thus present with relatively severe, pure spastic paraplegia.

HSP is one of the most genetically heterogeneous diseases, caused by mutations in at least 31 different genes. This means that >0.1% of genes in the human genome can be mutated resulting in one predominant neurological outcome: the degeneration of upper motor neuron axons. This heterogeneity may in part explain why it was originally difficult to identify the eighth HSP locus, SPG8 leading to an expansion of the candidate interval. The eighth HSP locus, SPG8, is on chromosome 8p24.13. It is possible that two spastic paraplegia genes exist on chromosome 8q23-24, and the overlap of linkage results from both loci yielded a region between the two causative genes. This is similar to the SPG33 gene ZFVE27 which is in close proximity to the SPG9 (MIM 601162) and SPG27 (MIM609041) loci.[25] Alternatively, one originally reported family may have had a false positive linkage result to chromosome 8.

The present description refers to a number of documents, the content of which is herein incorporated by reference in their entirety.

SUMMARY OF THE INVENTION

More specifically, in accordance with the present invention, there is provided a method for diagnosing the presence of hereditary spastic paraplegia (HSP) or predicting the risk of developing HSP in a human subject, comprising detecting the presence or absence of a defect in a gene encoding a polypeptide comprising the sequence of FIG. 9 (SEQ ID NO: 19), in a nucleic acid sample of the subject, whereby the detection of the defect is indicative that the subject has or is at risk of developing HSP.

In a specific embodiment of the method, said sample comprises DNA. In another specific embodiment, said sample comprises RNA. In another specific embodiment, the defect is a missense or spice site mutation.

In another specific embodiment, the defect comprises a mutation in the gene resulting in a mutant polypeptide in which at least one amino acid residue of FIG. 9 (SEQ ID NO: 19) is substituted with another amino acid residue, and wherein the at least one amino acid residue is selected from the group consisting of an asparagine residue at position 471, a leucine residue at position 619 and a valine residue at position 626. In another specific embodiment, the defect comprises a mutation in the gene resulting in a mutant polypeptide in which amino acid residue 471 of FIG. 9 (SEQ ID NO: 19) is substituted with an aspartate residue, or in which amino acid residue 619 of FIG. 9 (SEQ ID NO: 19) is substituted with a phenylalanine residue or in which amino acid residue 626 of FIG. 9 (SEQ ID NO: 19) is substituted with a phenylalanine residue.

In another specific embodiment, the defect comprises a mutation in the gene, wherein the gene is as set forth in FIG. 8 (SEQ ID NO: 18), the mutation being selected from the group consisting of a substitution of a guanine at position 2205 with another nucleotide, a substitution of a guanine at position 2186 with another nucleotide, and a substitution of an adenine at position 1740 with another nucleotide. In another specific embodiment, the defect comprises a mutation in the gene, wherein the gene is as set forth in FIG. 8 (SEQ ID NO: 18), the mutation being selected from the group consisting of a substitution of a guanine at position 2205 with a thymine, a substitution of a guanine at position 2186 with a cytosine, and a substitution of an adenine at position 1740 with a guanine.

In accordance with another aspect of the present invention, there is provided a method comprising the steps of: a) analyzing a nucleic acid test sample containing the gene; b) comparing the results of said analysis of said sample of step a) with the results of an analysis of a control nucleic acid sample containing a wildtype strumpellin gene, wherein the wildtype strumpellin gene encodes a polypeptide comprising the sequence of FIG. 9 (SEQ ID NO: 19); and c) determining the presence or absence of at least one defect in the strumpellin gene of the test sample.

In another specific embodiment of the method, the nucleic acid sample is amplified prior to analysis. In another specific embodiment, the defect is a mutation in the coding region of the strumpellin gene. In another specific embodiment, the mutation is a missense or splice site mutation.

In another specific embodiment, the defect comprises a mutation in the gene resulting in a mutant polypeptide in which at least one amino acid residue of FIG. 9 (SEQ ID NO: 19) is substituted with another amino acid residue, and wherein the at least one amino acid residue is selected from the group consisting of an asparagine residue at position 471, a leucine residue at position 619 and a valine residue at position 626. In another specific embodiment, the defect comprises a mutation in the gene resulting in a mutant polypeptide in which amino acid residue 471 of FIG. 9 (SEQ ID NO: 19) is substituted with an aspartate residue, or in which amino acid residue 619 of FIG. 9 (SEQ ID NO: 19) is substituted with a phenylalanine residue or in which amino acid residue 626 of FIG. 9 (SEQ ID NO: 19) is substituted with a phenylalanine residue. In another specific embodiment, the defect comprises a mutation in the gene, the gene being as set forth in FIG. 8 (SEQ ID NO: 18), the mutation being selected from the group consisting of a substitution of a guanine at position 2205 with another nucleotide, a substitution of a guanine at position 2186 with another nucleotide, and a substitution of an adenine at position 1740 with another nucleotide.

In another specific embodiment, the defect comprises a mutation in the gene, the gene being as set forth in FIG. 8 (SEQ ID NO: 18), the mutation being selected from the group consisting of a substitution of a guanine at position 2205 with a thymine, a substitution of a guanine at position 2186 with a cytosine, and a substitution of an adenine at position 1740 with a guanine.

In another specific embodiment, the analysis is selected from the group consisting of: sequence analysis; fragment polymorphism assays; hybridization assays and computer based data analysis.

In accordance with another aspect of the present invention, there is provided a method of detecting the presence or absence of a mutation in a strumpellin gene, said method comprising the steps of: a) analyzing a nucleic acid test sample containing the gene; b) comparing the results of said analysis of said sample of step a) with the results of an analysis of a control nucleic acid sample containing a wildtype strumpellin gene, wherein the wildtype strumpellin gene comprises the sequence of FIG. 8 (SEQ ID NO: 18); and c) determining the presence or absence of at least one defect in the strumpellin gene of the test sample.

In a specific embodiment, the nucleic acid sample is amplified prior to analysis.

In another specific embodiment, the mutation comprises a mutation in the gene, the mutation being selected from the group consisting of a substitution of a guanine at position 2205 with another nucleotide, a substitution of a guanine at position 2186 with another nucleotide, and a substitution of an adenine at position 1740 with another nucleotide. In another specific embodiment, the mutation comprises a mutation in the gene, the mutation being selected from the group consisting of a substitution of a guanine at position 2205 with a thymine, a substitution of a guanine at position 2186 with a cytosine, and a substitution of an adenine at position 1740 with a guanine.

In accordance with another aspect of the present invention, there is provided a method of selecting a compound, said method comprising: (a) contacting a test compound with at least one biological system displaying a defect in a gene encoding a polypeptide, the polypeptide comprising the sequence of FIG. 9 (SEQ ID NO: 19), wherein the test compound is selected if the polypeptide function, expression or conformation is modified in the presence of the test compound as compared to that in the absence thereof.

In accordance with another aspect of the present invention, there is provided a purified polypeptide comprising a sequence selected from the group consisting of the sequence in FIG. 11 (SEQ ID NO: 21), in FIG. 13 (SEQ ID NO: 23), and in FIG. 15 (SEQ ID NO: 25).

In accordance with another aspect of the present invention, there is provided a purified antibody that binds specifically to the polypeptide of the present invention.

In accordance with another aspect of the present invention, there is provided a method of determining whether a biological sample contains the polypeptide of the present invention, comprising contacting the sample with a purified ligand that specifically binds to the polypeptide, and determining whether the ligand specifically binds to the sample, the binding being an indication that the sample contains the polypeptide.

In a specific embodiment, the ligand is a purified antibody.

In accordance with another aspect of the present invention, there is provided an isolated nucleic acid molecule of no more than 300 nucleotides comprising (a) a sequence of at least 19 contiguous nucleotides of the sequence of FIG. 10 (SEQ ID NO: 20), comprising the nucleotide at position 1740 of FIG. 10; (b) a sequence of at least 19 contiguous nucleotides of the sequence of FIG. 12 (SEQ ID NO: 22), comprising the nucleotide at position 2186 of FIG. 12; (c) a sequence of at least 19 contiguous nucleotides of the sequence of FIG. 14 (SEQ ID NO: 24), comprising the nucleotide at position 2205 of FIG. 14; (d) the complement of the sequence in (a), (b) or (c); or (e) a sequence of at least 19 contiguous nucleotides hybridizable under high stringency conditions to the sequence in (a), (b), (c) or (d).

In accordance with another aspect of the present invention, there is provided a vector comprising the nucleic acid molecule of the present invention. In accordance with another aspect of the present invention, there is provided a recombinant host cell comprising the vector of the present invention.

In accordance with another aspect of the present invention, there is provided an array of nucleic acid molecules attached to a solid support, the array comprising an oligonucleotide hybridizable to one of the nucleic acid molecules of the present invention.

In accordance with another aspect of the present invention, there is provided an isolated nucleic acid molecule comprising the sequence of (a) FIG. 10 (SEQ ID NO: 20); (b) FIG. 12 (SEQ ID NO: 22); (c) FIG. 14 (SEQ ID NO: 24); or (d) the complement of the sequence in (a), (b) or (c). In accordance with another aspect of the present invention, there is provided a vector comprising the nucleic acid molecule of the present invention. In accordance with another aspect of the present invention, there is provided a recombinant host cell comprising the vector of the present invention.

In accordance with another aspect of the present invention, there is provided an isolated nucleic acid molecule encoding a polypeptide comprising the amino acid sequence of (a) FIG. 11 (SEQ ID NO: 21); (b) FIG. 13 (SEQ ID NO: 23); (c) FIG. 15 (SEQ ID NO: 25); or (d) the complement of the sequence in (a), (b) or (c). In accordance with another aspect of the present invention, there is provided a vector comprising the nucleic acid molecule of the present invention. In accordance with another aspect of the present invention, there is provided a recombinant host cell comprising the vector of the present invention.

In specific embodiments of the methods of the present invention, the subject is pre-diagnosed as being a likely candidate for developing HSP.

In accordance with another aspect of the present invention, there is provided a purified polypeptide consisting of a sequence selected from the group consisting of the sequence in FIG. 11 (SEQ ID NO: 21), in FIG. 13 (SEQ ID NO: 23), and in FIG. 15 (SEQ ID NO: 25).

In accordance with another aspect of the present invention, there is provided a method of stratifying a subject having hereditary spastic paraplegia (HSP) comprising: detecting a defect in a strumpellin protein activity and/or in a nucleic acid encoding the protein in a biological sample; whereby the results of the detecting step enables the stratification of the subject having HSP as belonging to a HSP subclass.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

The application file contains at least one drawing executed in color. Copies of this patent or patent application publication with color drawings will be provided by the Office upon request and payment of the necessary fee.

FIG. 8 is the human wildtype KIAA0196 nucleotide sequence (NM 014846.3) (SEQ ID NO: 18);

FIG. 9 is the human wildtype KIAA0196 amino acid sequence (NP_055661) (SEQ ID NO: 19);

FIG. 10 is the mutated human KIAA0196 N471D (c.1740a>g) nucleotide sequence (SEQ ID NO: 20);

FIG. 11 is the mutated human KIAA0196 N471D amino acid sequence (NP_055661) (SEQ ID NO: 21);

FIG. 12 is the mutated human KIAA0196 L619F (c.2186g>c) nucleotide sequence (SEQ ID NO: 22);

FIG. 13 is the mutated human KIAA0196 L619F amino acid sequence (NP_055661) (SEQ ID NO: 23);

FIG. 14 is the mutated human KIAA0196 V626F (c.2205g>t) nucleotide sequence (SEQ ID NO: 24);

FIG. 15 is the mutated human KIAA0196 V626F amino acid sequence (NP_055661) (SEQ ID NO: 25); and FIG. 16 is a multi-species alignment of the human KIAA0196 (strumpellin) amino acid sequence with other species equivalents: *Homo sapiens* (Q12768) (SEQ ID NO: 26), *Canis familiaris* (XP_532327) (SEQ ID NO: 30), Pan troglodytes (XP_519952) (SEQ ID NO: 27), *Drosophila melanogastar* (CG12272) (SEQ ID NO: 33), *Caenorhabditis elegans* (CE13235) (SEQ ID NO: 35), *Xenopus tropicalis* (MGC89323) (SEQ ID NO: 32), *Rattus norvegicus* (XP_343250) (SEQ ID NO: 29); *Danio rerio* (BC045490) (SEQ ID NO: 34), *Gallus gallus* (XP_418441) (SEQ ID NO: 31), *Dictyostelium discoideum* (EAL63144) (SEQ ID NO: 36), and *Mus musculus* (NP_705776.2) (SEQ ID NO: 28). The ruler above the alignment corresponds to the amino acid position of the human KIAA0196 protein (NP_055661).

DETAILED DESCRIPTION OF THE INVENTION

Figure 1:
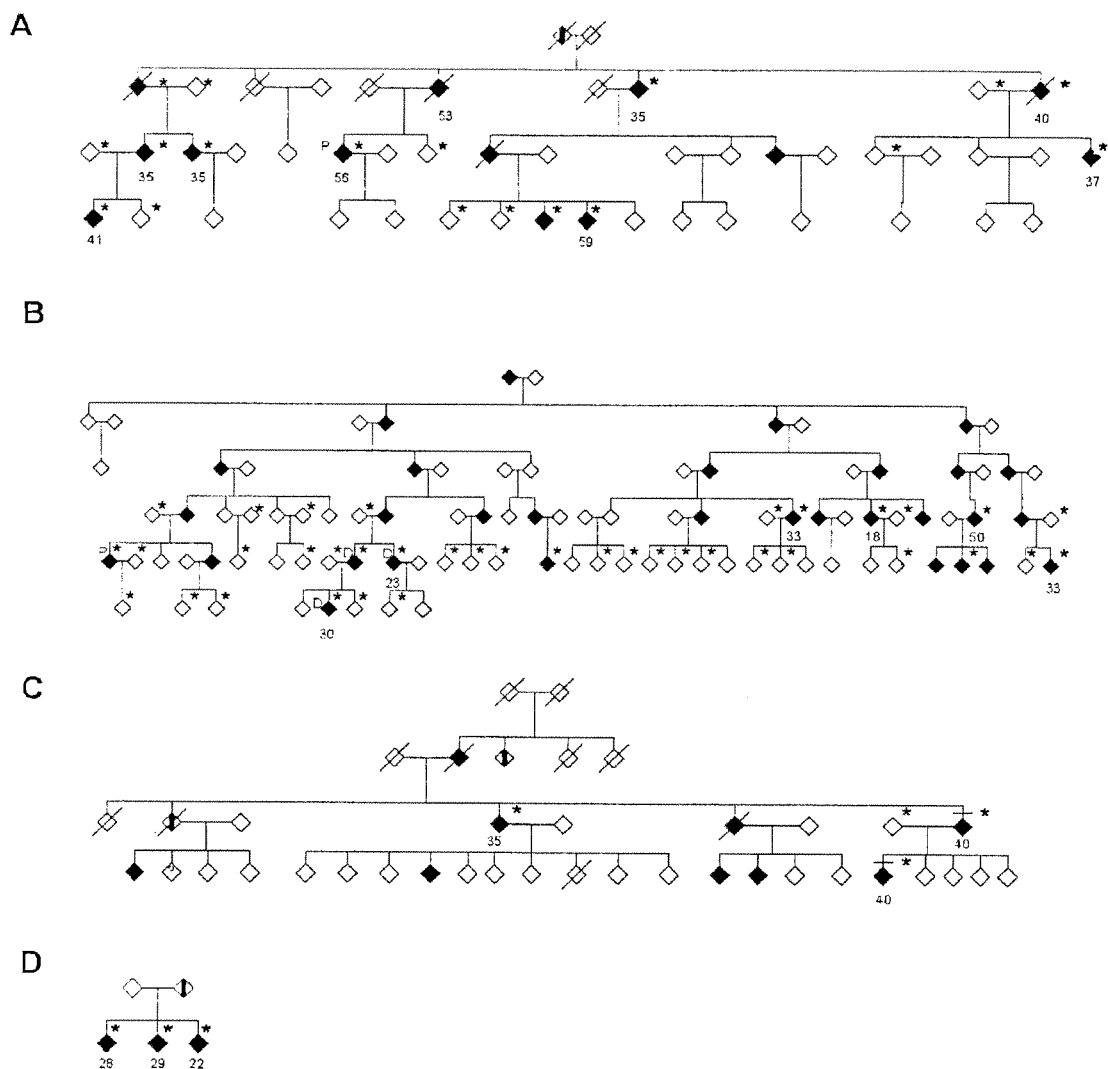
FIG. 1 are pedigrees for families with KIAA0196 mutations. A) Family FSP24, B) Family FSP29, C) Family FSP34, D) Family FSP91. Blackened boxes represent affected individuals, and a diagonal line through the symbol means the individual is deceased. A vertical black bar indicates an individual with an unconfirmed phenotype. Sex of each individual has been masked to preserve confidentiality. Individuals marked "P" represent proximal recombinants and "D" is the distal recombinant. A star indicates that DNA and clinical information have been collected for the particular individual. The age of onset of affected individuals is listed below each symbol, although this information is not available for each patient. All collected affected patients are heterozygous for a c. 2205C->T mutation (pedigrees A, B and C) or a c.A1740G mutation (pedigree D) in KIAA0196 (NCBI accession # NM_014846.3)

Encompassed by the present invention are methods of diagnosing SPG8-associated hereditary spastic paraplegia, or predicting the risk of HSP by detecting mutations associated with the SPG8 locus. The Applicants identified four families linked to the SPG8 locus. Genes were screened in an expanded candidate SPG8 locus defined by these four families along with the British and Brazilian family described previously.[15,16] This led to the identification of three point mutations in the KIAA0196 gene encoding the strumpellin protein product in these six families. One mutation, V626F, segregated in four large North American families with European ancestry. An L619F mutation was found in the Brazilian family. The third mutation, N471D, was identified in a smaller family of European origin, and lies in a spectrin domain. None of these mutations were identified in 500 control individuals. Both the L619 and V626 residues are strictly conserved across species and likely have a notable effect on the structure of the protein product, strumpellin. Rescue studies with human mRNA injected in zebrafish treated with morpholino oligonucleotides to knockdown the endogenous protein showed that mutations at these two residues impaired the normal function of the KIAA0196 gene. Recovery of a normal strumpellin activity nevertheless resulted in recovering normal muscle function. To the Applicant knowledge, there is no other gene than the KIAA0196 gene involved in the SPG8-associated hereditary spastic paraplegia.

Definitions:

As used herein the expressions "risk of developing HSP" or "likely candidate for developing HSP" include subjects suspected of having HSP or subjectsof which a least one parent has HSP.

As used herein the terms "defect", "alteration" or "variation" refers to a mutation or polymorphism in the KIAA0196 gene (also referred to herein as the strumpellin gene) that affects the function, expression (transcription or translation) or conformation of the protein (strumpellin) that it encodes. Mutations encompassed by the present invention can be any mutation the KIAA0196 gene that results in the disruption of the function, expression or conformation of the encoded protein, including the complete absence of expression of the encoded protein and can include, for example, missense and nonsense mutations, insertions and deletions. Without being so limited, mutations encompassed by the present invention may alter splicing the mRNA (splice site mutation) or cause a shift in the reading frame (frameshift). Without being so limited, modifications of the function of strumpellin can be observed with methods such as the zebrafish knockouts experiments presented in Example 6 below.

Also encompassed by the present invention are methods of detecting novel mutations of interest in the strumpellin gene that are associated with HSP. A mutation of interest is any mutation detected in a gene sample obtained from a human subject, having, or suspected of having, HSP. For example, the nucleic acid sequence of a strumpellin gene obtained from a human subject can be compared with the nucleic acid sequence of a wild type (control) strumpellin gene and differences in the nucleotide sequence determined. A difference in the nucleotide sequence of the gene from the human subject is indicative of a mutation associated with HSP. Modifications of a protein encoded by the "different" human gene can be analyzed by various methods, for example, in the zebra fish assay described herein, to evaluate expression or function of the encoded protein. Further, the familial history of HSP, or present symptoms of the human subject can be reviewed, and a determination of the association of the novel mutation with HSP can be made. Thus, additional mutations in the strumpellin gene can be associated with, and diagnostic of, HSP.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

As used herein the term "subject" is meant to refer to any mammal including human, mouse, rat, dog, cat, pig, monkey, horse, etc. In a particular embodiment, it refers to a human.

As used herein the term a suitable "control nucleic acid sample" is meant to refer to a nucleic acid sample (RNA, DNA) that does not come from a subject known to suffer from HSP (control subject). For example, the control can be a wild type strumpellin gene which does not contain a variation in its nucleic acid sequence. Also, as used herein, a suitable control can be a fragment or portion of the wilt type gene that does not include the defect/variation that is the mutation of interest (that is, the mutation to be detected in an assay).

As used herein the terms "subject nucleic acid sample" are meant to refer to any biological sample from the subject from whom nucleic acid sample (RNA, DNA) can be extracted, namely any subject tissue or cell type including saliva and blood.

The present invention also relates to methods for the determination of the level of expression of transcripts or translation product of a single gene such as KIAA0196. The present invention therefore encompasses any known method for such determination including real time PCR and competitive PCR, Northern blots, nuclease protection, plaque hybridization and slot blots. For example, assays commonly used to analyze nucleic acid polymorphisms can include sequencing all, or a portion of, the nucleic acid to detect a variation in the nucleotide sequence. Such assays can include fragment polymorphism analysis, nucleic acid hybridization assays and computerized nucleotide or amino acid sequence comparisons The present invention also concerns isolated nucleic acid molecules including probes. In specific embodiments, the isolated nucleic acid molecules have no more than 300, or no more than 200, or no more than 100, or no more than 90, or no more than 80, or no more than 70, or no more than 60, or no more than 50, or no more than 40 or no more than 30 nucleotides. In specific embodiments, the isolated nucleic acid molecules have at least 20, or at least 30, or at least 40 nucleotides. In other specific embodiments, the isolated nucleic acid molecules have at least 20 and no more than 300 nucleotides. In other specific embodiments, the isolated nucleic acid molecules have at least 20 and no more than 200 nucleotides. In other specific embodiments, the isolated nucleic acid molecules have at least 20 and no more than 100 nucleotides. In other specific embodiments, the isolated nucleic acid molecules have at least 20 and no more than 90 nucleotides. In other specific embodiments, the isolated nucleic acid molecules have at least 20 and no more than 80 nucleotides. In other specific embodiments, the isolated nucleic acid molecules have at least 20 and no more than 70 nucleotides. In other specific embodiments, the isolated nucleic acid molecules have at least 20 and no more than 60 nucleotides. In other specific embodiments, the isolated nucleic acid molecules have at least 20 and no more than 50 nucleotides. In other specific embodiments, the isolated nucleic acid molecules have at least 20 and no more than 40 nucleotides. In other specific embodiments, the isolated nucleic acid molecules have at least 20 and no more than 30 nucleotides. In other specific embodiments, the isolated nucleic acid molecules have at least 30 and no more than 300 nucleotides. In other specific embodiments, the isolated nucleic acid molecules have at least 30 and no more than 200 nucleotides. In other specific embodiments, the isolated nucleic acid molecules have at least 30 and no more than 100 nucleotides. In other specific embodiments, the isolated nucleic acid molecules have at least 30 and no more than 90 nucleotides. In other specific embodiments, the isolated nucleic acid molecules have at least 30 and no more than 80 nucleotides. In other specific embodiments, the isolated nucleic acid molecules have at least 30 and no more than 70 nucleotides. In other specific embodiments, the isolated nucleic acid molecules have at least 30 and no more than 60 nucleotides. In other specific embodiments, the isolated nucleic acid molecules have at least 30 and no more than 50 nucleotides. In other specific embodiments, the isolated nucleic acid molecules have at least 30 and no more than 40 nucleotides.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally known. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. Other detection methods include kits containing probes on a dipstick setup and the like.

As used herein the terms "detectably labeled" refer to a marking of a probe in accordance with the presence invention that will allow the detection of the mutation of the present invention. Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods. Non-limiting examples of labels include 3H, 14C, 32P, and 35S, Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma 32P ATP and polynucleotide kinase, using the Klenow fragment of Pol I of *E. coli* in the presence of radioactive dNTP (e.g. uniformly labeled DNA probe using random oligonucleotide primers in low-melt gels), using the SP6/T7 system to transcribe a DNA segment in the presence of one or more radioactive NTP, and the like.

The present invention also relates to methods of selecting compounds. As used herein the term "compound" is meant to encompass natural, synthetic or semi-synthetic compounds, including without being so limited chemicals, macromolecules, cell or tissue extracts (from plants or animals), nucleic acid molecules, peptides, antibodies and proteins.

The present invention also relates to arrays. As used herein, an "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

As used herein "array of nucleic acid molecules" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

As used herein "solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Any known nucleic acid arrays can be used in accordance with the present invention. For instance, such arrays include those based on short or longer oligonucleotide probes as well as cDNAs or polymerase chain reaction (PCR) products. Other methods include serial analysis of gene expression (SAGE), differential display, as well as subtractive hybridization methods, differential screening (DS), RNA arbitrarily primer (RAP)—PCR, restriction endonucleolytic analysis of differentially expressed sequences (READS), amplified restriction fragment-length polymorphisms (AFLP).

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see 64 for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0. 1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Washing with a solution containing tetramethylammonium chloride (TeMAC) could allow the detection of a single mismatch using oligonucleotide hybridyzation since such mismatch could generate a 10° C. difference in the annealing temperature. The formulation to determine the washing temperature is Tm (° C.)=]−682 ($L^{-1}$)+97 where L represents the length of the oligonucleotide that will be used for the hybridization. In principle, a single mismatch will generate a 10° C. drop in the annealing so that a temperature of 57° C. should only detect mutants harbouring the T mutation.

The present invention relates to a kit for diagnosing HSP and/or predicting whether a subject is at risk of developing HSP comprising an isolated nucleic acid, a protein or a ligand such as an antibody in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the subject sample (DNA genomic nucleic acid, cell sample or blood samples), a container which contains in some kits of the present invention, the probes used in the methods of the present invention, containers which contain enzymes, containers which contain wash reagents, and containers which contain the reagents used to detect the extension products. Kits of the present invention may also contain instructions to use these probes and or antibodies to diagnose HSP or predict whether a subject is at risk of developing HSP.

As used herein the terminology "biological sample" refers to any solid or liquid sample isolated from a subject. In a particular embodiment, it refers to any solid or liquid sample isolated from a human subject. Without being so limited it includes a biopsy material, blood, saliva, synovial fluid, urine, amniotic fluid and cerebrospinal fluid.

As used herein the terminology "biological system" is a cell, a tissue, an organ or an organism. Without being so limited, organisms include a zebrafish.

As used herein the terminology "blood sample" is meant to refer to blood, plasma or serum.

As used herein the term "purified" in the expression "purified polypeptide" means altered "by the hand of man" from its natural state (i.e. if it occurs in nature, it has been changed or removed from its original environment) or it has been synthesized in a non-natural environment (e.g., artificially synthesized). These terms do not require absolute purity (such as a homogeneous preparation) but instead represents an indication that it is relatively more pure than in the natural environment. For example, a protein/peptide naturally present in a living organism is not "purified", but the same protein separated (about 90-95% pure at least) from the coexisting materials of its natural state is "purified" as this term is employed herein.

Similarly, as used herein, the term "purified" in the expression "purified antibody" is simply meant to distinguish man-made antibody from an antibody that may naturally be produced by an animal against its own antigens. Hence, raw serum and hybridoma culture medium containing anti-strumpellin antibody are "purified antibodies" within the meaning of the present invention.

As used herein, the term "ligand" broadly refers to natural, synthetic or semi-synthetic molecules. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The ligand appropriate for the present invention can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "ligand". For example, peptidomimetics, well known in the pharmaceutical industry and generally referred to as peptide analogs can be generated by modeling as mentioned above.

Antibodies

As used herein, the term "anti-strumpellin antibody" or "immunologically specific anti-strumpellin antibody" refers to an antibody that specifically binds to (interacts with) a strumpellin protein and displays no substantial binding to other naturally occurring proteins other than the ones sharing the same antigenic determinants as the strumpellin protein. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ¹⁄₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

This invention will be described herein below, referring to specific embodiments and figures, the purpose of which is to illustrate the invention rather than to limit its scope.

EXAMPLE 1

Material and Methods

Subjects

Protocols were approved by the ethics committee of the Centre hospitalier de l'Université de Montréal (CHUM). Patients gave informed consent after which patient information and blood was collected. DNA was extracted from peripheral blood using standard protocols.

Genotyping and Locus Exclusion

PCR amplified fragments incorporating α-35S-dATP were resolved on 6% denaturing polyacrylamide gels. Alleles were run alongside an M13 mp18 sequence ladder and scored based on allele sizes and frequencies from the Fondation Jean Dausset CEPH database (http://www.ceph-b.fr/). LOD score calculations and multipoint analysis were performed using the MLINK program of the LINKMAP software package.[18]

Mutation Screening

The 28 exons of KIAA0196 were screened by automated sequencing, including at least 50 bp of each intronic region. Primers were designed using the PrimerSelect™ program (Lasergene) and were synthesized by Invitrogen Canada Inc. Primer sequences and amplification conditions for each exon are listed in Table 1 below.

TABLE 1

Primers and conditions for KIAA0196

| | | |
|---|---|---|
| KIAA0196x1F | GCCAAGAGTGTTAATCTAGCAAAGTC | (SEQ ID NO: 38) |
| KIAA0196x1R | TTCATGGTTCCCAGAGAAAACACG | (SEQ ID NO: 39) |
| KIAA0196x2F | TCTGCTTTAAGTTTGGGATGTCTA | (SEQ ID NO: 40) |
| KIAA0196x2R | TTAAGATGACCAGTGCCACAGGTA | (SEQ ID NO: 41) |
| KIAA0196x3F | AATATCAAACTGTGGCCCTAAATC | (SEQ ID NO: 42) |
| KIAA0196x3R | TACACCGAGGAGGCTCATAACTTC | (SEQ ID NO: 43) |
| KIAA0196x4F | CATCCCAGCCATCTGTCCTGATAC | (SEQ ID NO: 44) |
| KIAA0196x4R | ACATACACTGCATTTTACCGACAGC | (SEQ ID NO: 45) |
| KIAA0196x5F | AATGGAATTCTACTTTATTGGACT | (SEQ ID NO: 46) |
| KIAA0196x5R | CTCAAAAGGTTTTAAAAGGTTCTACC | (SEQ ID NO: 47) |
| KIAA0196x6F | TGGGCTTTGGAAAAACTGATGTGTCT | (SEQ ID NO: 48) |
| KIAA0196x6R | AAGTTTACCTAAGTGATGTTATGTCC | (SEQ ID NO: 49) |
| KIAA0196x7F | CAAAAAGCAACGTTAATAGGTGTAA | (SEQ ID NO: 50) |
| KIAA0196x7R | ATCATTGCATTAAATTATCTAAGTG | (SEQ ID NO: 51) |
| KIAA0196x8F | TTAATCACAGCCAGAACTAGGATGTAG | (SEQ ID NO: 52) |
| KIAA0196x8R | GACAGGGGAGAGCTTTTCAGGTATGCT | (SEQ ID NO: 53) |
| KIAA0196x9F | TGGCACTCCATGTCAGATTCAACTGT | (SEQ ID NO: 54) |

TABLE 1-continued

Primers and conditions for KIAA0196

| | | |
|---|---|---|
| KIAA0196x9R | ATGTCTATATTCCCCATTAGG | (SEQ ID NO: 55) |
| KIAA0196x10F | CAGGGTCAATGTTAATTTATAGTGTA | (SEQ ID NO: 56) |
| KIAA0196x10R | AGATGGAGGCCAACTGTGACTCTC | (SEQ ID NO: 57) |
| KIAA0196x11F | TGCTCCAGGCATTTTTGTCG | (SEQ ID NO: 58) |
| KIAA0196x11R | GAACAGACTGCTGGGTGGGTCATA | (SEQ ID NO: 59) |
| KIAA0196x12 and 13F | ATGAGCACCATAGAGTCCATTCAGG | (SEQ ID NO: 60) |
| KIAA0196x12 and 13R | ATTATGCTCTCGTGGAAAAACTGCTA | (SEQ ID NO: 61) |
| KIAA0196x14F | CTTTTTGAAACAAGAAACAGATATACC | (SEQ ID NO: 62) |
| KIAA0196x14R | GGCAAGTAAAAACATCTGTACATCCAC | (SEQ ID NO: 63) |
| KIAA0196x15F | TTTGCAGCATTTTTAGAAGGATTAGC | (SEQ ID NO: 64) |
| KIAA0196x15R | TTCCCCTGAGAATACTGAGGCGAACA | (SEQ ID NO: 65) |
| KIAA0196x16F | GGAGGCCAGGGAAGGGGAGGTTACC | (SEQ ID NO: 66) |
| KIAA0196x16R | GGAATGTCAAACAGCCAGATGATGT | (SEQ ID NO: 67) |
| KIAA0196x17F | ACTTTGCTGAAATAAACAGAGTCC | (SEQ ID NO: 68) |
| KIAA0196x17R | GTAAGGTCTTGTTCGCGATAGGTT | (SEQ ID NO: 69) |
| KIAA0196x18F | AGAACGAATAGTTGACAATCTACTC | (SEQ ID NO: 70) |
| KIAA0196x18R | TGAGGTTTGGGATGTGTACTCTAA | (SEQ ID NO: 71) |
| KIAA0196x19F | AATTATATGGAAAAGGGATAACTAGGT | (SEQ ID NO: 72) |
| KIAA0196x19R | TAAAGGGTCAGAATATGAGTTGACAAG | (SEQ ID NO: 73) |
| KIAA0196x20F | TTGGTGCCGCATGTCCTGTTGAGTC | (SEQ ID NO: 74) |
| KIAA0196x20R | AAGTCTTATCTTCCCAAGTTGAAAC | (SEQ ID NO: 75) |
| KIAA0196x21 and 22F | CCCAGCCTCTGTTCTGCATAGCAT | (SEQ ID NO: 76) |
| KIAA0196x21 and 22R | AAGAACAGATCCAGAAACGGAGAT | (SEQ ID NO: 77) |
| KIAA0196x23F | AAGGCCCAGTGAAGAATTGTCATC | (SEQ ID NO: 78) |
| KIAA0196x23R | CTGAAGAAACTGGGGTGCGTAGAT | (SEQ ID NO: 79) |
| KIAA0196x24F | CTGAGGCTTGAAAAGATTACATCAC | (SEQ ID NO: 80) |
| KIAA0196x24R | CTTCCCCTTTGTCATGAGCTTTCAC | (SEQ ID NO: 81) |
| KIAA0196x25F | TCCCACACTCCCCCTATATTCACCTC | (SEQ ID NO: 82) |
| KIAA0196x25R | AGAAAAGATCTCATATCCGACATAGG | (SEQ ID NO: 83) |
| KIAA0196x26F | GACCCCTGGAATGCCCTACCAATC | (SEQ ID NO: 84) |
| KIAA0196x26R | CTGGCAGGGTGACTAAGGATGGAC | (SEQ ID NO: 85) |
| KIAA0196x27F | GATAGATAGCAGGGATCGTGTTGT | (SEQ ID NO: 86) |
| KIAA0196x27R | AGGCATCTACTGTGAACGACCTAT | (SEQ ID NO: 87) |
| KIAA0196x28F | AAAGGGGCTGTTTCAAGGAGTCG | (SEQ ID NO: 88) |
| KIAA0196x28R | AGTTTTTGAATCATAAGCGAGACG | (SEQ ID NO: 89) |

PCR was performed using 50 ng DNA, 20 pmol of each primer, 10× buffer, 0.25 nM dNTPs and 0.15 ul of Taq (Qiagen). Initial denaturation for 5 minutes at 94° C. was followed by 30 cycles of 30 seconds denaturation at 94° C., 30 seconds annealing at 55° C. (for all exons except for exons 15 and 26), and 45 seconds elongation at 72° C. A final extension at 72° C. was performed for 7 minutes. For exon 15, a 50° C. annealing temperature was used, and for exon 26, 10 cycles of a touchdown reaction were performed from 68° C.-63° C., followed by 25 cycles at 63° C.

Variants were first tested in 12 controls by sequencing, followed by allele-specific oligomerization (ASO).[19,20]

Briefly, 4 μl of PCR product was hybridized onto Hybond-N+™ Nylon membranes (Amersham Biosciences) using a dot blot apparatus. P-32-labelled probes specific to the mutation or normal sequence were hybridized then visualized on autoradiographic film after overnight exposure. ASO primers for exon 11 are 5'-ACTAGAAAACCTTCAAGCT-3' (SEQ ID NO: 90) (normal) and 5'-ACTAGAAGACCT-TCAAGCT-3' (SEQ ID NO: 91) (mutated). For exon 14, ASO primers of 5'-GGAGAGTTGGTATC-3' (SEQ ID NO: 92) (normal) and 5'-GGAGAGTTCGTATC-3' (SEQ ID NO: 93) (mutated) were used. Exon 15 ASO primers were 5'-CACTGAAGGTTTTG-3' (SEQ ID NO: 94) (normal) and 5'-CACTGAAGTTTTG-3' (SEQ ID NO: 95) (mutated).

Protein Sequence Alignment

Cluster analysis was performed using the Probcons™ v. 1.09 program. Proteins from aligned species included *Homo sapiens* (Q12768) (SEQ ID NO: 26), *Canis familiaris* (XP_532327) (SEQ ID NO: 30), *Pan troglodytes* (XP_519952) (SEQ ID NO: 27), *Drosophila melanogastar* (CG12272) (SEQ ID NO: 33), *Caenorhabditis elegans* (CE13235) (SEQ ID NO: 35), *Xenopus tropicalis* (MGC89323) (SEQ ID NO: 32), *Rattus norvegicus* (XP_343250) (SEQ ID NO: 29); *Danio rerio* (BC045490) (SEQ ID NO: 34), *Gallus gallus* (XP_418441) (SEQ ID NO: 31), *Dictyostelium discoideum* (EAL63144) (SEQ ID NO: 36), and *Mus musculus* (NP_705776.2) (SEQ ID NO: 28) (See FIG. 16 for alignment).

Homology Modeling

Figure 5:
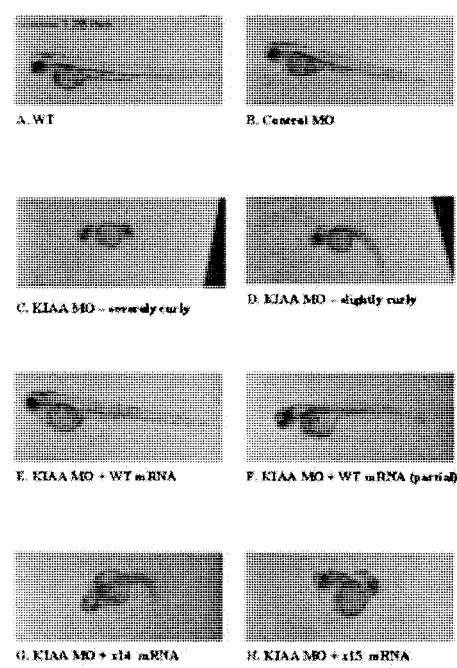
FIG. 5 shows the results of a zebrafish knockdown and rescue of KIAA0196 function. A) The gross morphological features of wildtype zebrafish are depicted at 3 days post fertilization (dpf). B) Injection of a 5 base-pair mismatch morpholino results in no obvious phenotype. C, D) The KIAAMO injected fish present with a severely curly tail (C) or with a slightly curly tail (D). Their heart cavities are also enlarged, which is commonly seen in injected fish. E, F) When the KIAAMO is injected along with normal human KIAA0196 mRNA, the fish partially develop the curly tail (F) or not at all (E) depending on the injected quantity G), H) The phenotype is not alleviated when the KIAAMO is injected with the mutant forms of the human mRNA. These fishes resemble the KIAAMO fish.

The size of the strumpellin protein (1159aa) made it prohibitive to obtain a template for the entire protein. Instead, 200 amino acids around the two mutations were selected (aa 501-725) and inputted in the Phyre™ program version 2.0[39]. The template with the highest score was selected, namely 1dn1b from the Neuronal-Sec1 Syntaxin 1a complex. The SwissProt™ database viewer version 3.721 was used to visualize the model concentrating on the alpha helix in which the two mutations lie and on a second alpha helix nearby in 3D space (See FIG. 5). Peptides incorporating one or the other identified point mutation were visualized in the same manner.

Expression Studies

Northern Blot and RT-PCR Analysis

The KIAA0196 cDNA pBluescript™ clone was kindly provided by the Kazusa DNA Research Institute. A 1 kb probe specific to the c-terminal region of strumpellin was generated by digesting the KIAA0196-pBluescript™ vector with XhoI and NotI. 30 ug of total RNA per sample was loaded. RNA was extracted from various regions of the brain of a control individual. A reverse-transcriptase reaction was performed using MMLV-RT (Invitrogen). Primers in exons 10 (Forward) and 15 (Reverse) of KIAA0196 were used as described in Table 1 above. GAPD cDNA was amplified as a control.

Constructs

Figure 7:
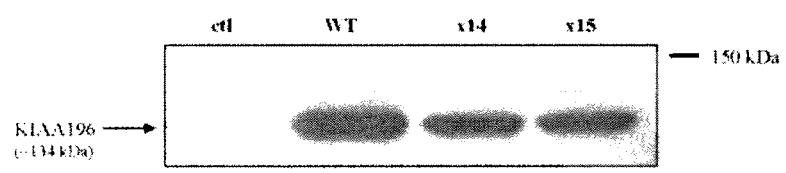
FIG. 7 presents a western blot of the KIAA0196 protein. A) A western blot was prepared using whole cell lysates of HeLa cells transiently expressing the different pCS2-KIAA0196 vectors that incorporate a myc-tag (WT, x14 and x15). The PVDF membrane was immunodetected using an antibody (9E10, Invitrogen) directed against the protein myc-tag portion. The KIAA196 protein migrates to its predicted MW (about 134 kDa). The ctl lane corresponds to the untransfected cells. B) A polyclonal antibody was generated against amino acids 652-669 (VPTRLDKDKL- RDYAQLGP (SEQ ID NO: 37)) of the KIAA0196 protein. This antibody was able to recognize the wildtype and L619F KIAA0196 protein sequence.

Each mutation was introduced into the KIAA0196 pBluescript™ clone by site-directed mutagenesis using the primers 5'-CTGGAGAGTTCGTATCCTATGTG-3' (SEQ ID NO: 96) for the exon 14 variant and 5'-CCTATGT-GAGAAAATTTTTGCAGATC-3' (SEQ ID NO: 97) for the exon 15 variant, along with primers of their complementary sequence. Wildtype and mutant KIAA0196 cDNAs were cloned, upstream of a Myc and His tags, into a pCS2 vector and transcribed in vitro using the SP6 mMESSAGE mMachine™ kit (Ambion) for zebrafish studies. The protein expression from each these constructs was validated following their transient expression in cell culture (HeLa) and subsequent western blot analysis with an anti-Myc antibody. A band at the appropriate height (~134 kDa for KIAA0196) was observed (See FIG. 7).

Zebrafish Knockdown Studies

Morpholino Injections

Wildtype zebrafish were raised and mated as previously described.[22]

Antisense morpholinos (AMO) were designed and purchased from Genetools LLC (Philomath, Oreg.). The morpholino sequences were designed against the zebrafish strumpellin ortholog, BC045490. The oligonucleotide, CTCTGCCAGAAAATCAC[CAT]GATG (SEQ ID NO: 98) (KIAA MO) binds to the ATG of the KIAA0196 gene preventing its translation and CTCTcCCAcAAAATgAg [CAT]cATG (SEQ ID NO: 99) (CTL MO) is a five base pair mismatch control. AMO injections were performed as previously described at a concentration of 0.8 mM.23 The rescue injections were performed as mentioned above with a morpholino and mRNA concentration of 0.8 mM and 50 ng/ul respectively.

Immunohistochemistry

Standard protocols were used for immunohistochemistry.[22] Briefly, three day old embryos were fixed in 4% paraformaldehyde, washed, and blocked at room temperature. Primary antibodies [anti acetylated tubulin, 1:50 (Sigma)] were added overnight. After extensive washing, the embryos were incubated with the fluorescently labelled secondary antibody Alexa 568 (Molecular Probes). Imaging was performed on an UltraView™ LCI confocal microscope (Perkin Elmer) using Methamorph™ Imaging software (Universal Imaging Corporation). The statistical significance between the different conditions was calculated using a chi square test.

Clinical Information and Family Details

The SPG8 family FSP24 is from the province of British Columbia, Canada. It is composed of 13 members affected with a spastic gait and lower limb stiffness, 10 of which have been collected (See FIG. 1a). Symptoms were first observed in individuals between the ages of 35 and 53. Intrafamilial phenotypic heterogeneity exists as noted by the symptoms presented and the range in disease severity in patients. Deep tendon reflexes were brisk or increased, and decreased vibration sensation was also noted in three patients. Occasional bladder control problems were also observed. Walking aids were required for some individuals while one is confined to a wheelchair. Together, these features are consistent with a pure, uncomplicated HSP similar to that described for other families linked to the SPG8 locus. Family FSP29 is of European descent residing in the United States. There are 31 affected individuals in the family, and 10 have been collected (See FIG. 1b). Age of onset was quite variable with symptom onset ranging in patients from their twenties to their sixties. The family was negative for mutations in the spastin gene.

EXAMPLE 2

Linkage Analysis

In FSP24, seven markers spanning the candidate region from markers D8S586 to D8S1128 were genotyped in the 10 affected individuals collected (FIG. 1a). The genotyping and locus exclusion were performed as described in Example 1. A disease haplotype segregated with the disease in all 10 affected individuals (See Table 2 below). A recombination event occurred in one individual (FIG. 1a) between markers D8S586 and D8S1804 defining the proximal border of the locus in this family. No lower recombinant was identified nor searched for since the haplotype extended beyond the limits of the SPG8 locus. The maximum LOD score for this family was 3.43 at θ=0 using CEPH allele frequencies for the marker D8S1804, along with a maximum multipoint of 4.20 at marker D8S1799.

TABLE 2

Haplotype comparison between SPG8 linked families

| Marker | Position (Mb) | FSP24 | FSP29 | FSP34 |
|---|---|---|---|---|
| D8S586 | 121.2 | 1 | 11 | 11 |
| D8S1804 | 124.8 | 5 | 3 | 3 |
| D8S1832 | 125.4 | 2 | 2 | NT |
| D8S1179 | 125.9 | 3 | 9 | 9 |
| KIAA0196 | 126.1 | L619F | L619F | L619F |
| rs2293890 | 126.4 | G | C | C |
| D8S1774 | 127.5 | 3 | 5 | 4 |
| D8S1128 | 128.5 | 7 | 5 | 1 |

Flanking markers in this candidate region are D8S1832 and D8S1774 for family FSP29. NT = not typed The same seven markers tested in FSP24 were genotyped for FSP29. A disease haplotype was established for all 10 collected affected individuals that included many informative recombination events. The proximal recombinant occurred between markers D8S1799 and D8S1832 in three affected individuals (FIG. 1b), and the distal recombinant was between markers D8S1774 and D8S1128 for another affected individual (FIG. 1b). This yielded a candidate interval of 3.15 Mb. The maximum LOD score for this family was 5.62 (θ=0) for the marker D8S1179 when using CEPH allele frequencies. Multipoint analysis was also conducted for this family in this region yielding a maximum LOD score of 6.73, 0.5 cM centromeric to the D8S1128 marker.

EXAMPLE 3

Gene Screening and Mutation Analysis

Figure 2:
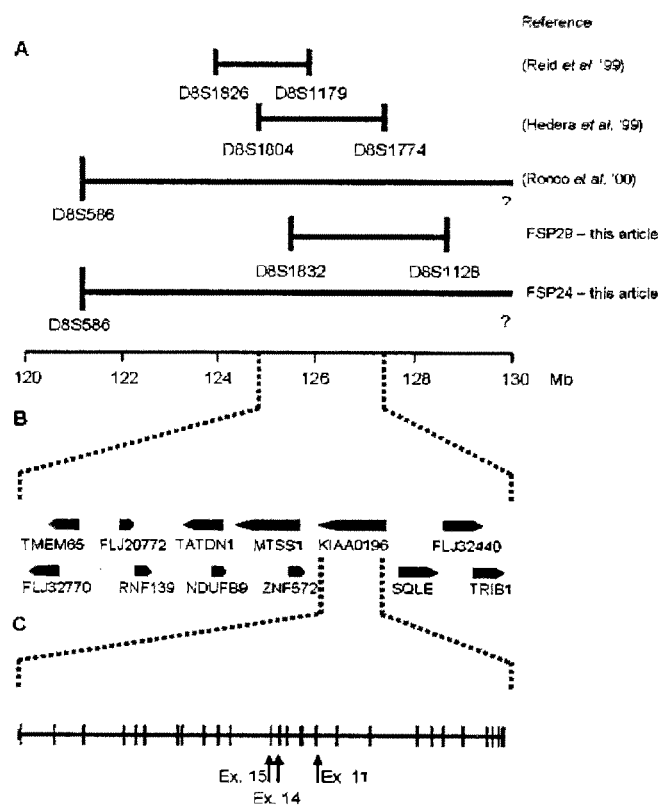
FIG. 2 is a region spanning the SPG8 locus. A) Markers defining the borders of each described SPG8 family and their scaled position on chromosome 8q24.13. B) Candidate region used to search for the SPG8-located gene between markers D8S1804 and D8S1774. Genes in the region are shown in their observed orientation. C) The 28-exon KIAA0196 gene drawn to scale with the location of 3 mutations in exons 11, 14 and 15 highlighted.

The previously published SPG8 locus spanned 3.4 cM (1.04 Mb) between markers D8S1804 and D8S1179 on chromosome 8q23-8q24. Nine known genes were screened surrounding this candidate region as annotated in the UCSC human genome browser (UCSC golden path, http://www.genome.ucsc.edu/[40]) May 2004 update along with many clustered ESTs and mRNAs that aligned to the locus without detecting a mutation. It was Therefore opted to redefine the candidate region based on the critical interval determined by an upper recombinant in the FSP29 family at the marker D8S1832 and a lower recombinant at D8S1774 was based on published data (FIG. 2a).[14] This increased the size of the region to 5.43 cM (3.15 Mb), which contains 3 additional known genes. In total, 12 genes were sequenced between markers D8S1804 and D8S1174 (FIG. 2b). These additional genes were screened and three mutations were identified in the KIAA0196 gene using the mutation screening method describedin Example 1 above (FIG. 2C).

Figure 3A:
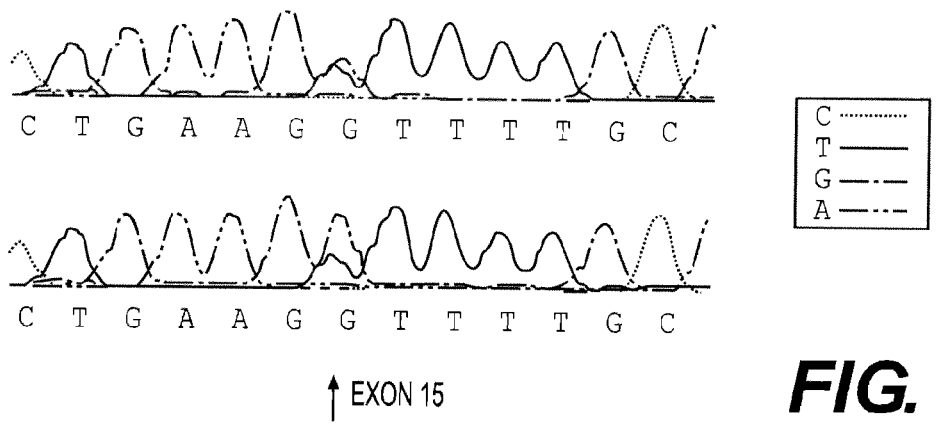
FIG. 3 presents a mutation analysis of the KIAA0196 gene. A-C) Sequence trace of an HSP patient above the sequence trace of a control individual. Exon 15 (A), 14 (B) and 11 (C) heterozygous point mutations are indicated. D) Multiple sequence alignment for strumpellin homologues surrounding the two coding changes (boxed) (human (SEQ ID NO: 7); orangutan (SEQ ID NO: 8); rat (SEQ ID NO: 9); mouse (SEQ ID NO: 10); dog (SEQ ID NO: 11); chicken (SEQ ID NO: 12); zebrafish (SEQ ID NO: 13); fruit fly (SEQ ID NO: 14); C. elegans (SEQ ID NO: 15); frog (SEQ ID NO: 16); and amoeba (SEQ ID NO: 17). The Probcons™ (v.1.09) program[38] was used for cluster analysis. E) RT-PCR of multiple brain regions using a KIAA0196-specific probe. F) Northern blot of the KIAA0196 transcript using 30 ug of total RNA and a 1 kb C-terminal probe.

A valine-to-phenylalanine mutation was identified in amino acid 626 for families FSP24 and FSP29 (p.V626F) (FIG. 3a). All affected individuals collected from each family were screened and were positive for this mutation. This G to T nucleotide change is at position 2205 of the mRNA (see FIG. 14). A total of 500 ethnically matched control individuals (400 from North America, and 100 from CEPH) were negative for this mutation after screening by a combination of allele-specific oligomerization (ASO) and sequencing. No unaffected members and spouse controls in any family were positive for the mutation in exon 15. The family previously described by Reid et al.[15] was also screened for KIAA0196 and the V626F mutation was identified.

Figure 3B:
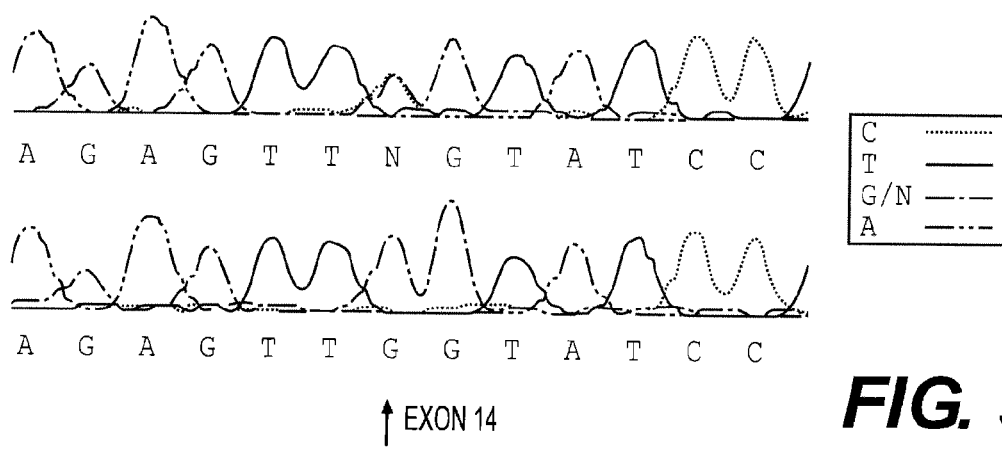

A second mutation was identified in the Brazilian familyl[6] in exon 14, a G to C transition at position 2186 of the mRNA (FIG. 3b). This leucine-to-phenylalanine change (p.L619F) is only 7 amino acids away from the V626F mutation. It was also not found in 500 controls using ASO.

Figure 3C:
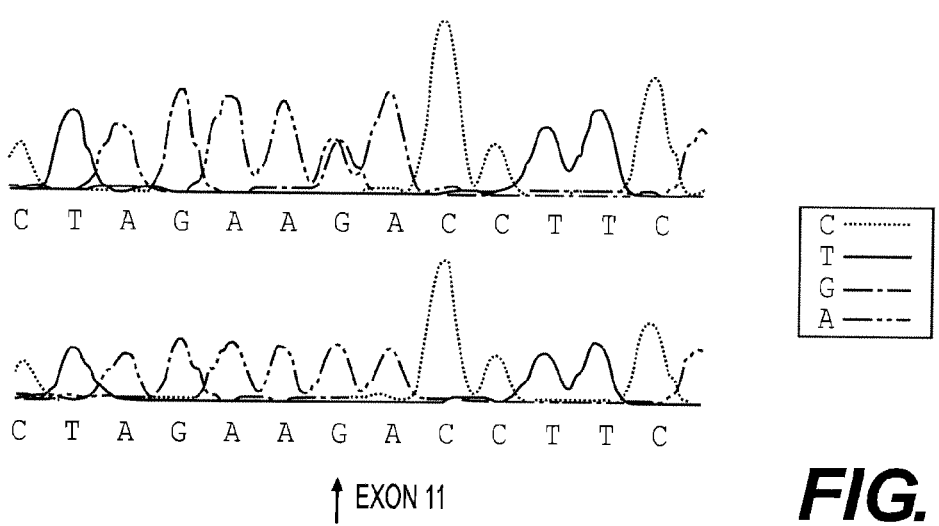

The KIAA0196 gene was screened in probands from 24 additional dominant HSP families that are negative for mutations in both spastin and atlastin, resulting in the identification of two more families with missense mutations in the KIAA0196 gene. Thus, the frequency of mutations in SPG3A and SPG4-negative autosomal dominant cohort is ~8% (2 in 24). FSP34 has the same p.V626F change in its 3 affected collected members. This family is originally from Great Britain, residing in Canada (FIG. 1 c). Haplotype analysis of this family with markers D8S1804, D8S1179, D8S1774 and D8S1128 indicated that there is allele sharing between this family and family FSP29 suggesting an ancestral haplotype (Table 2 above). An additional mutation was found in exon 11 in three affected siblings of another North American family of European origin, FSP91 (FIG. 1d). This c.A1740G transition results in an asparagine to aspartate amino acid change (p.N471D), and is not present in the 500 controls tested (FIG. 3c). The Hedera et al. family[14] was not screened but it is expected that affected members possess a mutation in the KIAA0196 genes.

Protein sequence alignment was performed as described in Example 1 above. Mutated amino acids at positions 619 and 626 are strictly conserved across all eleven species examined all the way to the social amoeba, *Dictyostelium discoideum* (FIG. 3D). Indeed, the entire region surrounding these two mutations appears to be functionally relevant for the protein as 73 consecutive amino acids (aa 576-649) are 100% identical between the human, dog, chicken, mouse, rat and orangutan. Despite this high level of conservation, this region is not a known domain, based on NCBI's conserved domain database search, NCBI's BLAST™ search, and the Sanger Institute's Pfam database.[41] Position 471 is conserved across all species save for *Drosophila melanogastar* with a glutamine residue and *Xenopus tropicalis* with a histidine.

The exon 15 mutation is in the very first nucleotide of the exon, which leads to the speculation that the splicing of this exon might be compromised in these families. Splice site prediction programs including NetGene2™ suggested that the strength of the splice site acceptor may be reduced by 33% in the mutant form.[42] However, both normal and mutant alleles were observed in cDNA analysis of patient lymphoblasts using several pairs of primers. The KIAA0196 gene was expressed ubiquitously, including all regions of the brain which were examined by RT-PCR (FIG. 3e). There were no alternative splice isoforms detected in control brain samples and the patient whole blood samples by RT-PCR and northern analysis (FIGS. 3e and 3f). For the full KIAA0196 gene, all spliced ESTs and mRNAs from the UCSC browser, May 2004 draft, were analyzed for potential alternative splice products. One alternative first exon often appears; however, out of the 356 entries, only two (AK223628 and DA202680) contain exons which are skipped. Thus overall, the gene is not frequently spliced, and the two spliced entries may represent spurious transcripts.

EXAMPLE 4

KIAA0196 Profile

The KIAA0196 gene spans 59.7 kilobase pairs of genomic DNA, is 28 exons long and codes for a protein of 1159 amino acids that is named strumpellin herein. The EBI institute's InterPROScan™ program[43] predicted a spectrin-repeat containing domain from amino acids 434 to 518. Thus, the mutation at position 471 may abrogate the binding of the spectrin domain with other spectrin-repeat containing proteins. In examining the secondary structure using PSIPRED[24], 74% of the protein is considered to be alpha-helical. The program further predicted an α-helix in the protein from amino acids 606 to 644, encompassing the two other mutations which have been identified. The helix consists of a heptameric repeat with hydrophobic residues aligning in inaccessible regions at the center of the helix. The hydrophobic lysine and valine amino acids are seven amino acids apart in the protein sequence; thus it is expected they would be buried in the helix, close in 3D space (FIG. 5a).

Human KIAA0196 gene is known to have previously been implicated in prostate cancer.[32] An increase in gene copy number was assayed by real-time quantitative PCR and fluorescence in-situ hybridization, determining over ten-fold overexpression of the gene in PC-3 prostate cancer lines, and in ~⅓ of advanced prostate cancers examined.32

Analysis of other species has provided some insight into a potential function for KIAA0196. A 118 kDa homologue of the strumpellin protein was identified as part of a TATA-binding protein-related factor 2 (TRF2) complex in a *Drosophila* nuclear extract.[33] Eighteen proteins were pulled down along with TRF2 in this complex including NURF and SWI, with functions for chromatin remodeling and transcription activation. TRF2 is selective for promoters lacking TATA or CAAT boxes. One protein of the complex is DREF which binds to DRE elements common in controlling genes involved in cell cycle regulation and cell proliferation.[34,35]

EXAMPLE 5

Homology Modeling

Figure 4A:
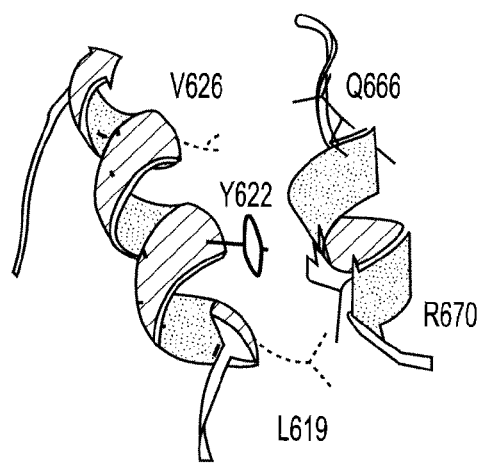
FIG. 4 presents a three-dimensional modelling of strumpellin using d1dn1b as a template using SwissProt™ database viewer. Two helices from the 1159aa protein are shown including amino acids 614-634 in one alpha helix and amino acids 662-672 from a nearby alpha helix in the antiparallel direction. A) Residues L619 and V626 are in the same orientation in an alpha helix opposite a second helix in an antiparallel direction. Only residue side-chains which are closest in physical space are shown. B) The L619F mutation adds a bulky phenylalanine side-group which likely exceeds the space available between the two alpha helices C) The V626F mutation. The epsilon carbon of the F626 aromatic ring also may force apart the two alpha-helices and impinges on Q666.
Figure 4B:
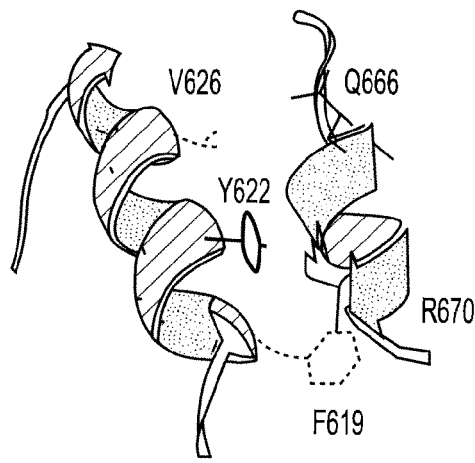
Figure 4C:
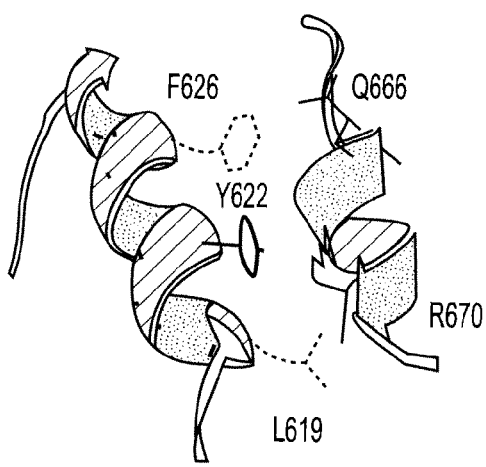

Homology modeling was performed as described in Example 1 above. Given the high proportion of KIAA0196 considered to be alpha-helical, it is not surprising that the optimal homology modeling candidates are similar in secondary structure composition. This is true for 1dn1b, a stat-like t-SNARE protein neuronal-Sec1 Syntaxin 1a complex. This is the most appropriate model for strumpellin according to the Phyre™ program. The two mutated residues lie within an alpha-helix from amino acids 619-628 which is in close 3D proximity to another alpha-helix from residues 665-670 (FIG. 4a). A mutation in either Val-626 or Leu-619 to a phenylalanine residue would appear to have significant structural implications given the change in bulkiness between each of the residues. In addition, Tyr-622 points in the same direction from the alpha-helix residue. To have two amino acids with aromatic rings in such a physical proximity could force apart the alignment of the two alpha-helices or induce alterations in the alpha-helix backbone The one known domain in strumpellin is a spectrin repeat which consists of three α-helices of a characteristic length wrapped in a left-handed coiled coil.[26] These spectrin repeats appear in the spectrin/dystrophin/α-actinin family. The spectrin proteins have multiple copies (15-20) of this repeat which can then form multimers in the cell. Spectrin also associates with the cell membrane via spectrin repeats in the ankyrin protein. Likewise, four spectrin repeats are found in α-actinin beside two N-terminal calponin homology domains which anchor the complex to actin.[27] This effectively connects the cell membrane with the actin cytoskeletal network. The stability and structure of this network also provides appropriate routes for intracellular vesicular transport, a mechanism already linked to other mutated HSP genes. Proteins with three spectrin repeats or fewer can be considered to have transient association with the spectrin network. The single repeat in strumpellin is more likely to be involved in docking with one of the cytoskeletal spectrin repeats, which could help in protein localization or signal transduction.

Proteins with a spectrin repeat have been identified in other neurological disorders, most notably dystrophin, mutated in myotonic dystrophy (MIM300377).28 The repeat also has been found in a form of cerebellar ataxia (MIM117210).[29] β-III spectrin itself is found to be mutated in SCA5.[30] While none of the genes mutated in HSP have a spectrin domain, L1CAM (SPG1) has an indirect association.[9,31] L1CAM is a single-pass transmembrane protein with a glycosylated extracellular component which facilitates the outgrowth and migration of neurons in the corticospinal tract. The intracellular c-terminus however binds to the spectrin-repeat containing protein, ankyrin, linking the cell membrane to intracellular spectrin. Thus, strumpellin with its spectrin domain may also be involved in this process.

EXAMPLE 6

Zebrafish Rescue Experiments

In order to validate the functional phenotype of SPG8 mutations in vivo, a zebrafish model was developed. Morpholino oligonucleotide knockdown of the KIAA0196 protein ortholog in zebrafish (KIAAMO) was performed as described in Example 1 above. It resulted in an enlarged heart cavity along with a curly tail phenotype which severely impaired the ability of the fish to swim properly. The overall phenotype ranged in severity and was classified in 3 major groups: normal, slightly curly, and severely curly. This phenotype was clearly visible after dechorionating by 1 day post fertilization (dpf). At 3 dpf, wildtype zebrafish are ~5 mm long with a straight tail (FIG. 5A). Fish injected with a mismatch-control morpholino (CTLMO) were initially used to titer a KIAAMO specific non-toxic injection dose (FIG. 5b). Injection of the KIAAMO resulted in 66 of 178 (37%) severely curly fish and 50 of 178 (28%) slightly curly fish (See Table 3 below and FIGS. 5c and d).

TABLE 3

Phenotype profile from zebrafish morpholino oligonucleotide knockdown expressed in percent (total number)

| Condition | Normal | Slight curve | Severe curve | Dead | Total |
|---|---|---|---|---|---|
| KIAA0196 morpholino | 19.1 (34) | 28.1 (50) | 37.1 (66) | 15.7 (28) | 178 |
| Control morpholino | 56.1 (83) | 24.3 (36) | 7.4 (11) | 12.2 (18) | 148 |
| Wildtype rescue | 63.2 (127) | 19.4 (39) | 8.0 (16) | 9.5 (9) | 201 |
| Mutant ×14 rescue | 16.0 (32) | 37.0 (74) | 36.0 (72) | 11.0 (22) | 200 |
| Mutant ×15 rescue | 13.2 (29) | 37.4 (82) | 30.1 (66) | 19.2 (42) | 219 |

The KIAAMO fish had a significantly different distribution of phenotypic groups compared to CTLMO injections (p<0.001). When wildtype human KIAA0196 mRNA was co-injected with KIAAMO, the curly tail phenotype was rescued to levels comparable to CTLMO injections (p=0.51) (FIGS. 5e and f). This suggests that in zebrafish, human KIAA0196 mRNA can compensate for the loss of endogenous zebrafish mRNA. Conversely, co-injection of human KIAA0196 mRNA incorporating either the exon 14 or exon 15 mutation failed to significantly rescue the phenotype (FIGS. 5G, H). Injection of mutant exon 14 or exon 15 mRNA alone (without morpholinos) did not lead to curly tail phenotype or influence lethality in zebrafish, suggesting that the two mutations do not exert a dominant negative effect. Approximately 200 embryos were injected per experimental condition (Table 3 above). The difference in distribution between KIAAMO injection alone and KIAAMO co-injection with wildtype mRNA was significant (p<0.001). Similarly, co-injection of wildtype mRNA versus either exon 14 or exon 15 mutant mRNA was significantly different with a p-value <0.001. There was no statistical difference between the co-injection of the exon 14 mutant and the exon 15 mutant (p=0.10).

Figure 6:
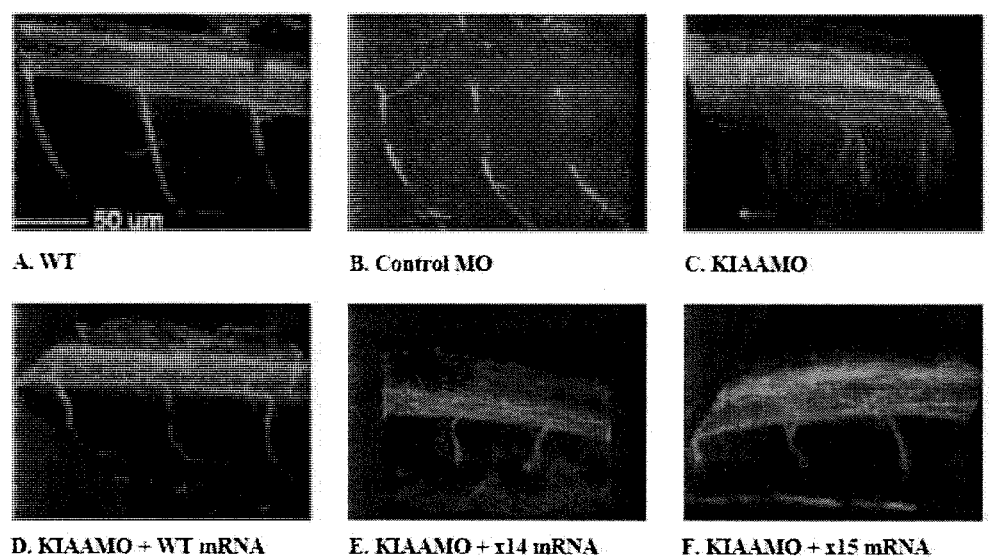
FIG. 6 presents an immunohistochemical analysis in zebrafish of the KIAA0196 knockdown phenotype. A) The motor neurons in the ventral roots of zebrafish are segmented and oriented at 3 dpf. The spinal cord consists of the cell bodies of motor neurons and interneuron bundles. The picture was taken near the gut of the fish. B) The mismatch control has a similar motor neuron distribution compared to the wildtype. C, E, F) Zebrafish injected with KIAAMO and fish co-injected with mutant mRNA have shorter, branching motor neurons which are not oriented. D) Wildtype co-injections partially rescue the motor neuron phenotype; the axons are longer and oriented.

Upon histochemical analysis of the embryos using an anti-acetylated tubulin stain for growing axons using the method described in Example 1 above, it was found that the motor neurons in the spinal cord did not develop normally (FIG. 6). Motor neuron axons in fish injected with KIAAMO alone or with the mutant mRNAs were shorter and showed abnormal branching. The structure of interneurons in the spinal cord was also different. The absence of the KIAA0196 gene or mutations in this gene during early development thus seemed to hamper axonal outgrowth.

EXAMPLE 7

Production of Antibodies

Three different peptides corresponding to amino acids 62-76 (KGPELWESKLDAKPE (SEQ ID NO: 100), 652-669 (VPTRLDKDKLRDYAQLGP (SEQ ID NO: 37)) and 1132-1147 (YVRYTKLPRRVAEAHV (SEQ ID NO: 101)) were synthesized. The sequence of the first peptide (62-76) corresponds to protein residues present near the amino terminal portion of strumpellin. The sequence of the second peptide (652-669) corresponds to residues found in the middle of the protein. Finally, the sequence of the third peptide (1132-1147) corresponds to residues near the carboxy terminal portion of the protein.

Every month a dose of each peptide was injected to two separate rabbits. These intraperitoneal injections were carried over for a period of five months. A month following each injections, blood samples were collected from each animals and the cellular fraction removed the sera were stored at −80° C. Following the recovery of the last samples where a complete final bleed was achieved, all the animals were euthanized. The sera from the second peptide (652-669) were observed to be the most specific for strumpellin (FIG. 7b).

EXAMPLE 8

Detecting KIAA0196 Mutations in a Subject Sample

The method for detecting a mutation in the KIAA0196 gene involves the amplification of a patient's DNA by the Polymerase Chain Reaction (PCR) using primers designed to specifically recognize flanking genomic sequences of the KIAA0196 gene, such as those listed in Table 1 above. A series of PCR amplifications are necessary to cover the entire coding regions of KIAA0196 and its flanking splice site regions. The product of these amplifications are subsequently sequenced and examined for the presence of mutations using appropriate software (e.g. the SeqMan™ program from the DNASTAR™ sequence analysis package). Sequences of the patient's DNA amplifications are compared to a reference sequence where no mutation can be found and or to the reference sequences from databases like UCSC.

The optimal PCR reactions for the amplification of KIAA0196 are the following: 50 ng DNA, 20 pmol of each oligonucleotide primer, 10× buffer, 0.25 nM dNTPs and 0.15 ul of Taq (Qiagen). An initial denaturation step of 5 minutes at 94° C. is done and it is followed by 30 cycles of 30 seconds denaturation at 94° C., 30 seconds annealing at 55° C. (for all exons except for exons 15 and 26), and 45 seconds elongation at 72° C. A final extension at 72° C. of 7 minutes is finally performed. In the case of exon 15, a 50° C. annealing temperature was used, and in the case of exon 26, 10 cycles of a touchdown reaction were performed from 68° C.-63° C., followed by 25 cycles at 63° C.

To identify the three specific mutations of the present invention, three separate PCRs were performed using oligonucleotide primers that corresponded to the sequences surrounding exons 11, 14, and 15 with the patients DNA. Following the sequencing of these products, the sequence traces generated by the software were analyzed visually.

EXAMPLE 9

Detecting Mutant KIAA0196 RNA in a Subject Sample

To detect the presence of mutant RNA, PCR reactions may be performed using oligonucleotide primers specific to the cDNA sequence (coding sequences of DNA exclusively, not sequences flanking the different coding regions) of KIAA0196, such as those in Table 4 below. RNA needs to be extracted from patients using standard methods, and a reverse-transcription PCR(RT-PCR) is performed. The cDNA products generated by this reaction are then used as a template for the PCR amplifications. The sequence trace results are then analyzed using appropriate software for the detection of mutations. The type of protein modifications the occurrence of any mutation within the RNA (here represented by the cDNA) can be predicted using a table listing the amino acids produced by the different codons possible.

interactions with the mutated proteins are to be investigated only in the event that these are stably expressed. Interactions occurring through the spectrin domain of strumpellin in particular is examined.

Although the present invention has been described hereinabove by way of specific embodiments thereof, it can be modified, without departing from the spirit and nature of the subject invention as defined in the appended claims.

TABLE 4

Primers for cDNA analysis of the KIAA0196 gene

| | | |
|---|---|---|
| KIAA0196rna1F | CCGGGACTGCGGATAGAAGA | (SEQ ID NO: 102) |
| KIAA0196rna1R | AATCCTGTAGCTCTGGCTTAGCATC | (SEQ ID NO: 103) |
| KIAA0196rna2F | TCTGAGTTTATTCCTGCTGTGTTCA | (SEQ ID NO: 104) |
| KIAA0196rna2R | CTCTCGGGATAGTTGGATGGTCTTT | (SEQ ID NO: 105) |
| KIAA0196rna3F | GCTGCTCGATCTTCTGCTGATTCAA | (SEQ ID NO: 106) |
| KIAA0196rna3R | ATCGGATGGCAACATTGCAGTCTCT | (SEQ ID NO: 107) |
| KIAA0196rna4F | TAAGGGAGGAGATGGTTCTGGACA | (SEQ ID NO: 108) |
| KIAA0196rna4R | TCGAGTATCGGCAAGAAACTGACA | (SEQ ID NO: 109) |
| KIAA0196rna5bF | TGAAACCCCTAACCAGAGTGGAGAAA | (SEQ ID NO: 110) |
| KIAA0196rna5R | ATCGTGGGCCTAGCTGAGCATAGT | (SEQ ID NO: 111) |
| KIAA0196rna6F | AGCTTCAGACCCACGACATTATTG | (SEQ ID NO: 112) |
| KIAA0196rna6R | CCACAGGGGTAAACTTGGGTATTG | (SEQ ID NO: 113) |
| KIAA0196rna7F | TTGGCAAAGCATGTACCAGTCCAC | (SEQ ID NO: 114) |
| KIAA0196rna7R | TCTGCATCTGCCCAACCTTCATTA | (SEQ ID NO: 115) |
| KIAA0196rna8F | TCCGCCATTGCCAAAACACAGA | (SEQ ID NO: 116) |
| KIAA0196rna8R | GGCCAATCAGCGCCAGGAACT | (SEQ ID NO: 117) |
| KIAA0196rna9F | GCTTGTCCTGGGACTGCTCACTC | (SEQ ID NO: 118) |
| KIAA0196rna9R | AGAGGCAGTACAAAAATGTGTTCT | (SEQ ID NO: 119) |

EXAMPLE 10

Assay to Detect Mutation in Subject Sample

A Western blot is performed using an antibody specific to the KIAA0196 product and protein lysates prepared from patient tissue or lymphoblastoid cell lines to detect mutant protein in a patient's biological sample.

EXAMPLE 11

Identifying Strumpellin-Interacting Proteins

Protein-protein protocols such as the yeast two hybrid (Y2H), GST pulldown and co-immunoprecipitation approaches are used to identify strumpellin-interacting proteins. These three approaches are performed using both normal and mutant strumpellin to establish which interactions may be specific to the mutated forms of the protein, but also to see in some interactions with the normal form of the protein decrease or increase with the mutated proteins. Such

REFERENCES

1. McMonagle P, Webb S, Hutchinson M (2002) The prevalence of "pure" autosomal dominant hereditary spastic paraparesis in the island of Ireland. J Neurol Neurosurg Psychiatry 72:43-46.
2. Silva M C, Coutinho P, Pinheiro C D, Neves J M, Serrano P (1997) Hereditary ataxias and spastic paraplegias: methodological aspects of a prevalence study in Portugal. J Clin Epidemiol 50:1377-1384.
3. Polo J M, Calleja J, Combarros O, Berciano J (1991) Hereditary ataxias and paraplegias in Cantabria, Spain. An epidemiological and clinical study. Brain 114 (Pt 2):855-866.
4. Fink J K (1997) Advances in hereditary spastic paraplegia. Current Opinion in Neurology 10:313-318.
5. Harding A E (1993) Hereditary spastic paraplegias. [Review]. Seminars in Neurology 13:333-336.
6. Harding A E (1983) Classification of the hereditary ataxias and paraplegias. Lancet 1:1151-1155.
7. Behan W M, Maia M (1974) Strumpell's familial spastic paraplegia: genetics and neuropathology. J Neurol Neurosurg Psychiatry 37:8-20.

8. Deluca G C, Ebers G C, Esiri M M (2004) The extent of axonal loss in the long tracts in hereditary spastic paraplegia. Neuropathol Appl Neurobio 130:576-584.
9. Soderblom C, Blackstone C (2006) Traffic accidents: Molecular genetic insights into the pathogenesis of the hereditary spastic paraplegias. Pharmacol Ther 109:42-56.
10. Zuchner S, Kail M E, Nance M A, Gaskell P C, Svenson I K, Marchuk D A, Pericak-Vance M A, Ashley-Koch A E (2006) A new locus for dominant hereditary spastic paraplegia maps to chromosome 2p12. Neurogenetics 7:127-129.
11. Klebe S, Azzedine H, Dun A, Bastien P, Bouslam N, Elleuch N, Forlani S, Charon C, Koenig M, Melki J, Brice A, Stevanin G (2006) Autosomal recessive spastic paraplegia (SPG30) with mild ataxia and sensory neuropathy maps to 2q37.3. Brain.
12. Hazan J, Fonknechten N, Mavel D, Paternotte C, Samson D, Artiguenave F, Davoine C S, Cruaud C, Dun A, Wincker P, Brother P, Cattolico L, Barbe V, Burgunder J M, Prud'homme J F, Brice A, Fontaine B, Heilig B, Weissenbach J (1999) Spastin, a new AAA protein, is altered in the most frequent form of autosomal dominant spastic paraplegia. Nature Genetics 23:296-303.
13. Meijer I A, Hand C K, Cossette P, Figlewicz D A, Rouleau G A (2002) Spectrum of SPG4 mutations in a large collection of North American families with hereditary spastic paraplegia. Arch Neurol 59:281-286.
14. Hedera P, Rainier S, Alvarado D, Zhao X, Williamson J, Otterud B, Leppert M, Fink J K (1999) Novel locus for autosomal dominant hereditary spastic paraplegia, on chromosome 8q. Am J Hum Genet. 64:563-569.
15. Reid E, Dearlove A M, Whiteford M L, Rhodes M, Rubinsztein D C (1999) Autosomal dominant spastic paraplegia: refined SPG8 locus and additional genetic heterogeneity. Neurology 53:1844-1849.
16. Rocco P, Vainzof M, Froehner S C, Peters M F, Marie S K, Passos-Bueno M R, Zatz M (2000) Brazilian family with pure autosomal dominant spastic paraplegia maps to 8q: analysis of muscle beta 1 syntrophin. Am J Med Genet. 92:122-127.
17. Casari G, De Fusco M, Ciarmatori S, Zeviani M, Mora M, Fernandez P, De Michele G, Filla A, Cocozza S, Marconi R, Dun A, Fontaine B, Ballabio A (1998) Spastic paraplegia and OXPHOS impairment caused by mutations in paraplegin, a nuclear encoded mitochondrial metalloprotease. Cell 93:973-983.
18. Cottingham R W, Jr., Idury R M, Schaffer A A (1993) Faster sequential genetic linkage computations. Am J Hum Genet. 53:252-263.
19. Bourgeois S, Labuda D (2004) Dynamic allele-specific oligonucleotide hybridization on solid support. Anal Biochem 324:309-311.
20. Labuda D, Krajinovic M, Richer C, Skoll A, Sinnett H, Yotova V, Sinnett D (1999) Rapid detection of CYP1A1, CYP2D6, and NAT variants by multiplex polymerase chain reaction and allele-specific oligonucleotide assay. Anal Biochem 275:84-92.
21. Guex N, Peitsch M C (1997) SWISS-MODEL and the Swiss-PdbViewer: an environment for comparative protein modeling. Electrophoresis 18:2714-2723.
22. Westerfield M (1995) The Zebrafish book. A guide for laboratory use of zebrafish (Danio rerio).
23. Nasevicius A, Ekker S C (2000) Effective targeted gene 'knockdown' in zebrafish. Nat Genet. 26:216-220.
24. Jones D T (1999) Protein secondary structure prediction based on position-specific scoring matrices. J Mol Biol 292:195-202.
25. Mannan A U, Krawen P, Sauter S M, Boehm J, Chronowska A, Paulus W, Neesen J, Engel W (2006) ZFYVE27 (SPG33), a Novel Spastin-Binding Protein, Is Mutated in Hereditary Spastic Paraplegia. Am J Hum Genet. 79:351-357.
26. Djinovic-Carugo K, Gautel M, Ylanne J, Young P (2002) The spectrin repeat: a structural platform for cytoskeletal protein assemblies. FEBS Lett 513:119-123.
27. Ylanne J, Scheffzek K, Young P, Saraste M (2001) Crystal Structure of the alpha-Actinin Rod: Four Spectrin Repeats Forming a Thight Dimer. Cell Mol Biol Lett 6:234.
28. Koenig M, Monaco A P, Kunkel L M (1988) The complete sequence of dystrophin predicts a rod-shaped cytoskeletal protein. Cell 53:219-226.
29. Ishikawa K, Tom S, Tsunemi T, Li M, Kobayashi K, Yokota T, Amino T, et al. (2005) An autosomal dominant cerebellar ataxia linked to chromosome 16q22.1 is associated with a single-nucleotide substitution in the 5' untranslated region of the gene encoding a protein with spectrin repeat and rho Guanine-nucleotide exchange-factor domains. Am J Hum Genet. 77:280-296.
30. Ikeda Y, Dick K A, Weatherspoon M R, Gincel D, Armbrust K R, Dalton J C, Stevanin G, Durr A, Zuhlke C, Burk K, Clark H B, Brice A, Rothstein J D, Schut U, Day J W, Ranum L P (2006) Spectrin mutations cause spinocerebellar ataxia type 5. Nat Genet. 38:184-190.
31. Jouet M, Rosenthal A, Armstrong G, MacFarlane J, Stevenson R, Paterson J, Metzenberg A, Ionasescu V, Temple K, Kenwrick S (1994) X-linked spastic paraplegia (SPG1), MASA syndrome and X-linked hydrocephalus result from mutations in the L1 gene. Nat Genet. 7:402-407.
32. Porkka K P, Tammela T L, Vessella R L, Visakorpi T (2004) RAD21 and KIAA0196 at 8q24 are amplified and overexpressed in prostate cancer. Genes Chromosomes Cancer 39:1-10.
33. Hochheimer A, Zhou S, Zheng S, Holmes M C, Tjian R (2002) TRF2 associates with DREF and directs promoter-selective gene expression in *Drosophila*. Nature 420:439-445.
34. Shimada M, Nakadai T, Tamura T A (2003) TATA-binding protein-like protein (TLP/TRF2/TLF) negatively regulates cell cycle progression and is required for the stress-mediated G(2) checkpoint. Mol Cell Biol 23:4107-4120.
35. Hirose F, Yamaguchi M, Handa H, Inomata Y, Matsukage A (1993) Novel 8-base pair sequence (Drosophila DNA replication-related element) and specific binding factor involved in the expression of *Drosophila* genes for DNA polymerase alpha and proliferating cell nuclear antigen. J Biol Chem 268:2092-2099.
36. Brand M, Heisenberg C P, Warga R M, Pelegri F, Karlstrom R O, Beuchle D, Picker A, Jiang Y J, Furutani-Seiki M, van Eeden F J, Granato M, Haffter P, Hammerschmidt M, Kane D A, Kelsh R N, Mullins M C, Odenthal J, Nusslein-Volhard C (1996) Mutations affecting development of the midline and general body shape during zebrafish embryogenesis. Development 123:129-142.
37. Wood J D, Landers J A, Bingley M, McDermott C J, Thomas-McArthur V, Gleadall L J, Shaw P J, Cunliffe V T (2006) The microtubule-severing protein Spastin is essential for axon outgrowth in the zebrafish embryo. Hum Mol Genet. 15:2763-2771.

38. Do C B, Mahabhashyam M S P, Brudno M, Batzoglou S (2005) PROBCONS: Probabilistic Consistency-based Multiple Sequence Alignment. Genome Res 15: 330-340.
39. Kelley L A, MacCallum R M, Sternberg M J (2000) Enhanced genome annotation using structural profiles in the program 3D-PSSM. J. Mol. Biol. 299:499-520
40. Kent W J, Sugnet C W, Furey T S, Roskin K M, Pringle T H, Zahler A M, Haussler D (2002) The Human Genome Browser at UCSC. Genome Res 12(6): 996-1006.
41. Finn R D, Mistry J, Schuster-Bockler B, Griffiths-Jones S, Hollich V, Lassmann T, Moxon S, Marshall M, Khanna A, Durbin R, Eddy S R, Sonnhammer E L L, Bateman A (2006) Pfam: clans, web tools and services. Nucleic Acids Research 34:D247-251.
42. Hebsgaard S M, Korning P G, Tolstrup N, Engelbrecht J, Rouze P, Brunak S (1996) Splice site prediction in *Arabidopsis thaliana* DNA by combining local and global sequence information. Nucleic Acids Research 24: 3439-3452.
43. Quevillon E, Silventoinen V, Pillai S, Harte N, Mulder N, Apweiler R, Lopez R (2005) InterProScan: protein domains identifier. Nucleic Acids Research 33: W116-W120.

The invention claimed is:

1. An isolated nucleic acid molecule comprising between 20 and 300 contiguous nucleotides of: (a) SEQ ID NO: 20; (b) SEQ ID NO: 22; (c) SEQ ID NO: 24; or (d) the complement of (a), (b) or (c), wherein the between 20 and 300 contiguous nucleotides comprise a nucleotide corresponding to position 2205 or 2186 relative to SEQ ID NO: 18, and wherein the isolated nucleic acid molecule is detectably labeled.

2. A vector comprising the nucleic acid molecule of claim 1.

3. A recombinant host cell comprising the vector of claim 2.

4. An isolated nucleic acid molecule comprising between 20 and 300 contiguous nucleotides of a nucleotide sequence encoding a polypeptide comprising the amino acid sequence of (a) SEQ ID NO: 21; (b) SEQ ID NO: 23; (e) SEQ ID NO: 25; or (d) the complement of the sequence in (a), (b) or (c), wherein the between 20 and 300 contiguous nucleotides comprise a nucleotide corresponding to position 2205 or 2186 relative to SEQ ID NO: 18, and wherein the isolated nucleic acid molecule is detectably labeled.

5. A vector comprising the nucleic acid molecule of claim 4.

6. A recombinant host cell comprising the vector of claim 5.

7. The isolated nucleic acid molecule of claim 1, wherein the nucleic acid molecule is detectably labeled with a ligand, fluorophore, chemiluminescent agent, enzyme, antibody, or combination thereof.

8. The isolated nucleic acid molecule of claim 4, wherein the nucleic acid molecule is detectably labeled with a ligand, fluorophore, chemiluminescent agent, enzyme, antibody, or combination thereof.

9. The isolated nucleic acid molecule of claim 1, wherein the isolated nucleic acid molecule comprises a modified sugar, modified phosphate group, modified nucleotide, or combination thereof.

10. The isolated nucleic acid molecule of claim 4, wherein the isolated nucleic acid molecule comprises a modified sugar, modified phosphate group, modified nucleotide, or combination thereof.

11. The isolated nucleic acid molecule of claim 1, wherein the isolated nucleic acid is affixed to a solid support.

12. The isolated nucleic acid molecule of claim 4, wherein the isolated nucleic acid is affixed to a solid support.

13. An isolated nucleic acid molecule comprising between 20 and 300 contiguous nucleotides of: (a) SEQ ID NO: 22; (b) SEQ ID NO: 24; or (c) the complement of (a), (b) or (c), wherein the between 20 and 300 contiguous nucleotides comprise a nucleotide corresponding to position 2205 or 2186 relative to SEQ ID NO: 18, and wherein the isolated nucleic acid molecule is detectably labeled.

14. An array of nucleic acid molecules attached to a solid support, the array comprising an isolated nucleic acid molecule according to claim 1 or 4.

* * * * *